(12) United States Patent
Naidu et al.

(10) Patent No.: US 7,037,908 B2
(45) Date of Patent: May 2, 2006

(54) HIV INTEGRASE INHIBITORS

(75) Inventors: B. Narasimhulu Naidu, Durham, CT (US); Michael A. Walker, Durham, CT (US); Margaret E. Sorenson, Meriden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 54 days.

(21) Appl. No.: 10/824,917

(22) Filed: Apr. 15, 2004

(65) Prior Publication Data

US 2004/0229892 A1 Nov. 18, 2004

Related U.S. Application Data

(60) Provisional application No. 60/465,176, filed on Apr. 24, 2003.

(51) Int. Cl.
*C07D 417/10* (2006.01)
*A61K 31/506* (2006.01)

(52) U.S. Cl. .............. 514/222.2; 514/259.1; 514/269; 544/3; 544/281; 544/319

(58) Field of Classification Search .............. 544/3, 544/281, 319; 514/222.2, 259.1, 269
See application file for complete search history.

(56) References Cited

FOREIGN PATENT DOCUMENTS

| JP | 2004-244320 | 9/2004 |
|---|---|---|
| WO | WO 02/070491 A1 | 9/2002 |
| WO | WO 03/016226 A1 | 2/2003 |
| WO | WO 03/016275 A1 | 2/2003 |
| WO | WO 03/035076 A1 | 5/2003 |
| WO | WO 03/035077 A1 | 5/2003 |

*Primary Examiner*—Deepak Rao
(74) *Attorney, Agent, or Firm*—James Epperson

(57) ABSTRACT

The present invention relates to a series of pyrimidine compounds of Formula I which inhibit HIV integrase and to pharmaceutical compositions and methods of treatment for AIDS or ARC using these compounds

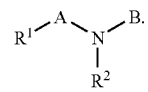

13 Claims, No Drawings

HIV INTEGRASE INHIBITORS

CROSS-REFERENCE TO RELATED APPLICATIONS

This application claims the benefit of U.S. provisional application No. 60/465,176, filed Apr. 24, 2003.

BACKGROUND OF THE INVENTION

HIV expresses three enzymes, reverse transcriptase, an aspartyl protease and integrase, all of which are potential antiviral targets for the development of drugs for the treatment of AIDS. However, integrase stands out as being the only viral enzyme not targeted by current therapy. The integrase enzyme is responsible for insertion of the viral cDNA into the host cell genome, which is a critical step in the viral life cycle. There are a number of discrete steps involved in this process including processing of the viral cDNA by removal of two bases from each 3'-terminus and joining of the recessed ends to the host DNA. Studies have shown that in the absence of a functional integrase enzyme HIV is not infectious. (Lafemina, R. L.; Schneider, C. L.; Robbins, H. L.; Callahan, P. L.; LeGrow, K.; Roth, E.; Emini, E. A. *J. Virol.* 1992, 66, 7414–7419 and Englund, G.; Theodore, T. S.; Freed, E.; Engelman, A.; Martin, M. A. *J. Virol.* 1995, 69, 3216–3219) Therefore, an inhibitor of integrase would be useful as a therapy for AIDS and HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavirdine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. *N. Engl. J. Med*. 1998, 338, 853–860).

Unfortunately, not all patients are responsive and a large number fail this therapy. In fact, approximately 30–50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381–390). Clearly there is a need for new antiviral agents, preferably targeting other viral enzymes to reduce the rate of resistance and suppress viral replication even further.

A number of HIV integrase inhibitors have been reported. These include nucleotide-based inhibitors, known DNA binders, catechols and hydrazide containing derivatives (Neamati, N.; Sunder, S.; Pommier, Y., *Drug Disc. Today*, 1997, 2, 487).

Certain pyrimidines and pyrimidinones have been disclosed. WO 02/06246 discloses 2-aryl-4,5-dihydroxy-6-carboxypyrimidines as viral polymerase inhibitors which are proposed for use in treating hepatitis C virus infection. Sunderland, C. J; Botta, M.; Aime, S.; and Raymond, K. N. *Inorg. Chem.* (2001) 40, 6746–6756 discloses the synthesis of 6-carboxamido-5,4-hydroxypyrimidinones as gadolinium chelating agents. This action makes the compounds useful for treating HIV infection and AIDS. The invention also encompasses pharmaceutical compositions and methods for treating those infected with HIV. Nothing in these references teaches or suggests the novel compounds of this invention or their use as HIV integrase inhibitors.

SUMMARY OF INVENTION

The invention encompasses a series of compounds of structural Formula I which inhibit HIV integrase. This action makes the compounds useful for treating HIV infection and AIDS. The invention also encompasses pharmaceutical compositions and methods for treating those infected with HIV.

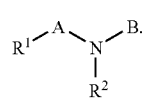

I

DETAILED DESCRIPTION OF THE INVENTION

The invention comprises compounds of Formula I, including pharmaceutically acceptable salts and solvates, their pharmaceutical compositions, and their use in preventing HIV attachment and treating those infected with HIV. The compounds of Formula I are described with the following meanings:

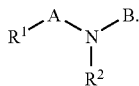

wherein
A is methylene or 1,1-disubstituted ethylene;
B is selected from the group consisting of

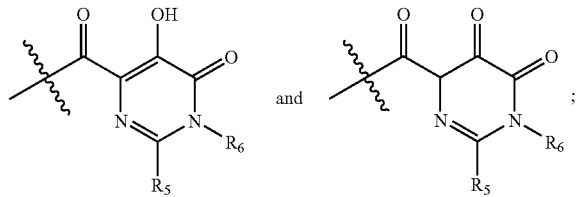

R¹ is phenyl, pyridinyl or dioxolanylphenyl and is unsubstituted or substituted with 1 to 3 R³;

R² is hydrogen, methyl, or OR⁴;

R³ is independently selected from halo, $C_{1-6}$alkyl, $C_{1-2}$ perfluoroalkyl, $C_{1-6}$alkoxy, $C_{1-6}$alkylthioxy, and cyano;

R⁴ is hydrogen or $C_{1-6}$alkyl;

R⁵ is Ar¹ or Ar²;

R⁶ is $C_{1-6}$alkyl;

Ar¹ is phenyl unsubstituted or substituted with 1–2 substituents selected from halo, $C_{1-6}$alkoxy, $CO_2R^4$, $N(R^4)(SO_2C_{1-6}alkyl)$, $SO_2N(C_{1-6}alkyl)_2$, and dioxothiazinanyl;

Ar² is a heteroaryl moiety selected from the group consisting of pyridinyl, pyrrolyl, furanyl, and imidazopyrimidinyl and is unsubstituted or substituted with 1–2 substituents selected from halo, $C_{1-6}$alkyl, $C_{1-6}$alkoxy, $CO_2R^4$, $N(R^4)(SO_2C_{1-6}alkyl)$, $SO_2N(C_{1-6}alkyl)_2$, $N(R^7)_2$, and dioxothiazinanyl;

R⁷ is hydrogen, $C_{1-6}$alkyl, $C_{1-6}$alkylOR⁴.

One aspect of the invention are compounds of Formula I wherein R¹ is phenyl unsubstituted or substituted with 1 to 3 R³.

Another aspect of the invention are compounds of Formula I where R¹ is phenyl substituted with 1–2 R³ selected from the group consisting of chloro, fluoro, methyl, and trifluoromethyl.

Another aspect of the invention are compounds of Formula I where R² is hydrogen.

Another aspect of the invention are compounds of Formula I where R⁵ is Ar¹.

Another aspect of the invention are compounds of Formula I where Ar¹ is phenyl substituted with 1–2 R³ selected from the group consisting of chloro, fluoro, methoxy, N(Me)SO₂Me, SO2N(Me)₂, SO₂Me, and dioxothiazinanyl.

Another aspect of the invention are compounds of Formula I where R⁵ is Ar².

Another aspect of the invention are compounds of Formula I where Ar² is substituted with 1–2 substituents selected from the group consisting of chloro, fluoro, methyl, methoxy, dimethylamino, 2-hydroxyethylamino, di(2-hydroxyethyl)amino, N(Me)SO₂Me, SO₂N(Me)₂, SO₂Me, and dioxothiazinanyl.

Another aspect of the invention are compounds of Formula I where R⁶ is methyl.

Some compounds of the invention are
N-(4-fluorobenzyl)-2-(2,6-difluorophenyl)-5-hydroxy-1-methyl-6-oxo-1,6-dihydropyrimidine-4-carboxamide;
N-(3,4-dichlorobenzyl)-2-(2,6-difluorophenyl)-5-hydroxy-1-methyl-6-oxo-1,6-dihydropyrimidine-4-carboxamide;
N-(3,4-difluorobenzyl)-2-(2,6-difluorophenyl)-5-hydroxy-1-methyl-6-oxo-1,6-dihydropyrimidine-4-carboxamide;
N-(4-chlorobenzyl)-2-(2,6-difluorophenyl)-5-hydroxy-1-methyl-6-oxo-1,6-dihydropyrimidine-4-carboxamide;
N-(4-methylbenzyl)-2-(2,6-difluorophenyl)-5-hydroxy-1-methyl-6-oxo-1,6-dihydropyrimidine-4-carboxamide;
N-(3,4-dimethylbenzyl)-2-(2,6-difluorophenyl)-5-hydroxy-1-methyl-6-oxo-1,6-dihydropyrimidine-4-carboxamide;
N-(3-chloro-4-methylbenzyl)-2-(2,6-difluorophenyl)-5-hydroxy-1-methyl-6-oxo-1,6-dihydropyrimidine-4-carboxamide;
N-(2,4-difluorobenzyl)-2-(2,6-difluorophenyl)-5-hydroxy-1-methyl-6-oxo-1,6-dihydropyrimidine-4-carboxamide;
N-(2-methylbenzyl)-2-(2,6-difluorophenyl)-5-hydroxy-1-methyl-6-oxo-1,6-dihydropyrimidine-4-carboxamide;
N-(4-fluoro-2-(trifluoromethyl)benzyl)-2-(2,6-difluorophenyl)-5-hydroxy-1-methyl-6-oxo-1,6-dihydropyrimidine-4-carboxamide;
N-(4-(trifluoromethyl)benzyl)-2-(2,6-difluorophenyl)-5-hydroxy-1-methyl-6-oxo-1,6-dihydropyrimidine-4-carboxamide;
N-(benzo[d][1,3]dioxol-5-ylmethyl)-2-(2,6-difluorophenyl)-5-hydroxy-1-methyl-6-oxo-1,6-dihydropyrimidine-4-carboxamide;
2-(2,6-difluorophenyl)-5-hydroxy-1-methyl-6-oxo-N-(1-phenylethyl)-1,6-dihydropyrimidine-4-carboxamide;
N-(2-(methylthio)benzyl)-2-(2,6-difluorophenyl)-5-hydroxy-1-methyl-6-oxo-1,6-dihydropyrimidine-4-carboxamide;
N-(3-fluoro-4-(trifluoromethyl)benzyl)-2-(2,6-difluorophenyl)-5-hydroxy-1-methyl-6-oxo-1,6-dihydropyrimidine-4-carboxamide;
N-(3,5-bis(trifluoromethyl)benzyl)-2-(2,6-difluorophenyl)-5-hydroxy-1-methyl-6-oxo-1,6-dihydropyrimidine-4-carboxamide;
2-(2,6-difluorophenyl)-5-hydroxy-1-methyl-6-oxo-N-(pyridin-2-ylmethyl)-1,6-dihydropyrimidine-4-carboxamide;
N-benzyl-5-hydroxy-1-methyl-6-oxo-2-phenyl-1,6-dihydropyrimidine-4-carboxamide;
N-(4-chlorobenzyl)-5-hydroxy-1-methyl-6-oxo-2-(pyridin-2-yl)-1,6-dihydropyrimidine-4-carboxamide;
N-(3,4-dichlorobenzyl)-5-hydroxy-1-methyl-6-oxo-2-(pyridin-2-yl)-1,6-dihydropyrimidine-4-carboxamide;
N-(3,4-difluorobenzyl)-5-hydroxy-1-methyl-6-oxo-2-(pyridin-2-yl)-1,6-dihydropyrimidine-4-carboxamide;
N-(4-methylbenzyl)-5-hydroxy-1-methyl-6-oxo-2-(pyridin-2-yl)-1,6-dihydropyrimidine-4-carboxamide;
N-(3,4-dimethylbenzyl)-5-hydroxy-1-methyl-6-oxo-2-(pyridin-2-yl)-1,6-dihydropyrimidine-4-carboxamide;
N-(3-chloro-4-methylbenzyl)-5-hydroxy-1-methyl-6-oxo-2-(pyridin-2-yl)-1,6-dihydropyrimidine-4-carboxamide;
N-(4-fluorobenzyl)-5-hydroxy-1-methyl-6-oxo-2-(pyridin-2-yl)-1,6-dihydropyrimidine-4-carboxamide;
N-(3,4-dichlorobenzyl)-5-hydroxy-2-(2-methoxyphenyl)-1-methyl-6-oxo-1,6-dihydropyrimidine-4-carboxamide;
N-(4-fluorobenzyl)-5-hydroxy-2-(2-methoxyphenyl)-1-methyl-6-oxo-1,6-dihydropyrimidine-4-carboxamide;
N-(3,4-dimethylbenzyl)-5-hydroxy-2-(2-methoxyphenyl)-1-methyl-6-oxo-1,6-dihydropyrimidine-4-carboxamide;
N-(3-chloro-4-methylbenzyl)-5-hydroxy-2-(2-methoxyphenyl)-1-methyl-6-oxo-1,6-dihydropyrimidin-4-carboxamide;

N-(4-fluorobenzyl)-2-(4-fluoro-2-(methylsulfonyl)phenyl)-5-hydroxy-1-methyl-6-oxo-1,6-dihydropyrimidine-4-carboxamide;

N-(3,4-dichlorobenzyl)-2-(4-fluoro-2-(methylsulfonyl)phenyl)-5-hydroxy-1-methyl-6-oxo-1,6-dihydropyrimidine-4-carboxamide;

N-(3,4-dimethylbenzyl)-2-(4-fluoro-2-(methylsulfonyl)phenyl)-5-hydroxy-1-methyl-6-oxo-1,6-dihydropyrimidine-4-carboxamide;

N-(4-fluorobenzyl)-2-(2-fluoro-6-(N-methylmethan-3-ylsulfonamido)phenyl)-5-hydroxy-1-methyl-6-oxo-1,6-dihydropyrimidine-4-carboxamide;

N-(3,4-dichlorobenzyl)-2-(2-fluoro-6-(N-methylmethan-3-ylsulfonamido)phenyl)-5-hydroxy-1-methyl-6-oxo-1,6-dihydropyrimidine-4-carboxamide;

N-(3-chloro-4-methylbenzyl)-2-(2-fluoro-6-(N-methylmethan-3-ylsulfonamido)phenyl)-5-hydroxy-1-methyl-6-oxo-1,6-dihydropyrimidine-4-carboxamide;

N-(4-fluorobenzyl)-2-(2,6-dimethoxyphenyl)-5-hydroxy-1-methyl-6-oxo-1,6-dihydropyrimidine-4-carboxamide;

N-(3,4-dichlorobenzyl)-2-(2,6-dimethoxyphenyl)-5-hydroxy-1-methyl-6-oxo-1,6-dihydropyrimidine-4-carboxamide;

N-(3,4-dimethylbenzyl)-2-(2,6-dimethoxyphenyl)-5-hydroxy-1-methyl-6-oxo-1,6-dihydropyrimidine-4-carboxamide;

N-(3-chloro-4-methylbenzyl)-2-(2,6-dimethoxyphenyl)-5-hydroxy-1-methyl-6-oxo-1,6-dihydropyrimidine-4-carboxamide;

N-(4-fluorobenzyl)-5-hydroxy-1-methyl-2-(2-(1,1-Dioxo-1$\lambda^6$-[1,2]thiazinan-2-yl)-1,6-dihydropyrimidine-4-carboxamide;

N-(3,4-dichlorobenzyl)-5-hydroxy-1-methyl-2-(2-(1,1-Dioxo-1$\lambda^6$-[1,2]thiazinan-2-yl)-6-oxo-1,6-dihydropyrimidine-4-carboxamide;

N-(3,4-dimethylbenzyl)-5-hydroxy-1-methyl-2-(2-(1,1-Dioxo-1$\lambda^6$-[1,2]thiazinan-2-yl)-6-oxo-1,6-dihydropyrimidine-4-carboxamide;

N-(3-chloro-4-methylbenzyl)-5-hydroxy-1-methyl-2-(2-(1,1-Dioxo-1$\lambda^6$-[1,2]thiazinan-2-yl)-6-oxo-1,6-dihydropyrimidine-4-carboxamide;

N-(4-fluorobenzyl)-5-hydroxy-1-methyl-2-(2-morpholinophenyl)-6-oxo-1,6-dihydropyrimidine-4-carboxamide;

N-(3,4-dichlorobenzyl)-5-hydroxy-1-methyl-2-(2-morpholinophenyl)-6-oxo-1,6-dihydropyrimidine-4-carboxamide;

N-(3,4-dimethylbenzyl)-5-hydroxy-1-methyl-2-(2-morpholinophenyl)-6-oxo-1,6-dihydropyrimidine-4-carboxamide;

N-(3-chloro-4-methylbenzyl)-5-hydroxy-1-methyl-2-(2-morpholinophenyl)-6-oxo-1,6-dihydropyrimidine-4-carboxamide;

N-(4-fluorobenzyl)-2-(2-dimethylsulfamoylphenyl)-5-hydroxy-1-methyl-6-oxo-1,6-dihydropyrimidine-4-carboxamide;

N-(3,4-dichlorobenzyl)-2-(2-dimethylsulfamoylphenyl)-5-hydroxy-1-methyl-6-oxo-1,6-dihydropyrimidine-4-carboxamide;

N-(3,4-dimethylbenzyl)-2-(2-dimethylsulfamoylphenyl)-5-hydroxy-1-methyl-6-oxo-1,6-dihydropyrimidine-4-carboxamide;

N-(3-chloro-4-methylbenzyl)-2-(2-dimethylsulfamoylphenyl)-5-hydroxy-1-methyl-6-oxo-1,6-dihydropyrimidine-4-carboxamide;

N-(4-fluorobenzyl)-5-hydroxy-2-(3-[2-(1,1-Dioxo-1$\lambda^6$-[1,2]thiazinan-2-yl)-pyridin-2-yl]-)-1-methyl-6-oxo-1,6-dihydropyrimidine-4-carboxamide;

N-(3,4-dichlorobenzyl)-5-hydroxy-2-(3-[2-(1,1-Dioxo-1$\lambda^6$-[1,2]thiazinan-2-yl)-pyridin-2-yl]-)-1-methyl-6-oxo-1,6-dihydropyrimidine-4-carboxamide;

N-(3,4-dimethylbenzyl)-5-hydroxy-2-(3-[2-(1,1-Dioxo-1$\lambda^6$-[1,2]thiazinan-2-yl)-pyridin-2-yl]-)-1-methyl-6-oxo-1,6-dihydropyrimidine-4-carboxamide;

N-(3-chloro-4-methylbenzyl)-5-hydroxy-2-(3-[2-(1,1-Dioxo-1$\lambda^6$-[1,2]thiazinan-2-yl)-pyridin-2-yl]-)-1-methyl-6-oxo-1,6-dihydropyrimidine-4-carboxamide;

N-(4-fluorobenzyl)-5-hydroxy-2-(6-methoxypyridin-3-yl)-1-methyl-6-oxo-1,6-dihydropyrimidine-4-carboxamide;

N-(3,4-dichlorobenzyl)-5-hydroxy-2-(6-methoxypyridin-3-yl)-1-methyl-6-oxo-1,6-dihydropyrimidine-4-carboxamide;

N-(3,4-dimethylbenzyl)-5-hydroxy-2-(6-methoxypyridin-3-yl)-1-methyl-6-oxo-1,6-dihydropyrimidine-4-carboxamide;

N-(4-fluorobenzyl)-5-hydroxy-2-(3-methoxypyridin-2-yl)-1-methyl-6-oxo-1,6-dihydropyrimidine-4-carboxamide;

N-(4-fluorobenzyl)-2-(3-(dimethylamino)pyridin-2-yl)-5-hydroxy-1-methyl-6-oxo-1,6-dihydropyrimidine-4-carboxamide;

N-(3,4-dichlorobenzyl)-2-(3-(dimethylamino)pyridin-2-yl)-5-hydroxy-1-methyl-6-oxo-1,6-dihydropyrimidine-4-carboxamide;

N-(3,4-dimethylbenzyl)-2-(3-(dimethylamino)pyridin-2-yl)-5-hydroxy-1-methyl-6-oxo-1,6-dihydropyrimidine-4-carboxamide;

N-(3-chloro-4-methylbenzyl)-2-(3-(dimethylamino)pyridin-2-yl)-5-hydroxy-1-methyl-6-oxo-1,6-dihydropyrimidine-4-carboxamide;

N-(4-fluorobenzyl)-5-hydroxy-1-methyl-6-oxo-2-phenyl-1,6-dihydropyrimidine-4-carboxamide;

N-(3,4-dichlorobenzyl)-5-hydroxy-1-methyl-6-oxo-2-phenyl-1,6-dihydropyrimidine-4-carboxamide;

N-(3,4-dimethylbenzyl)-5-hydroxy-1-methyl-6-oxo-2-phenyl-1,6-dihydropyrimidine-4-carboxamide;

N-(3-chloro-4-methylbenzyl)-5-hydroxy-1-methyl-6-oxo-2-phenyl-1,6-dihydropyrimidine-4-carboxamide;

N-(4-fluorobenzyl)-5-hydroxy-2-(3-methoxyphenyl)-1-methyl-6-oxo-1,6-dihydropyrimidine-4-carboxamide;

N-(3,4-dichlorobenzyl)-5-hydroxy-2-(3-methoxyphenyl)-1-methyl-6-oxo-1,6-dihydropyrimidine-4-carboxamide;

N-(3,4-dimethylbenzyl)-5-hydroxy-2-(3-methoxyphenyl)-1-methyl-6-oxo-1,6-dihydropyrimidine-4-carboxamide;

N-(4-fluorobenzyl)-5-hydroxy-2-(4-methoxyphenyl)-1-methyl-6-oxo-1,6-dihydropyrimidine-4-carboxamide;

N-(3,4-dichlorobenzyl)-5-hydroxy-2-(4-methoxyphenyl)-1-methyl-6-oxo-1,6-dihydropyrimidine-4-carboxamide;

N-(3,4-dimethylbenzyl)-5-hydroxy-2-(4-methoxyphenyl)-1-methyl-6-oxo-1,6-dihydropyrimidine-4-carboxamide;

N-(4-fluorobenzyl)-5-hydroxy-2-[2-(2-hydroxyethylamino)phenyl]-1-methyl-6-oxo-1,6-dihydropyrimidine-4-carboxylate;

N-(3,4-dichlorobenzyl)-5-hydroxy-2-[2-(2-hydroxyethylamino)phenyl]-1-methyl-6-oxo-1,6-dihydropyrimidine-4-carboxylate;

N-(4-fluorobenzyl)-2-(2-(bis(2-hydroxyethyl)amino)phenyl)-5-hydroxy-1-methyl-6-oxo-1,6-dihydropyrimidine-4-carboxamide;

2-(4-((4-fluorobenzyl)carbamoyl)-5-hydroxy-1-methyl-6-oxo-1,6-dihydropyrimidin-2-yl)benzoic acid;

2-(4-((3,4-dichlorobenzyl)carbamoyl)-5-hydroxy-1-methyl-6-oxo-1,6-dihydropyrimidin-2-yl)benzoic acid;

N-(4-fluorobenzyl)-2-(2-(dimethylamino)phenyl)-5-hydroxy-1-methyl-6-oxo-1,6-dihydropyrimidine-4-carboxamide;

N-(3,4-dichlorobenzyl)-2-(2-(dimethylamino)phenyl)-5-hydroxy-1-methyl-6-oxo-1,6-dihydropyrimidine-4-carboxamide;
N-(3,4-dimethylbenzyl)-2-(2-(dimethylamino)phenyl)-5-hydroxy-1-methyl-6-oxo-1,6-dihydropyrimidine-4-carboxamide;
N-(3-chloro-4-methylbenzyl)-2-(2-(dimethylamino)phenyl)-5-hydroxy-1-methyl-6-oxo-1,6-dihydropyrimidine-4-carboxamide;
N-(4-fluorobenzyl)-2-(furan-2-yl)-5-hydroxy-1-methyl-6-oxo-1,6-dihydropyrimidine-4-carboxamide;
N-(3,4-dichlorobenzyl)-2-(furan-2-yl)-5-hydroxy-1-methyl-6-oxo-1,6-dihydropyrimidine-4-carboxamide;
N-(3,4-dimethylbenzyl)-2-(furan-2-yl)-5-hydroxy-1-methyl-6-oxo-1,6-dihydropyrimidine-4-carboxamide;
N-(3-chloro-4-methylbenzyl)-2-(furan-2-yl)-5-hydroxy-1-methyl-6-oxo-1,6-dihydropyrimidine-4-carboxamide;
N-(4-fluorobenzyl)-5-hydroxy-1-methyl-6-oxo-2-(pyridin-3-yl)-1,6-dihydropyrimidine-4-carboxamide;
N-(3,4-dichlorobenzyl)-5-hydroxy-1-methyl-6-oxo-2-(pyridin-3-yl)-1,6-dihydropyrimidine-4-carboxamide;
N-(3,4-dimethylbenzyl)-5-hydroxy-1-methyl-6-oxo-2-(pyridin-3-yl)-1,6-dihydropyrimidine-4-carboxamide;
N-(3-chloro-4-methylbenzyl)-5-hydroxy-1-methyl-6-oxo-2-(pyridin-3-yl)-1,6-dihydropyrimidine-4-carboxamide;
N-(4-fluorobenzyl)-5-hydroxy-1-methyl-6-oxo-2-(pyridin-4-yl)-1,6-dihydropyrimidine-4-carboxamide;
N-(3,4-dichlorobenzyl)-5-hydroxy-1-methyl-6-oxo-2-(pyridin-4-yl)-1,6-dihydropyrimidine-4-carboxamide;
N-(3,4-dimethylbenzyl)-5-hydroxy-1-methyl-6-oxo-2-(pyridin-4-yl)-1,6-dihydropyrimidine-4-carboxamide;
N-(3-chloro-4-methylbenzyl)-5-hydroxy-1-methyl-6-oxo-2-(pyridin-4-yl)-1,6-dihydropyrimidine-4-carboxamide;
N-(4-fluorobenzyl)-2-(1,5-dimethyl-1H-pyrrol-2-yl)-5-hydroxy-1-methyl-6-oxo-1,6-dihydropyrimidine-4-carboxamide;
N-(3,4-dichlorobenzyl)-2-(1,5-dimethyl-1H-pyrrol-2-yl)-5-hydroxy-1-methyl-6-oxo-1,6-dihydropyrimidine-4-carboxamide;
N-(3,4-dimethylbenzyl)-2-(1,5-dimethyl-1H-pyrrol-2-yl)-5-hydroxy-1-methyl-6-oxo-1,6-dihydropyrimidine-4-carboxamide;
N-(3-chloro-4-methylbenzyl)-2-(1,5-dimethyl-1H-pyrrol-2-yl)-5-hydroxy-1-methyl-6-oxo-1,6-dihydropyrimidine-4-carboxamide;
N-(4-fluorobenzyl)-2-(2,4-dimethylimidazo[1,5-a]pyrimidin-8-yl)-5-hydroxy-1-methyl-6-oxo-1,6-dihydropyrimidine-4-carboxamide;
N-(3,4-dichlorobenzyl)-2-(2,4-dimethylimidazo[1,5-a]pyrimidin-8-yl)-5-hydroxy-1-methyl-6-oxo-1,6-dihydropyrimidine-4-carboxamide;
N-(3,4-methylbenzyl)-2-(2,4-dimethylimidazo[1,5-a]pyrimidin-8-yl)-5-hydroxy-1-methyl-6-oxo-1,6-dihydropyrimidine-4-carboxamide
N-(3-chloro-4-methylbenzyl)-2-(2,4-dimethylimidazo[1,5-a]pyrimidin-8-yl)-5-hydroxy-1-methyl-6-oxo-1,6-dihydropyrimidine-4-carboxamide.
2-(4-methylaminocarbonyl-phenyl)-5-hydroxy-1-methyl-6-oxo-1,6-dihydro-pyrimidine-4-carboxylic acid 4-fluorobenzylamide; and
N-(4-fluorobenzyl)-5-hydroxy-1-methyl-6-oxo-2-p-tolyl-1,6-dihydropyrimidine-4-carboxamide;

"Alkyl" and "alkoxy" includes straight and branched saturated hydrocarbon substituents. "Aryl" includes carbocyclic and heterocyclic aromatic substituents.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

Certain compounds of Formula I may contain one or more chiral centers and exist in different optically active forms. When compounds of Formula I contain one chiral center, the compounds exist in two enantiomeric forms. The present invention includes both enantiomers and mixtures of enantiomers such as racemic mixtures. The enantiomers may be resolved by methods known in the art. Alternatively, specific enantiomers may be synthesized by asymmetric synthesis using reactions known in the art.

The compounds of this invention can also exist as tautomers, as shown below; therefore the present invention also includes all tautomeric forms.

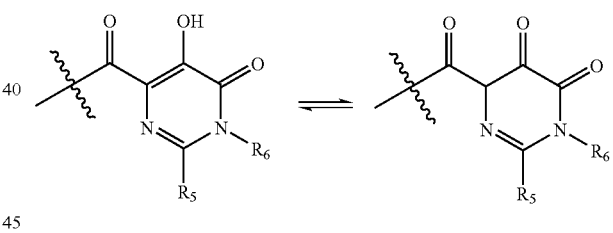

Synthesitic Methods

General methods useful for the synthesis of the compounds of this invention are shown below. Related compounds can be made by reactions known in the art.

Synthetic methods for the preparation of pyrimidines similar to those described in the current invention have been published (Gardelli, C. et al PCT Appl. WO 02/06246). The compounds of the present invention can be synthesized according to Scheme I. In Scheme I, aryl nitrile I-1 is reacted with N-hydroxylamine I-2. The intermediate I-3 generated from this reaction can be isolated but more often is reacted in one pot with dialkyl acetylenedicaboxylate I-4 to yield the diesters I-5a or I-5b. The diesters I-5a or I-5b were converted to pyriridine carboxylate I-6 by heating at or above 120° C. in an appropriate solvent. The ester I-6 is condensed with amine I-7 to give the amide I-8. The amide coupling reaction can be carried out under a variety of conditions such as those disclosed in Jerry March, Advanced Organic Chemistry, 3$^{rd}$ edition, John Wiley & Sons, 1985.

Scheme I

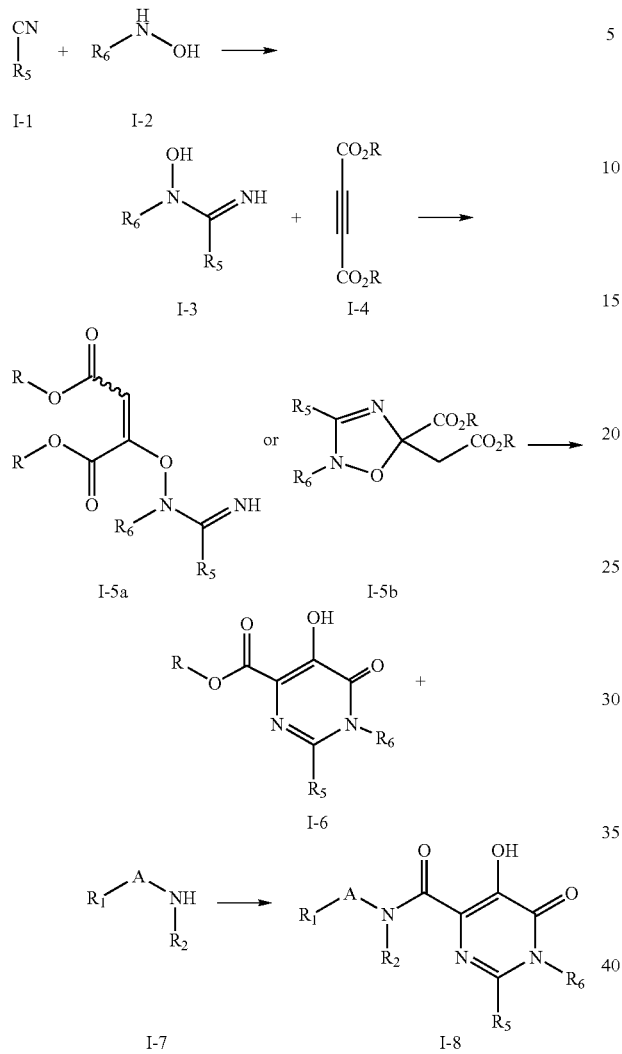

groups, R, useful for the synthesis of compounds such as 1–9 can be found in Greene, T. W. and Wutz, P. G. M. Protective Groups in Organic Synthesis, Second Edition, 1991, John Wiley and Sons, New York.

Scheme II

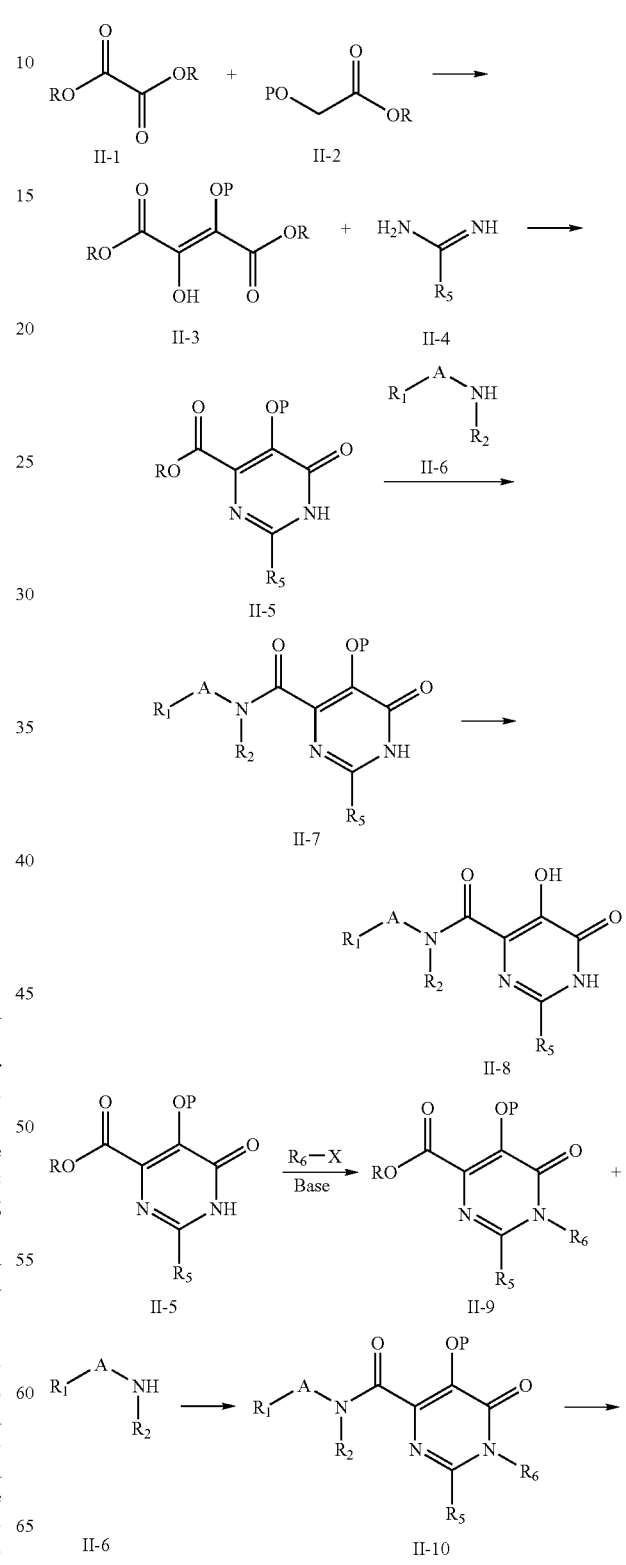

In Scheme II, an alternative pathway is shown in which the $R^6$ group is introduced at a later stage of the synthesis. Synthetic methods for the preparation of pyrimidines similar to those described in the current invention have been published (Sunderland, J. S.; et al. Inorg. Chem. (2001), 40, 6756–6756). The compounds of the present invention can be synthesized according to Scheme II. In Scheme II, an oxalic acid diester II-1 is condensed with glycolate II-2 using sodium hydride or a similar base. The intermediate II-3 generated from this reaction can be isolated but more often is reacted in one pot with an appropriately substituted amidine II-4 to yield the pyrimidinone heterocycle II-5. Intermediate II-5 is coupled with amine II-6. Alternatively, the pyrimidinone II-5 is alkylated with a suitable electrophile under basic conditions. Then intermediate II-9 is coupled with amine II-6. The amides, II-8 and II-10 are then treated under conditions appropriate for cleaving the protecting group P. For alkyl groups, where P is alkyl, this can be accomplished by $BBr_3$ or other conditions known in the art. Alternatively, when P is a benzylic or substituted benzylic group the ether can be cleaved under reductive conditions, oxidative conditions or acidic conditions. Protecting -continued

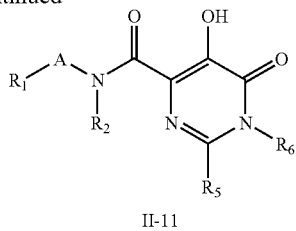

II-11

Pharmaceutical Compositions and Methods of Treatment

The compounds of this invention inhibit HIV integrase. HIV integrase inhibitors belonging to a class of diketo acid compounds prevented viral integration and inhibited HIV-1 replication in cells (Hazuda et al. Science 2000, 287, 646). Recently, HIV integrase inhibitors have been accepted into clinical trials for treating AIDS and HIV infection (Neamati Expert. Opin. Ther. Patents 2002, 12, 709, Pais and Burke Drugs Fut. 2002, 27, 1101).

Accordingly, another aspect of the invention is a method for treating HIV infection in a human patient comprising administering a therapeutically effective amount of a compound of Formula I, or a pharmaceutically acceptable salt or solvate thereof, with a pharmaceutically acceptable carrier.

Another aspect of the invention is a method for treating HIV infection in a human patient comprising administering a therapeutically effective amount of a compound of Formula I, or a pharmaceutically acceptable salt or solvate thereof, with a therapeutically effective amount of at least one other agent used for treatment of AIDS or HIV infection. Some suitable agents are nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a composition for treating HIV infection in a human patient comprising administering a therapeutically effective amount of a compound of Formula I, or a pharmaceutically acceptable salt or solvate thereof, with a pharmaceutically acceptable carrier.

"Combination," "coadministration," "concurrent," and similar terms referring to the administration of compounds of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional exipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10, mg, 100, mg, 250 mg, 500 mg, and 1000 mg. Generally, other antiretroviral agents will be present in a unit range similar to agents of that class used clinically. Typically, this 0.25–1000 mg/unit.

Liquid compositions are usually in dosage unit ranges. Generally, the liquid composition will be in a unit dosage range of 1–100 mg/mL. Some examples of dosages are 1 mg/mL, 10 mg/mL, 25, mg/mL, 50 mg/mL, and 100 mg/mL. Generally, other antiretroviral agents will be present in a unit range similar to agents of that class used clinically. Typically, this is 1–100 mg/mL.

The invention encompasses all conventional modes of administration; oral and parenteral methods are preferred. Generally, the dosing regimen will be similar to other antiretroviral agents used clinically. Typically, the daily dose will be 1–100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, Compound 1 will generally be given in a daily dose of 1–100 mg/kg body weight daily in conjunction with other agents. The other agents generally will be given in the amounts used therapeutically. The specific dosing regime, however, will be determined by a physician using sound medical judgement.

Table 1 lists some agents useful in treating AIDS and HIV infection which are suitable for this invention.

TABLE 1

| Drug Name | Manufacturer | Indication |
|---|---|---|
| ANTIVIRALS | | |
| 097 (non-nucleoside reverse transcriptase inhibitor) | Hoechst/Bayer | HIV infection, AIDS, ARC |

TABLE 1-continued

| Drug Name | Manufacturer | Indication |
|---|---|---|
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection, ARC, PGL |
| AL-721 | Ethigen (Los Angeles, CA) | HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/Novartis | HIV infection, AIDS, ARC |
| BMS-234475 (CGP-61755) (protease inhibitor) | Bristol-Myers Squibb/Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptase inhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |

TABLE 1-continued

| Drug Name | Manufacturer | Indication |
|---|---|---|
| Trizivir ® | Abbott | HIV infection, AIDS |
| Kaletra ® | Abbott | HIV infection, AIDS, ARC |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma AIDS, in combination w/AZT |
| Granulocyte Colony Stimulating Factor | Amgen | |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

In the following experimental procedures, all temperatures are understood to be in Centigrade (C) when not specified. The nuclear magnetic resonance (NMR) spectral characteristics refer to chemical shifts (δ) expressed in parts per million, (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-$d_6$ (deuterated acetone), DMSO-$d_6$ (perdeuterodimethylsulfoxide), $D_2O$ (deuterated water), $CDCl_3$ (deuterochloroform) and other conventional deuterated solvents.

The abbreviations used herein are conventional abbreviations widely employed in the art. Some of which are: calcd (calculated); DMSO (dimethylsulfoxide); EtOAc (ethyl acetate); HPLC (high-pressure liquid chromatography); LC/MS (liquid chromatography, mass spectroscopy); LDA (lithium diisopropyl amide); LiHMDS (lithium bis(trimethylsilyl)amide); $SiO_2$ (silica gel); THF (tetrahydrofuran), TFA (trifluoroacetic acid), Me (methyl), Et (ethyl), Ph (phenyl), tBuOK (potassium tert-butoxide), NaOMe (sodium methoxide), NaOEt (sodium ethoxide), Boc (tert-butoxycarbonyl), and DEAD (diethylazo dicarboxylate).

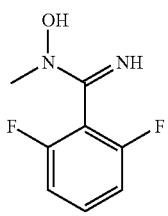

Intermediate 1

2,6-Difluoro-N-hydroxy-N-methyl-benzamidine. To a stirred solution of 2,6-difluorobenzonitrile (5.565 g, 40 mmol) and N-methylhydroxylamine hydrochloride (10 g, 120 mmol) in 4:1 water/ethanol (100 mL) was added sodium carbonate (8.5 g, 80 mmol) in small portions and the resulting mixture stirred at 100° C. for 2 h. The mixture was then cooled, concentrated and the resulting residue suspended in hot MeOH/CHCl$_3$ (1:9, 200 mL). The insoluble solids were removed by filtration and concentration of the filtrate gave the desired product as an off-white solid (7.50 g, 100% yield). $^1$HNMR (500 MHz, DMSO-d6) δ: 7.69–7.63 (1H, m), 7.29 (2H, t, J=8.24 Hz), 6.90 (2H, s), 3.15 (3H, s). LCMS calcd for $C_8H_9F_2N_2O$ (M+H): 187.07; found: 187.12.

Intermediate 2

3-(2,6-Difluoro-phenyl)-5-ethoxycarbonylmethyl-2-methyl-2,5-dihydro-[1,2,4]oxadiazole-5-carboxylic acid ethyl ester. A solution of diethyl acetylenedicarboxylate (1.60 mL, 10 mmol) and 2,6-difluoro-N-hydroxy-N-methyl-benzamidine (1.862 g, 10 mmol) in ethyl alcohol (95% yield) was heated at 80° C. for 1 h. The reaction mixture was then cooled, concentrated and purified on silica gel column eluting with 1:3, 3:7 and 2:3 ethyl acetate/hexanes to give the title compound as a yellow oil (2.691 g, 76% yield). $^1$HNMR (500 MHz, CDCl$_3$) δ: 7.48–7.42 (1H, m), 6.99 (2H, t, J=8.20 Hz), 4.37–4.24 (2H, m), 4.18 (2H, q, J=7.02 Hz), 3.40 (1H, d, J 16.48 Hz), 3.11 (1H, d, J=16.48 Hz), 3.08 (3H, s), 1.32 (3H, t, J 7.02 Hz), 1.26 (3H, t, J=7.02 Hz). LCMS calcd for $C_{16}H_{19}F_2N_2O_5$ (M+H): 357.13; found: 357.38.

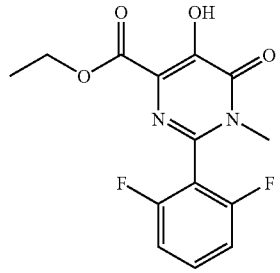

Intermediate 3

2-(2,6-Difluoro-phenyl)-5-hydroxy-1-methyl-6-oxo-1,6-dihydro-pyrimidine-4-carboxylic acid ethyl ester. A solution of 3-(2,6-difluoro-phenyl)-5-ethoxycarbonylmethyl-2-methyl-2,5-dihydro-[1,2,4]oxadiazole-5-carboxylic acid ethyl ester (2.68 g, 7.52 mmol) in xylenes (50 mL) was heated at reflux for 1.5 h and cooled to room temperature. The precipitate was filtered and dried to give the title compound as an off-white solid (1.4 g, 60% yield). $^1$HNMR (500 MHz, CDCl$_3$) δ: 10.96 (1H, s), 7.50–7.45 (1H, m), 7.04 (2H, t, J=7.33 Hz), 4.51 (2H, q, J=7.02 Hz), 3.41 (3H, s), 1.41 (3H, t, J=7.02 Hz). HRMS (ESI) calcd for $C_{14}H_{13}F_2N_2O_4$ (M+H): 311.0844; found: 311.0845.

EXAMPLE 1

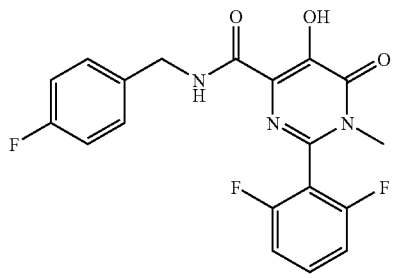

N-(4fluorobenzyl)-2-(2,6-difluorophenyl)-5-hydroxy-1-methyl-6-oxo-1,6-dihydropyrimidine-4-carboxamide. A mixture of ester 2-(2,6-difluoro-phenyl)-5-hydroxy-1-methyl-6-oxo-1,6-dihydro-pyrimidine-4-carboxylic acid ethyl ester (91 mg, 0.2933 mmol) and 4-fluorobenzylamine (184 mg, 1.5 mmol) in toluene (2 mL) was heated at reflux for 3.5 h. The reaction mixture was then, cooled, concentrated and purified by reverse phase preparative HPLC (C18, methanol/H$_2$O-0.1% TFA, gradient elution). The fractions containing the product were combined and concentrated to give the title compound as an off-white solid (55 mg, 48% yield). $^1$HNMR (500 MHz, CDCl$_3$) δ: 12.30 (1H, s), 7.80 (1H, s), 7.49 (1H, t, J=6.5 Hz), 7.34–7.22 (2H, m), 7.06–7.00 (4H, m), 4.55 (2H, d, J=5.5 Hz), 3.40 (3H, s). HRMS (ESI) calcd for $C_{19}H_{15}F_3N_3O_3$ (M+H): 390.1066; found: 390.1076.

EXAMPLE 2

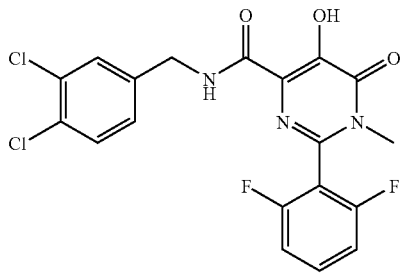

N-(3,4-dichlorobenzyl)-2-(2,6-difluorophenyl)-5-hydroxy-1-methyl-6-oxo-1,6-dihydropyrimidine-4-carboxamide. A mixture of ester 2-(2,6-difluoro-phenyl)-5-hydroxy-1-methyl-6-oxo-1,6-dihydro-pyrimidine-4-carboxylic acid ethyl ester (31 mg, 0.1 mmol) and 3,4-dichlorobenzylamine (88 mg, 0.5 mmol) in DMF (1 mL) was heated between 120–130° C. for 3 h. The reaction mixture was then cooled and purified by preparative HPLC (C18, methanol/H$_2$O-0.1% TFA, gradient elution). The fractions containing the product were combined and concentrated to give the title compound as an off-white solid (41.2 mg, 94% yield). $^1$HNMR (500 MHz, CDCl$_3$) δ: 12.15 (1H, s), 7.84 (1H, t, J=5.5 Hz), 7.53–7.47 (1H, m), 7.41–7.38 (2H, m), 7.16 (1H, dd, J=8.24, 2.13 Hz), 7.06 (1H, dd, J=8.54, 7.32 Hz), 4.53 (6.41 Hz), 3.41 (3H, s). HRMS (ESI) calcd for C$_{19}$H$_{14}$Cl$_2$F$_3$N$_3$O$_3$ (M+H): 340.0380; found: 340.0383. Anal. calcd for C$_{19}$H$_{13}$Cl$_2$F$_3$N$_3$O$_3$: C 51.83, H 2.97, N 9.54, Cl 16.10, F 8.63; found: C 51.48, H 2.63, N 9.43, Cl 15.71, F 8.52.

EXAMPLE 3

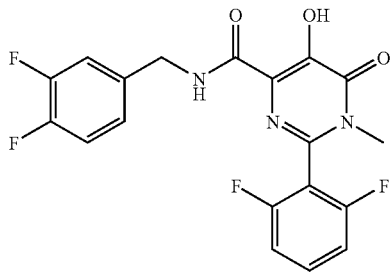

N-(3,4-difluorobenzyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydropyrimidine- 4-carboxylic acid ethyl ester (31 mg, 0.1 mmol) and 3,4-difluorobenzylamine (72 mg, 0.5 mmol). The title product was obtained as an off-white solid (32.7 mg, 80% yield). $^1$HNMR (500 MHz, CDCl$_3$) δ: 12.18 (1H, s), 7.83 (1H, br s), 7.53–7.47 (1H, m), 7.15–7.02 (5H, m), 4.53 (2H, d, J=6.41 Hz), 3.41 (3H, s). HRMS (ESI) calcd for C$_{19}$H$_{14}$F$_4$N$_3$O$_3$ (M+H): 408.0971; found: 408.0969.

EXAMPLE 4

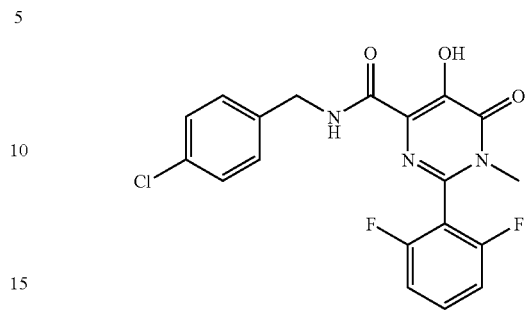

N-(4-chlorobenzyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and 4-chlorobenzylamine (71 mg, 0.5 mmol). The title product was obtained as an off-white solid (32.3 mg, 80% yield). $^1$HNMR (500 MHz, CDCl$_3$) δ: 12.25 (1H, s), 7.80 (1H, br s), 7.52–7.46 (1H, m), 7.81 (2H, d, J=8.55 Hz), 7.25 (2H, d, J=8.24 Hz), 7.05 (2H, dd, J=8.54, 7.32 Hz), 4.55 (2H, d, J=6.10 Hz), 3.41 (3H, s). HRMS (ESI) calcd for C$_{19}$H$_{15}$ClF$_2$N$_3$O$_3$ (M+H): 406.0770; found: 406.0775.

EXAMPLE 5

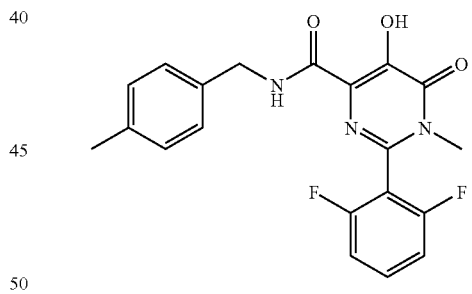

N-(4-methylbenzyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and 4-methylbenzylamine (61 mg, 0.5 mmol). The title product was obtained as an off-white solid (32 mg, 83% yield). $^1$HNMR (500 MHz, CDCl$_3$) δ: 12.39 (1H, s), 7.55 (1H, br s), 7.51–7.45 (1H, m), 7.20 (2H, d, J=7.94 Hz), 7.14 (2H, d, J=7.63 Hz), 7.03 (2H, d, J=8.55, 7.33 Hz), 4.54 (2H, d, J=6.10 Hz), 3.40 (3H, s), 2.32 (3H, s). HRMS (ESI) calcd for C$_{20}$H$_{18}$F$_2$N$_3$O$_3$ (M+H): 386.1316; found: 386.1313.

EXAMPLE 6

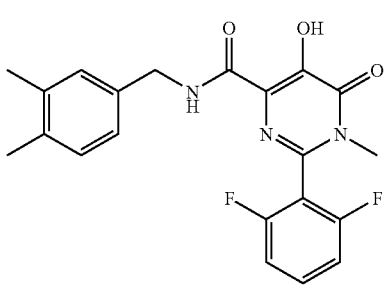

N-(3,4-dimethylbenzyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and 3,4-dimethylbenzylamine (68 mg, 0.5 mmol). The title product was obtained as an off-white solid (32.7 mg, 82% yield). $^1$HNMR (500 MHz, CDCl$_3$) δ: 12.41 (1H, s), 7.74 (1H, br s), 7.51–7.45 (1H, m), 7.10–7.02 (5H, m), 4.51 (2H, d, J=6.10 Hz), 3.40 (3H, s), 2.24 (3H, s), 2.23(3H, s). HRMS (ESI) calcd for C$_{21}$H$_{20}$F$_2$N$_3$O$_3$ (M+H): 400.1473; found: 400.01464.

EXAMPLE 7

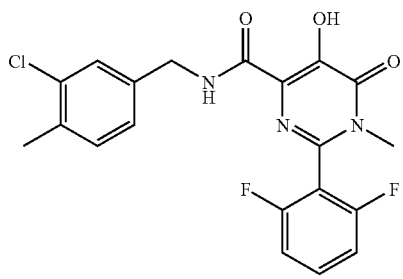

N-(3-chloro-4-methylbenzyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and 3-chloro-4-methylbenzylamine (78 mg, 0.5 mmol). The title product was obtained as an off-white solid (35.3 mg, 84% yield). $^1$HNMR (500 MHz, CDCl$_3$) δ: 12.27 (1H, s), 7.78 (1H, br s), 7.53–7.45 (1H, m), 7.31–7.03 (5H, m), 4.52 (2H, d, J=3.96 Hz), 3.41 (3H, s), 2.33 (3H, s). HRMS (ESI) calcd for C$_{20}$H$_{17}$ClF$_2$N$_3$O$_3$ (M+H): 420.0926; found: 420.0929.

EXAMPLE 8

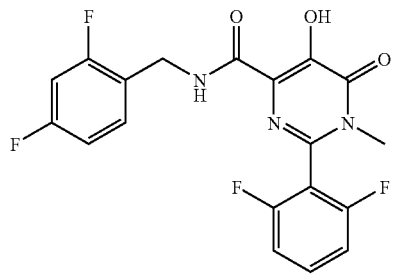

N-(2,4-difluorobenzyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and 2,4-difluorobenzylamine (72 mg, 0.5 mmol). The title product was obtained as an off-white solid (36.2 mg, 89% yield). $^1$HNMR (500 MHz, CDCl$_3$) δ: 12.13 (1H, s), 7.87 (1H, br s), 7.06 (2H, dd, J=8.54, 7.33 Hz), 6.86–6.81 (2H, m), 6.75–6.69 (2H, m), 4.56 (2H, d, J=6.41 Hz), 3.42 (3H, s). HRMS (ESI) calcd for C$_{19}$H$_{12}$F$_4$N$_3$O$_3$ (M−H): 406.0815; found: 406.0812.

EXAMPLE 9

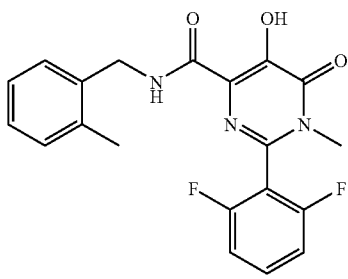

N-(2-methylbenzyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and 2-methylbenzylamine (61 mg, 0.5 mmol). The title product was obtained as an off-white solid (34.1 mg, 88.6% yield). $^1$HNMR (500 MHz, CDCl$_3$) δ: 12.38 (1H, s), 7.63 (1H, br s), 7.51–7.45 (1H, m), 7.26–7.16 (4H, m), 7.04 (2H, dd, J=8.54, 7.32 Hz), 4.59 (2H, d, J=5.79 Hz), 3.40 (3H, s), 2.33 (3H, s). HRMS (ESI) calcd for C$_{20}$H$_{16}$F$_2$N$_3$O$_3$ (M−H): 384.1160; found: 384.1171.

EXAMPLE 10

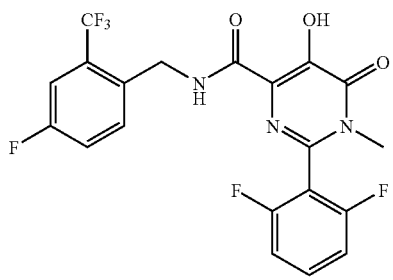

N-(4-fluoro-2-(trifluoromethyl)benzyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and 2-trifluoromethyl-4-fluorobenzylamine (97 mg, 0.5 mmol). The title product was obtained as an off-white solid (25.7 mg, 56% yield). $^1$HNMR (500 MHz, CDCl$_3$) δ: 12.07 (1H, s), 7.92 (1H, t, J=5.34), 7.53–7.47 (1H, m), 7.36 (1H, s), 7.24 (2H, d, J=8.24 Hz), 7.06 (2H, dd, J=8.54, 7.33 Hz), 4.63 (2H, d, J=6.41 Hz), 3.42 (3H, s). HRMS (ESI) calcd for C$_{20}$H$_{12}$F$_6$N$_3$O$_3$ (M−H): 456.0783; found: 456.0793.

EXAMPLE 11

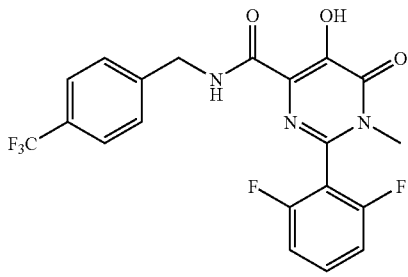

N-(4-(trifluoromethyl)benzyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and 4-trifluoromethylbenzylamine (88 mg, 0.5 mmol). The title product was obtained as an off-white solid (38.6 mg, 88% yield). $^1$HNMR (500 MHz, CDCl$_3$) δ: 12.18 (1H, s), 7.88 (1H, t, J=4.58), 7.60 (2H, d, J=8.24 Hz), 7.53–7.47 (1H, m), 7.43 (2H, d J=8.24 Hz), 7.05 (2H, dd, J=8.24, 7.32 Hz), 4.65 (2H, d, J=6.41 Hz), 3.42 (3H, s). HRMS (ESI) calcd for C$_{20}$H$_{13}$F$_5$N$_3$O$_3$ (M−H): 438.0877; found: 438.0878.

EXAMPLE 12

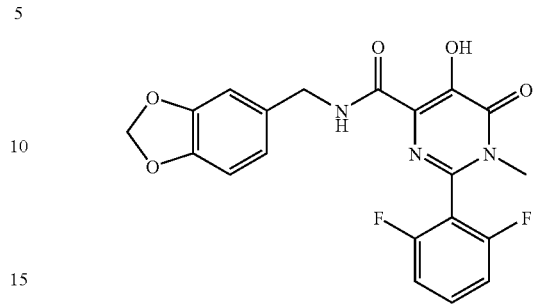

N-(benzo[d][1,3]dioxol-5-ylmethyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and piperonylamine (76 mg, 0.5 mmol). The title product was obtained as an off-white solid (18.6 mg, 45% yield). $^1$HNMR (500 MHz, CDCl$_3$) δ: 12.35 (1H, s), 7.74 (1H, br s), 7.52–7.46 (1H, m), 7.04 (2H, dd, J=8.24, 7.33 Hz), 6.80 (1H, s), 6.78–6.74 (2H, m), 5.93 (2H, s), 4.48 (2H, d, J=6.10 Hz), 3.40 (3H, s). HRMS (ESI) calcd for C$_{20}$H$_{14}$F$_2$N$_3$O$_5$ (M−H): 414.0902; found: 414.0900.

EXAMPLE 13

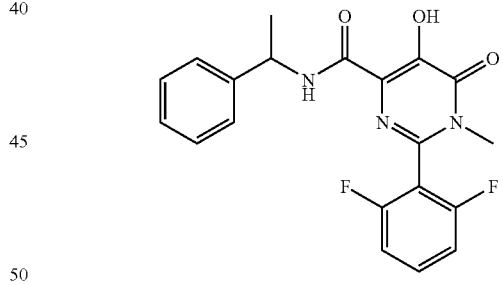

2-(2,6-difluorophenyl)-5-hydroxy-1-methyl-6-oxo-N-(1-phenylethyl)-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and α-methylbenzylamine (61 mg, 0.5 mmol). The title product was obtained as an off-white solid (24.6 mg, 64% yield). $^1$HNMR (500 MHz, CDCl$_3$) δ: 12.39 (1H, s), 7.71 (1H, d, J=7.94 Hz), 7.54–7.48 (1H, m), 7.36–7.25 (5H, m), 7.06 (2H, dd, J=14.65, 8.54 Hz), 5.22 (1H, qt, J=7.02 Hz), 3.40 (3H, s), 1.58 (3H, d, J=7.02 Hz). HRMS (ESI) calcd for C$_{20}$H$_{16}$F$_2$N$_3$O$_3$ (M−H): 384.1160; found: 384.1161.

EXAMPLE 14

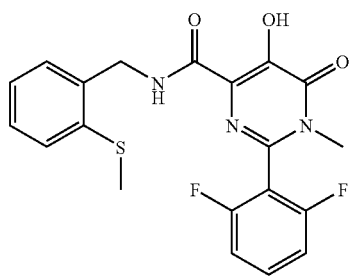

N-(2-(methylthio)benzyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and 2-methylthiobenzylamine (77 mg, 0.5 mmol). The title product was obtained as an off-white solid (34.2 mg, 82% yield). $^1$HNMR (500 MHz, CDCl$_3$) δ: 12.37 (1H, s), 7.92 (1H, br s), 7.55–7.44 (1H, m), 7.33–7.25 (2H, m), 7.17–7.14 (1H, m), 7.04 (2H, dd, J=8.24, 7.32 Hz), 4.67 (2H, d, J=6.10 Hz), 3.40 (3H, s), 2.44 (3H, s). HRMS (ESI) calcd for C$_{20}$H$_{16}$F$_2$N$_3$O$_3$S (M−H): 416.0880; found: 416.0879.

EXAMPLE 15

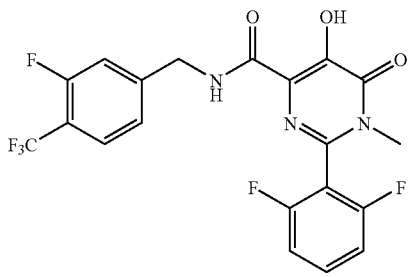

N-(3-fluoro-4-(trifluoromethyl)benzyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and 3-fluoro-4-trifluoromethylbenzylamine (97 mg, 0.5 mmol). The title product was obtained as an off-white solid (44.7 mg, 98% yield). $^1$HNMR (500 MHz, CDCl$_3$) δ: 12.13 (1H, s), 7.88 (1H, br s), 7.57–7.47 (4H, m), 7.06 (2H, dd, J=8.54, 7.32 Hz), 4.59 (2H, d, J=6.41 Hz), 3.41 (3H, s). HRMS (ESI) calcd for C$_{20}$H$_{12}$F$_6$N$_3$O$_3$ (M−H): 456.0782; found: 456.0788.

EXAMPLE 16

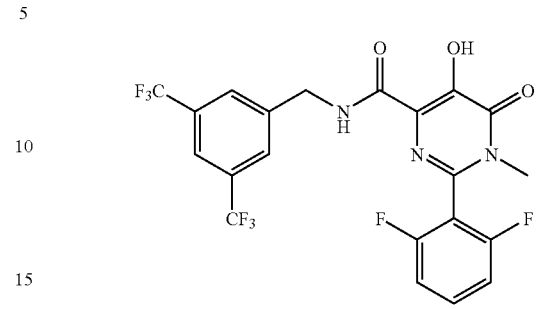

N-(3,5-bis(trifluoromethyl)benzyl)-2-(2,6-difluorophenyl)-5-hydroxy-1-methyl-6-oxo-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and 2,5-ditrifluoromethyl-benzylamine (98 mg, 0.5 mmol). The title product was obtained as an off-white solid (43.6 mg, 86% yield). $^1$HNMR (500 MHz, CDCl$_3$) δ: 12.01 (1H, s), 7.98 (1H, t, J=5.5 Hz), 7.80 (1H, s), 7.77 (2H, s), 7.54–7.47 (1H, m), 7.06 (2H, dd, J=8.54, 7.32 Hz), 4.70 (2H, d, J=6.41 Hz), 3.42 (3H, s). HRMS (ESI) calcd for C$_{21}$H$_{12}$F$_8$N$_3$O$_3$ (M−H): 506.0751; found: 506.0762.

EXAMPLE 17

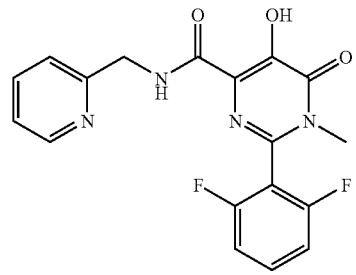

2-(2,6-difluorophenyl)-5-hydroxy-1-methyl-6-oxo-N-(pyridin-2-ylmethyl)-1,6-dihydropyrimidine-4-carboxamide. Prepared according to the procedure described for example 2 from 2-(2,6-difluoro-phenyl)-5-hydroxy-1-methyl-6-oxo-1,6-dihydro-pyrimidine-4-carboxylic acid ethyl ester (31 mg, 0.1 mmol) and 2-(aminomethyl)pyridine (54 mg, 0.5 mmol). The title product was obtained as a TFA salt, white solid (11 mg, 23% yield). $^1$HNMR (500 MHz, CDCl$_3$) δ: 12.00–10.00 (2H, br s), 8.73 (1H, t, J=5.49 Hz), 8.67 (1H, d, J=4.88 Hz), 8.19 (1H, t, J=7.78 Hz), 7.87 (1H, d, J=7.94 Hz), 7.66 (1H, t, J=6.56 Hz), 7.53–7.47 (1H, m), 7.05 (2H, dd, J=8.54, 7.32 Hz), 4.97 (2H, d, J=6.41 Hz), 3.40 (3H, s). HRMS (ESI) calcd for C$_{18}$H$_{15}$F$_2$N$_4$O$_3$ (M+H): 373.1112; found: 373.1119.

EXAMPLE 18

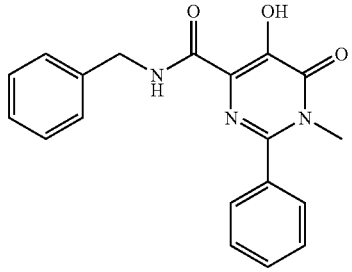

N-benzyl-5-hydroxy-1-methyl-6-oxo-2-phenyl-1,6-dihydropyrimidine-4-carboxamide. Prepared according to the procedure described for example 2 from 2-(2,6-difluorophenyl)-5-hydroxy-1-methyl-6-oxo-1,6-dihydro-pyrimidine-4-carboxylic acid ethyl ester (62 mg, 0.2 mmol) and benzylamine (64 mg, 0.6 mmol). The title product was obtained as a white solid (45 mg, 61% yield). $^1$HNMR (500 MHz, CDCl$_3$) δ:). 12.38 (1H, s), 7.82 (1H, br s), 7.53–7.47 (1H, m), 7.37–7.29 (5H, m), 7.25–7.26 (2H, m), 7.07–7.04 (2H, m), 4.60 (2H, d, J=5.8 Hz), 3.42 (3H, s). HRMS calcd for $C_{19}H_{16}F_2N_3O_3$ (M+H): 372.1160; found: 372.1156. Anal. Cald for $C_{19}H_{15}F_2N_3O_3$: C, 61.45, H, 4.07; N, 11.31; found: C, 61.12, H, 3.77; N, 11.06

Intermediate 4

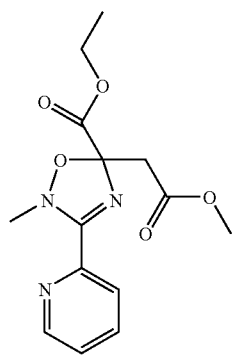

5-Methoxycarbonylmethyl-2-methyl-3-pyridin-2-yl-2,5-dihydro-[1,2,4]oxadiazole-5-carboxylic acid ethyl ester. To a stirred solution of 2-cyanopyridine (2.08 g, 20 mmol) and N-methylhydroxylamine hydrochloride (1.66 g, 20 mmol) in 1:1 water/ethanol (30 mL) was added sodium carbonate (1.04 g, 10 mmol) in small portions. LCMS analysis after 5 min indicated that the reaction was complete. To this was added diethyl acetylenedicarboxylate (3.2 mL, 20 mmol) and the reaction mixture stirred for additional 20 min at room temperature. LCMS analysis of the resulting dark-green reaction showed that the reaction was complete. The reaction mixture was taken up into ethyl acetate (200 mL) and washed successively with water (2×25 mL) and brine (25 mL), and the organic layer dried (Na2SO4), filtered and concentrated to give brown oil which was passed through a plug of silica gel (1:1 hexanes/ethyl acetate). The filtrate was concentrated to give the title compound as a yellow oil (6.87 g). LCMS calcd for $C_{15}H_{20}N_3O_5$ (M+H): 322.14; found: 322.08.

Intermediate 5

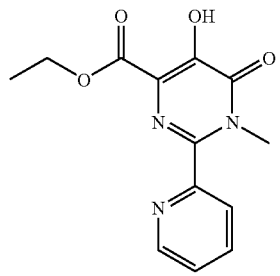

5-Hydroxy-1-methyl-6-oxo-2-pyridin-2-yl-1,6-dihydropyrimidine-4-carboxylic acid ethyl ester. A solution of 5-methoxycarbonylmethyl-2-methyl-3-pyridin-2-yl-2,5-dihydro-[1,2,4]oxadiazole-5-carboxylic acid ethyl ester in xylenes (40 mL) was heated at reflux for 1 h. The reaction mixture was cooled and purified on silica gel column (CH$_2$Cl$_2$/5–20% methanol). The fractions containing the product were combined and concentrated to give the title compound as a brown powder (0.705 g, 12.8% yield). $^1$HNMR (500 MHz, CDCl$_3$) δ: 10.75 (1H, br s), 8,66 (1H, d, J=4.89 Hz), 7.87 (1H, td, J=7.7, 1.5 Hz), 7.80 (1H, d, J=7.94 Hz), 7.42–7.39 (1H, m), 4.49 (2H, q, J=7.02 Hz), 3.63 (3H, s), 1.43 (3H, s). HRMS (ESI) calcd for $C_{13}H_{14}N_3O_4$ (M+H): 276.098465; found: 276.0995.

EXAMPLE 19

N-(4-chlorobenzyl)-5-hydroxy-1-methyl-6-oxo-2-(pyridin-2-yl)-1,6-dihydropyrimidine-4-carboxamide. Prepared according to the procedure described for example 2 from 5-hydroxy-1-methyl-6-oxo-2-pyridin-2-yl-1,6-dihydro-pyrimidine-4-carboxylic acid ethyl ester (27.53 mg, 0.1 mmol) and 4-chlorobenzylamine (71 mg, 0.5 mmol). The title product was obtained as a TFA salt (brown solid, 10.3 mg, 21% yield). $^1$HNMR (500 MHz, CDCl$_3$) δ: 12.19 (1H, s), 8.70 (1H, d, J=4.28 Hz), 7.91 (1H, br s), 7.87 (1H, t, J=6.41 Hz), 7.66 (1H, t, J=7.63 Hz), 7.44 (1H, dd, J=7.48, 5.04 Hz), 7.31–7.24 (4H, m), 4.57 (2H, d, J=6.41 Hz), 3.59 (3H, s). HRMS (ESI) calcd for $C_{18}H_{16}ClN_4O_3$ (M+H): 371.0911; found: 371.0912.

EXAMPLE 20

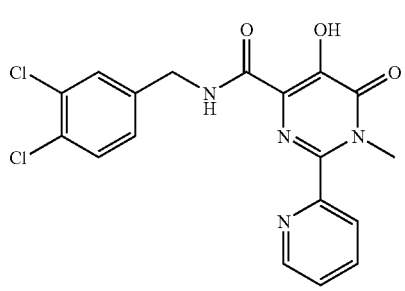

N-(3,4-dichlorobenzyl)-5-hydroxy-1-methyl-6-oxo-2-(pyridin-2-yl)-1,6-dihydropyrimidine-4-carboxamide. Prepared according to the procedure described for example 2 from 5-hydroxy-1-methyl-6-oxo-2-pyridin-2-yl-1,6-dihydro-pyrimidine-4-carboxylic acid ethyl ester (27.53 mg, 0.1 mmol) and 3,4-dichlorobenzylamine (71 mg, 0.5 mmol). The title product was obtained as a TFA salt (off-white solid, 18.6 mg, 36% yield). $^1$HNMR (500 MHz, CDCl$_3$) δ: 12.17 (1H, s), 8.71 (1H, d, J=3.97 Hz), 7.92 (1H, br s), 7.90 (1H, t, J=7.63 Hz), 7.68 (1, d, J=7.63 Hz), 7.46 (1H, dd, J=7.37, 5.18 Hz), 7.41–7.39 (2H, m), 7.16 (1H, dd, J=8.39, 1.98 Hz), 4.55 (2H, d, J=6.41 Hz), 3.59 (3H, s). HRMS (ESI) calcd for C$_{18}$H$_{15}$Cl$_2$N$_4$O$_3$ (M+H): 405.0521; found: 405.0515.

EXAMPLE 21

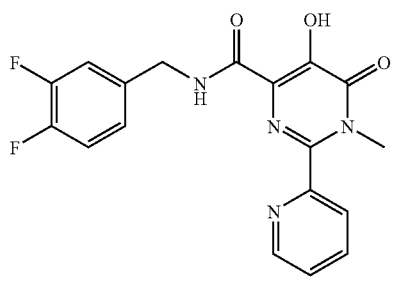

N-(3,4-difluorobenzyl)-5-hydroxy-1-methyl-6-oxo-2-(pyridin-2-yl)-1,6-dihydropyrimidine-4-carboxamide. Prepared according to the procedure described for example 2 from 5-hydroxy-1-methyl-6-oxo-2-pyridin-2-yl-1,6-dihydro-pyrimidine-4-carboxylic acid ethyl ester (27.53 mg, 0.1 mmol) and 3,4-difluorobenzylamine (72 mg, 0.5 mmol). The title product was obtained as a TFA salt (brown solid, 11.2 mg, 23% yield). $^1$HNMR (500 MHz, CDCl$_3$) δ: 12.18 (1H, s), 8.72 (1H, d, J=4.88 Hz), 8.02 (1H, br s), 7.91 (1H, td, J=1.63, 7.78 Hz), 7.69 (1H, d, J=7.63 Hz), 7.48 (1H, dd, J=7.63, 4.88 Hz), 7.17–7.03 (3H, m), 4.55 (2H, d, J=6.41 Hz), 3.60 (3H, s). HRMS (ESI) calcd for C$_{18}$H$_{15}$F$_2$N$_4$O$_3$ (M+H): 373.1112; found: 373.1117.

EXAMPLE 22

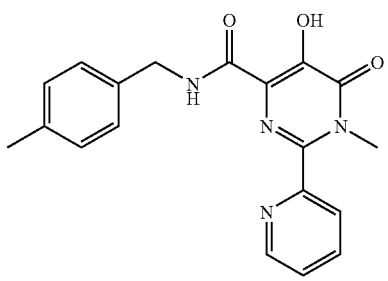

N-(4-methylbenzyl)-5-hydroxy-1-methyl-6-oxo-2-(pyridin-2-yl)-1,6-dihydropyrimidine-4-carboxamide. Prepared according to the procedure described for example 2 from 5-hydroxy-1-methyl-6-oxo-2-pyridin-2-yl-1,6-dihydro-pyrimidine-4-carboxylic acid ethyl ester (27.53 mg, 0.1 mmol) and 4-methylbenzylamine (61 mg, 0.5 mmol). The title product was obtained as a TFA salt (brown solid, 14.3 mg, 31% yield). $^1$HNMR (500 MHz, CDCl$_3$) δ: 12.37 (1H, s), 8.70 (1H, d, J=4.58 Hz), 7.91–7.85 (2H, m), 7.66 (1H, d, J=7.94 Hz), 7.44 (1H, dd, J=7.02, 4.88 Hz), 7.21 (2H, d, J=7.93 Hz), 7.15 (1H, d, J=7.93 Hz), 4.56 (2H, J=6.11 Hz), 3.59 (3H, s), 2.32 (3H, s). HRMS (ESI) calcd for C$_{19}$H$_{19}$N$_4$O$_3$ (M+H): 351.1457; found: 351.1471.

EXAMPLE 23

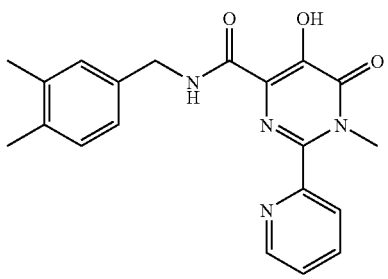

N-(3,4-dimethylbenzyl)-5-hydroxy-1-methyl-6-oxo-2-(pyridin-2-yl)-1,6-dihydropyrimidine-4-carboxamide. Prepared according to the procedure described for example 2 from 5-hydroxy-1-methyl-6-oxo-2-pyridin-2-yl-1,6-dihydro-pyrimidine-4-carboxylic acid ethyl ester (27.53 mg, 0.1 mmol) and 3,4-dimethylbenzylamine (68 mg, 0.5 mmol). The title product was obtained as a TFA salt (brown solid, 14.1 mg, 30% yield). $^1$HNMR (500 MHz, CDCl$_3$) δ: 12.36 (1H, s), 8.69 (1H, d, J=3.97 Hz), 7.88–7.85 (2H, m), 7.66 (1H, d, J=7.94 Hz), 7.43 (1H, dd, J=6.71, 4.88 Hz), 7.10–7.03 (3H, m), 4.53 (2H, d, J=6.10 Hz), 3.59 (3H, s), 2.24 (3H, s), 2.23 (3H, s). HRMS (ESI) calcd for C$_{20}$H$_{21}$N$_4$O$_3$ (M+H): 365.1614; found: 365.1617.

EXAMPLE 24

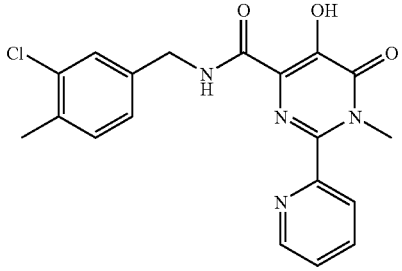

N-(3-chloro-4-methylbenzyl)-5-hydroxy-1-methyl-6-oxo-2-(pyridin-2-yl)-1,6-dihydropyrimidine-4-carboxamide. Prepared according to the procedure described for example 2 from 5-hydroxy-1-methyl-6-oxo-2-pyridin-2-yl-1,6-dihydro-pyrimidine-4-carboxylic acid ethyl ester (27.53 mg, 0.1 mmol) and 3-chloro-4-methylbenzylamine (78 mg, 0.5 mmol). The title product was obtained as a TFA salt (brown solid, 7.2 mg, 14% yield). $^1$HNMR (500 MHz, CDCl$_3$) δ: 12.23 (1H, s), 8.72 (1H, d, J=4.27 Hz), 7.92 (1H, br s), 7.91 (1H, t, J=7.18 Hz), 7.69 (1H, d, J=7.63 Hz), 7.47 (1H, dd, J=7.47, 5.04 Hz), 7.29 (1H, s), 7.19 (1H, d, J=7.63 Hz), 7.11 (1H, d, J=7.93 Hz), 4.54 (2H, d, J=6.11 Hz), 3.60 (3H, s), 2.34 (3H, s). HRMS (ESI) calcd for $C_{19}H_{18}ClN_4O_3$ (M+H): 385.1068; found: 385.1076.

EXAMPLE 25

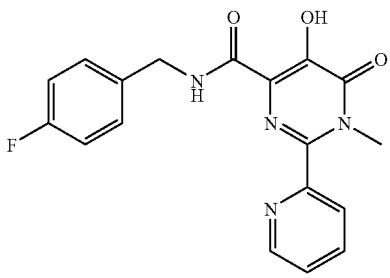

N-(4-fluorobenzyl)-5-hydroxy-1-methyl-6-oxo-2-(pyridin-2-yl)-1,6-dihydropyrimidine-4-carboxamide. A mixture of 5-hydroxy-1-methyl-6-oxo-2-pyridin-2-yl-1,6-dihydro-pyrimidine-4-carboxylic acid ethyl ester (27.53 mg, 0.1 mmol) and 4-fluorobenzylamine (63 mg, 0.5 mmol) in toluene (2 mL) was heated at reflux for 6 h then cooled, concentrated and purified by preparative HPLC (C18, methanol/H$_2$O-0.1% TFA, gradient elution). The fractions containing the product were combined and concentrated to give the title compound as a TFA salt (brown paste, 9.6 mg, 21% yield). $^1$HNMR (500 MHz, CDCl$_3$) δ: 12.52–12.30 (1H, br s), 8.71 (1H, d, J=4.27 Hz), 7.90–7.84 (2H, m), 7.66 (1H, d, J=7.63 Hz), 7.45 (1H, td, J=7.63, 4.88 Hz), 7.30–7.27 (2H, m), 7.05–7.00 (2H, m), 4.57 (2H, d, J=6.10 Hz), 3.58 (3H, s). HRMS (ESI) calcd for $C_{18}H_{16}FN_4O_3$ (M+H): 355.1207; found: 355.1215.

Intermediate 6

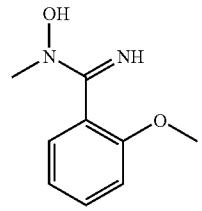

N-Hydroxy-2-methoxy-N-methyl-benzamidine. To a stirred solution of 2-methoxybenzonitrile (2.66 g, 20 mmol) and N-methylhydroxylamine hydrochloride (3.341 g, 40 mmol) in 2:1 water/ethanol (30 mL) was added sodium carbonate (2.332 g, 22 mmol) in small portions and the resulting pink solution stirred at 80° C. for 28 h. The reaction mixture was then concentrated and the residue stirred with CH$_2$Cl$_2$, filtered and concentrated to give crude product as a purple solid (3.3 g), which was used in the next step without further purification.

Intermediate 7

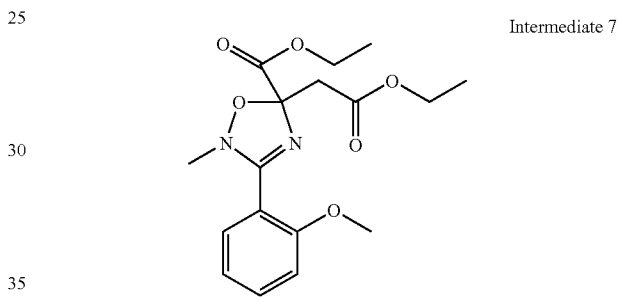

5-Ethoxycarbonylmethyl-3-(2-methoxy-phenyl)-2-methyl-2,5-dihydro-[1,2,4]oxadiazole-5-carboxylic acid ethyl ester. To a stirred solution of N-hydroxy-2-methoxy-N-methyl-benzamidine (3.3 g) in ethanol (100%) was added diethyl acetylenedicarboxylate (3.2 mL, 20 mmol) and the resulting mixture stirred for 2 h at room temperature. The reaction mixture was then concentrated and purified on silica gel column using (3:7 to 2:3 ethyl acetate/hexanes) to afford the title product as a yellow oil (4.93 g, 70% yield). $^1$HNMR (500 MHz, CDCl$_3$) δ: 7.56 (1H, dd, 7.6, 1.5 Hz), 7.44 (1H, td, J=7.6, 1.6 Hz), 6.99 (1H, t, 7.5 Hz), 6.95 (1H, d, J=8.2 Hz), 4.36–4.10 (4H, m), 3.85 (3H, s), 3.43 (1H, d, J=16.48 Hz), 3.05 (3H, s), 3.04 (1H, d, J=16.48 Hz), 1.32 (3H, t, J=7.02 Hz), 1.25 (3H, t, J=7.02 Hz). HRMS (ESI) calcd for $C_{17}H_{23}N_2O_6$ (M+H): 351.1556; found: 351.1553.

Intermediate 8

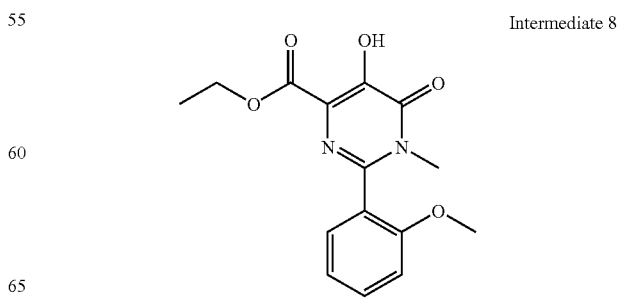

5-Hydroxy-2-(2-methoxy-phenyl)-1-methyl-6-oxo-1,6-dihydro-pyrimidine-4-carboxylic acid ethyl ester. A solution of 5-ethoxycarbonylmethyl-3-(2-methoxy-phenyl)-2-methyl-2,5-dihydro-[1,2,4]oxadiazole-5-carboxylic acid ethyl ester (4.916 g, 14.03 mmol) in xylenes (30 mL) was heated at reflux for 3 h, cooled to room temperature and diluted with hexanes (30 mL). The resulting mixture was left in the refrigerator (5° C.) for 48 h. The liquid was decanted and dried to give the title product as a red solid (1.813 g, 43% yield). $^1$HNMR (500 MHz, CDCl$_3$) δ: 10.76 (1H, s), 7.45 (1H, td, J=7.33, 1.53 Hz), 7.34 (1H, d, J=7.32 Hz), 7.06 (1H, t, J=7.32 Hz), 6.94 (1H, d, J=8.55 Hz), 4.55–4.41 (2H, m), 3.79 (3H, s), 3.34 (3H, s), 1.40 (3H, t, J=7.02 Hz). HRMS (ESI) calcd for C$_{15}$H$_{15}$N$_2$O$_5$ (M+H): 303.0981; found: 303.0980.

EXAMPLE 26

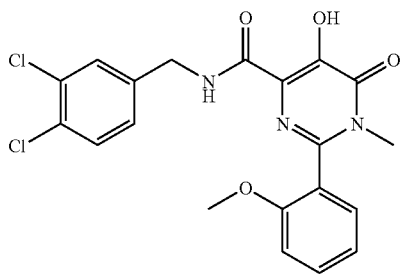

N-(3,4-dichlorobenzyl)-5-hydroxy-2-(2-methoxyphenyl)-1-methyl-6-oxo-1,6-dihydropyrimidine-4-carboxamide. Prepared according to the procedure described for example 2 from 5-Hydroxy-2-(2-methoxy-phenyl)-1-methyl-6-oxo-1,6-dihydro-pyrimidine-4-carboxylic acid ethyl ester (45.6 mg, 0.15 mmol) and 3,4-dichlorobenzylamine (132 mg, 0.75 mmol). The title product was obtained as a pink solid (55.5 mg, 85% yield). $^1$HNMR (500 MHz, CDCl$_3$) δ: 11.98 (1H, s), 7.95 (1H, t, J=5.19 Hz), 7.49 (1H, td, J=7.33, 1.83 Hz),7.40–7.38 (2H, m), 7.29 (1H, dd, J=7.63, 1.83 Hz), 7.15 (1H, dd, J=8.24, 1.83 Hz), 7.07 (1H, t, J=8.24 Hz), 4.51 (2H, d, J=6.41 Hz), 3.82 (3H, s), 3.35 (3H, s). HRMS (ESI) calcd for C$_{20}$H$_{18}$Cl$_2$N$_3$O$_4$ (M+H): 434.0675; found: 434.0674.

EXAMPLE 27

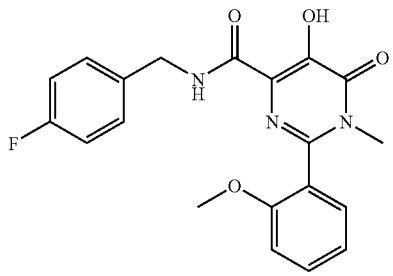

N-(4-fluorobenzyl)-5-hydroxy-2-(2-methoxyphenyl)-1-methyl-6-oxo-1,6-dihydropyrimidine-4-carboxamide. Prepared according to the procedure described for example 2 from 5-hydroxy-2-(2-methoxy-phenyl)-1-methyl-6-oxo-1,6-dihydro-pyrimidine-4-carboxylic acid ethyl ester (45.6 mg, 0.15 mmol) and 4-fluorobenzylamine (95 mg, 0.75 mmol). The title product was obtained as a pink solid (37 mg, 64% yield). $^1$HNMR (500 MHz, CDCl$_3$) δ: 12.13 (1H, s), 7.90 (1H, t, J=5.50 Hz), 7.48 (1H, td, J=7.02, 1.83 Hz), 7.29–7.26 (3H, m), 7.06 (1H, t, J=7.33 Hz), 7.02–6.97 (3H, m),4.53 (2H, d, J=6.41 Hz), 3.81 (3H, s), 3.34 (3H, s). HRMS (ESI) calcd for C$_{20}$H$_{19}$FN$_3$O$_4$ (M+H): 384.1360; found: 384.1370.

EXAMPLE 28

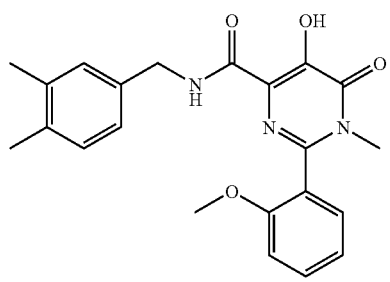

N-(3,4-dimethylbenzyl)-5-hydroxy-2-(2-methoxyphenyl)-1-methyl-6-oxo-1,6-dihydropyrimidine-4-carboxamide. Prepared according to the procedure described for example 2 from 5-hydroxy-2-(2-methoxy-phenyl)-1-methyl-6-oxo-1,6-dihydro-pyrimidine-4-carboxylic acid ethyl ester (45.6 mg, 0.15 mmol) and 3,4-dimethylbenzylamine (102 mg, 0.75 mmol). The title product was obtained as a brown solid (53.5 mg, 91% yield). $^1$HNMR (500 MHz, CDCl$_3$) δ: 12.50–11.95 (1H, br s), 7.85 (1H, t, J=4.58 Hz), 7.47 (1H, td, J=8.24, 1.83 Hz), 7.27 (1H, dd, J=17.63, 0.83 Hz), 7.09–7.02 (4H, m), 6.97 (1H, d, J=8.24 Hz), 4.49 (2H, d, J=5.79 Hz), 3.81 (3H, s), 3.34 (3H, s) 2.23 (3H, s), 2.22 (3H, s). HRMS (ESI) calcd for C$_{22}$H$_{24}$N$_3$O$_4$ (M+H): 394.1767; found: 394.1781.

EXAMPLE 29

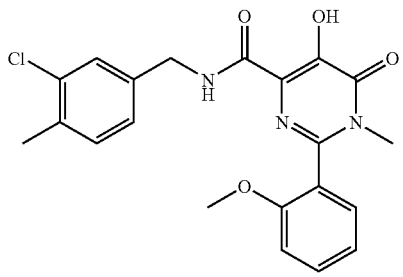

N-(3-chloro-4-methylbenzyl)-5-hydroxy-2-(2-methoxyphenyl)-1-methyl-6-oxo-1,6-dihydropyrimidine-4-carboxamide. Prepared according to the procedure described for example 2 from 5-hydroxy-2-(2-methoxy-phenyl)-1-methyl-6-oxo-1,6-dihydro-pyrimidine-4-carboxylic acid ethyl ester (45.6 mg, 0.15 mmol) and 3-chloro-4-methylbenzylamine (107 mg, 0.75 mmol). The title product was obtained as a brown solid (57.5 mg, 93% yield). $^1$HNMR (500 MHz, CDCl$_3$) δ: 12.04 (1H, br s), 7.90 (1H, t, J=5.49 Hz), 7.48 (1H, td, J=8.24, 1.83 Hz), 7.30–7.25 (2H, m), 7.17 (1H, d, J=7.94 Hz), 7.10–7.05 (2H, m), 6.98 (1H, d, J=8.55 Hz), 4.50 (2H, d, J 6.41 Hz), 3.82 (3H, s), 3.34 (3H, s), 2.34 (3H, s). HRMS (ESI) calcd for $C_{21}H_{21}ClN_3O_4$ (M+H): 414.1221; found: 414.1234.

Intermediate 9

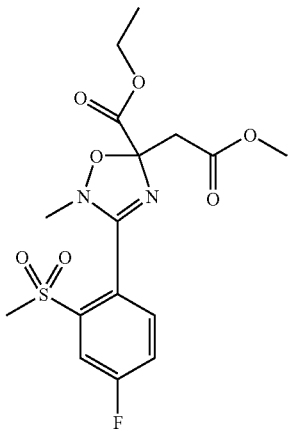

5-Ethoxycarbonylmethyl-3-(4-fluoro-2-methanesulfonyl-phenyl)-2-methyl-2,5-dihydro-[1,2,4]oxadiazole-5-carboxylic acid ethyl ester. To a stirred suspension of 4-fluoro-2-(methylsulfonyl)benzonitrile (prepared according to the procedure described in Anthonyl, N. J. et al PCT Appl. WO 02/30931, 2002) (2.2 g, 11 mmol) and N-methylhydroxy-lamine hydrochloride (1.66 g, 20 mmol) in 1:1 water/ethanol (40 mL) was added sodium carbonate (1.06 g, 10 mmol) in small portions and the resulting mixture stirred at 80° C. for 3 h. The reaction mixture was concentrated and the residue was re-dissolved into 1:1 water :ethanol (50 mL). To this solution was added diethyl acetylene-dicarboxylate (1.92 mL, 12 mmol) and the resulting mixture stirred for 30 min at room temperature. The reaction mixture was then taken-up into ethyl acetate (150 mL), washed successively with water and brine (50 mL each), dried (MgSO4), filtered and concentrated to give yellow oil. The crude product was purified on silica gel column (3:7 to 2:3 ethyl acetate/hexanes) to afford the title product as a white solid (2.9122 g, 64% yield). $^1$HNMR (500 MHz, CDCl$_3$) δ: 7.89 (1H, dd, J=8.09, 2.59 Hz), 7.62 (1H, dd, J=8.39, 5.04 Hz), 7.40 (1H, td, J=8.24, 2.44 Hz), 4.35–4.26 (2H, m), 4.19–4.13 (2H, m), 3.40 (3H, s), 3.38 (1H, d, J=16.17 Hz), 3.15 (1H, d, J=16.17 Hz), 3.02 (3H, s), 1.36–1.30 (3H, m), 1.27–1.23 (3H, m). HRMS (ESI) calcd for $C_{17}H_{22}FN_2O_7S$ (M+H): 417.1132; found: 417.1116.

Intermediate 10

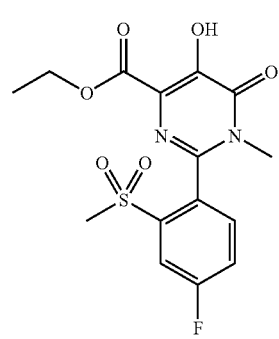

2-(4-Fluoro-2-methanesulfonyl-phenyl)-5-hydroxy-J-methyl-6-oxo-1,6-dihydro-pyrimidine-4-carboxylic acid ethyl ester. A solution of 5-ethoxycarbonylmethyl-3-(4-fluoro-2-methanesulfonyl-phenyl)-2-methyl-2,5-dihydro-[1,2,4]oxadiazole-5-carboxylic acid ethyl ester (2.91 g, 6.988 mmol) in xylenes (30 mL) was placed in pre-heated oil bath and refluxed for 6 h,. Heating was stopped and the reaction mixture was allowed to cool slowly to room temperature. The precipitated product was separated by decanting the solvent, rinsed with ether and dried to give the title compound as a yellow solid (1.2192 g, 47% yield). $^1$HNMR (500 MHz, CDCl$_3$) δ: 10.57 (1H, s), 7.90 (1H, dd, J=7.93, 2.44 Hz), 7.49–7.42 (2H, m), 4.54–4.47 (1H, m), 4.41–4.34 (1H, m), 3.31 (3H, s), 3.30 (3H, s), 1.35 (3H, t, J=7.02 Hz). HRMS (ESI) calcd for $C_{15}H_{16}FN_2O_6S$ (M+H): 371.0713; found: 371.0724.

EXAMPLE 30

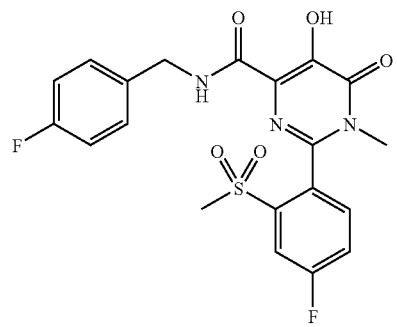

N-(4fluorobenzyl)-2-(4-fluoro-2-(methylsulfonyl)phe-nyl)-5-hydroxy-1-methyl-6-oxo-1,6-dihydropyrimidine-4-carboxamide. Prepared according to the procedure described for example 2 from 2-(4-fluoro-2-methanesulfonyl-phenyl)-5-hydroxy-1-methyl-6-oxo-1,6-dihydro-pyrimidine-4-carboxylic acid ethyl ester (55.56 mg, 0.15 mmol) and 4-fluo-robenzylamine (125 mg, 1.0 mmol). The title product was obtained as a white solid (61 mg, 68% yield). $^1$HNMR (500 MHz, CDCl$_3$) δ: 12.16 (1H, s), 7.87 (1H, dd, J=7.78, 2.59 Hz), 7.53 (1H, t, J 5.50 Hz), 7.48 (1H, td, J=7.86, 2.65 Hz), 7.41 (1H, dd, J=8.54, 4.88 Hz), 7.23 (2H, dd, J=8.55, 5.50 Hz), 7.00 (2H, t, J=8.54 Hz), 4.55 (1H, dd, J=14.95, 6.40 Hz), 4.51 (1H, dd, J=14.95, 6.10 Hz), 3.26 (3H, s), 3.01 (3H, s). HRMS (ESI) calcd for $C_{20}H_{18}F_2N_3O_5S$ (M+H): 450.0935; found: 450.0941.

EXAMPLE 31

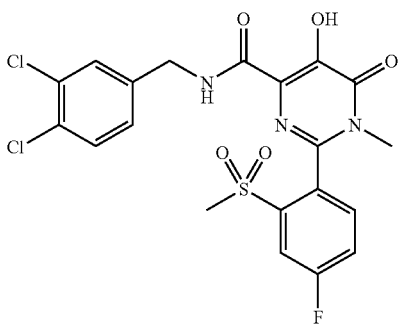

N-(3,4-dichlorobenzyl)-2-(4-fluoro-2-(methylsulfonyl)phenyl)-5-hydroxy-1-methyl-6-oxo-1,6-dihydropyrimidine-4-carboxamide. Prepared according to the procedure described for example 2 from 2-(4-fluoro-2-methanesulfonyl-phenyl)-5-hydroxy-1-methyl- 6-oxo-1,6-dihydro-pyrimidine-4-carboxylic acid ethyl ester (74.07 mg, 0.20 mmol) and 3,4-dichlorobenzylamine (132 mg, 0.75 mmol). The title product was obtained as a pink solid (69 mg, 92% yield). $^1$HNMR (500 MHz, CDCl$_3$) δ: 12.00 (1H, s), 7.87 (1H, dd, J=7.63, 2.45 Hz), 7.60 (1H, t, J=7.60 Hz), 7.50–7.42 (2H, m), 7.39 (1H, d, J=7.93 Hz), 7.32 (1H, s), 7.11 (1H, d, J=7.32 Hz), 4.55 (1H, dd, J=15.26, 6.41 Hz), 4.49 (1H, dd, J=15.26, 6.10 Hz), 3.26 (3H, s), 3.06 (3H, s). HRMS (ESI) calcd for C$_{20}$H$_{17}$Cl$_2$FN$_3$O$_5$S (M+H): 500.0250; found: 500.0259.

EXAMPLE 32

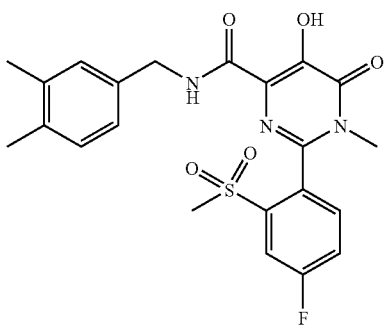

N-(3,4-dimethylbenzyl)-2-(4-fluoro-2-(methylsulfonyl)phenyl)-5-hydroxy-1-methyl-6-oxo-1,6-dihydropyrimidine-4-carboxamide. Prepared according to the procedure described for example 2 from 2-(4-fluoro-2-methanesulfonyl-phenyl)-5-hydroxy-1-methyl-6-oxo-1,6-dihydro-pyrimidine-4-carboxylic acid ethyl ester (55.56 mg, 0.15 mmol) and 3,4-dimethylbenzylamine (102 mg, 0.75 mmol). The title product was obtained as a pink solid (59.8 mg, 87% yield). $^1$HNMR (500 MHz, CDCl$_3$) δ: 12.25 (1H, s), 7.86 (1H, dd, J=7.63, 2.44 Hz), 7.49–7.44 (2H, m), 7.41 (1H, dd, J=8.54, 4.88 Hz), 7.07 (1H, d, J=7.63 Hz), 7.01 (1H, s), 6.97 (1H, d, J=7.63 Hz), 4.53 (1H, dd, J=14.65, 6.41 Hz), 4.43 (1H, dd, J=14.96, 5.49 Hz), 3.26 (3H, s), 3.01 (3H, s), 2.22 (6H, s). HRMS (ESI) calcd for C$_{22}$H$_{23}$FN$_3$O$_5$S (M+H): 460.1343; found: 460.1337.

EXAMPLE 33

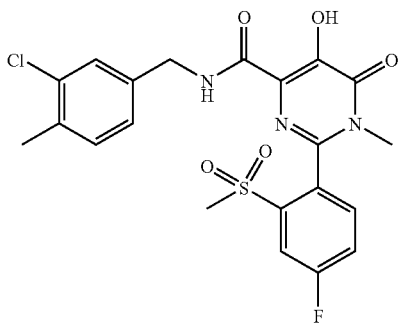

2-(4-Fluoro-2-methanesulfonyl-phenyl)-5-hydroxy-1-methyl-6-oxo-1,6-dihydro-pyrimidine-4-carboxylic acid 3-chloro-4-methyl-benzylamide. Prepared according to the procedure described for example 2 from 2-(4-fluoro-2-methanesulfonyl-phenyl)-5-hydroxy-1-methyl-6-oxo-1,6-dihydro-pyrimidine-4-carboxylic acid ethyl ester (55.56 mg, 0.15 mmol) and 3-chloro-4-methylbenzylamine (107 mg, 0.75 mmol). The title product was obtained as a pink solid (58.6 mg, 81% yield). $^1$HNMR (500 MHz, CDCl$_3$) δ: 12.12 (1H, s), 7.87 (1H, dd, J=7.63, 2.45 Hz), 7.53 (1H, t, J=5.50 Hz), 7.48 (1H, td, J=7.62, 2.74 Hz), 7.42 (1H, dd, J=8.24, 4.89 Hz), 7.20 (1H, s), 7.17 (1H, d, J=7.63 Hz), 7.05 (1H, d, J=7.63 Hz), 4.57 (1H, dd, J=14.95, 6.72 Hz), 4.43 (1H, dd, J=14.95, 5.49 Hz), 3.26 (3H, s), 3.05 (3H, s), 2.33 (3H, s). HRMS (ESI) calcd for C$_{21}$H$_{20}$ClFN$_3$O$_5$S (M+H): 480.0796; found: 480.0793.

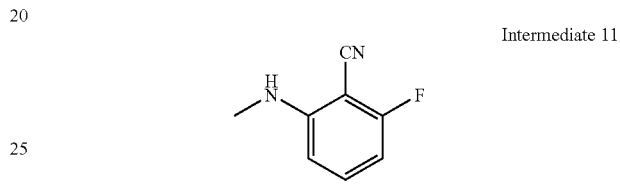

Intermediate 11

2-Fluoro-6-methylamino-benzonitrile. To a stirred solution of 2,6-difluorobenzonitrile (3.5 g, 25.2 mmol) in ethanol (40 mL) was added 2 mL of methylamine (40 wt %, in H$_2$O) and heated at 80° C. for 2 h. The mixture was then diluted with water and the resulting slurry extracted with dichloromethane (3×50 mL). The combined organic extracts were dried (Na$_2$SO$_4$), filtered and concentrated to give the title product as a white solid (3.77 g, 99.6% yield). $^1$HNMR (500 MHz, CDCl$_3$) δ: 7.35–7.31 (1H, m), 6.41–6.38 (2H, m), 4.74 (1H, br s), 2.93 (3H, d, J=5.19 Hz). LCMS calcd for C8H8FN2 (M+H): 151.07.

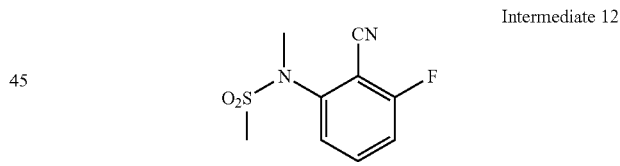

Intermediate 12

N-(2-Cyano-3-fluoro-phenyl)-N-methyl-methanesulfonamide. To a stirred solution of 2-fluoro-6-methylamino-benzonitrile (1.5 g, 10 mmol) in THF (50 mL) at −78° C. was added LiHMDS (1M in THF, 16 mL, 16 mmol) dropwise over 5 min. The resulting pale yellow solution was stirred for an additional 30 min, then methanesulfonyl chloride (1.16 mL, 15 mmol) was added. After 30 min, the reaction mixture was quenched with saturated NH$_4$Cl (1 mL), diluted with ethyl acetate (100 mL), dried (MgSO$_4$), filtered and concentrated to give viscous yellow oil. The crude product was purified on silica gel column (2:3 EtOAc/hexanes) to give the title compound as a white solid (1.5936 g, 70% yield). $^1$HNMR (500 MHz, CDCl$_3$) δ: 7.65–7.61 (1H, m), 7.86 (1H, d, J=8.24 Hz), 7.22 (1H, t, J=8.24 Hz), 3.38 (3H, s), 3.13 (3H, s). HRMS (ESI) calcd for C$_{17}$H$_{22}$FN$_2$O$_7$S (M+H): 417.1132; found: 417.1116.

Intermediate 13

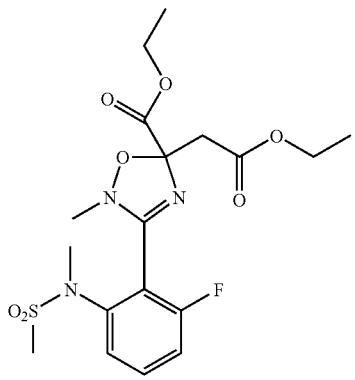

5-Ethoxycarbonylmethyl-3-[2-fluoro-6-(methanesulfonyl-methyl-amino)-phenyl]-2-methyl-2,5-dihydro-[1,2,4]oxadiazole-5-carboxylic acid ethyl ester. To a stirred suspension of N-(2-cyano-3-fluoro-phenyl)-N-methyl-methanesulfonamide (0.685 g, 3.0 mmol) and N-methylhydroxylamine hydrochloride (1.0 g, 12 mmol) in 1:1 water/ethanol (20 mL) was added sodium carbonate (0.936 g, 6 mmol) in small portions and the resulting mixture stirred at 80° C. for 4 h. The reaction mixture was concentrated and the residue re-dissolved into 1:1 water :ethanol (20 mL). To this solution was added diethyl acetylenedicarboxylate (0.64 mL, 4 mmol) and the mixture stirred for 1 h at room temperature. The reaction mixture was then taken up in ethyl acetate (100 mL), washed successively with water and brine (50 mL each), dried (MgSO$_4$), filtered and concentrated to give a yellow oil. The crude product was purified on silica gel column (2:3 to 3:2 ethyl acetate/hexanes) to afford the title compound as a viscous yellow oil (0.7453 g, 56% yield). $^1$HNMR (500 MHz, CDCl$_3$) δ: 7.52–7.48 (1H, m), 7.31 (1H, d, J=8.24 Hz), 7.18 (1H, t, J=8.55 Hz), 4.35–4.25 (2H, m), 4.18 (2H, q, J=7.02 Hz), 3.40 (1H, d, J=16.48 Hz), 3.21 (3H, s), 3.09 (1H, d, J=16.48 Hz), 3.09 (3H, s), 3.07 (3H, s), 1.33 (3H, t, J=7.02 Hz), 1.26 (3H, t, J=7.02 Hz). HRMS (ESI) calcd for C$_{18}$H$_{25}$FN$_3$O$_7$S (M+H): 446.1397; found: 446.1383.

Intermediate 14

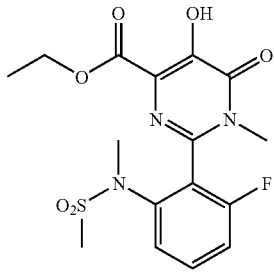

2-[2-Fluoro-6-(methanesulfonyl-methyl-amino)-phenyl]-5-hydroxy-1-methyl-6-oxo-1,6-dihydro-pyrimidine-4-carboxylic acid ethyl ester. A solution of 5-ethoxycarbonylmethyl-3-[2-fluoro-6-(methanesulfonyl-methyl-amino)-phenyl]-2-methyl-2,5-dihydro-[1,2,4]oxadiazole-5-carboxylic acid ethyl ester (740 mg, 1.6612 mmol) in xylenes (10 mL) was placed in a pre-heated oil bath and heated to reflux for 2 h. Heating was stopped and the reaction mixture was allowed to cool slowly to room temperature. The precipitated product was separated by decanting the solvent, then rinsed with ether and dried to give the title compound as a yellow solid (374.8 mg, 56% yield). $^1$HNMR (500 MHz, CDCl$_3$) δ: 10.65 (1H, s), 7.57–7.52 (1H, m), 7.28 (1H, d, J=7.94 Hz), 7.22 (1H, t, J=8.85 Hz), 4.55–4.49 (1H, m), 4.40–4.33 (1H, m), 3.46 (3H, s), 3.30 (3H, s), 2.90 (3H, s)1.37 (3H, t, J=7.02 Hz). HRMS (ESI) calcd for C$_{16}$H$_{19}$FN$_3$O$_6$S (M+H): 400.0979; found: 400.0979.

EXAMPLE 34

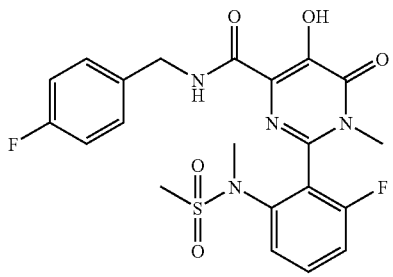

N-(4-fluorobenzyl)-2-(2-fluoro-6-(N-methylmethan-3-yl-sulfonamido)phenyl)-5-hydroxy-1-methyl-6-oxo-1,6-dihydropyrimidine-4-carboxamide. Prepared according to the procedure described for example 2 from 2-[2-fluoro-6-(methanesulfonyl-methyl-amino)-phenyl]-5-hydroxy-1-methyl-6-oxo-1,6-dihydro-pyrimidine-4-carboxylic acid ethyl ester (60 mg, 0.15 mmol) and 4-fluorobenzylamine (95 mg, 0.75 mmol). The title product was obtained as a pink solid (64.2 mg, 89% yield). $^1$HNMR (500 MHz, CDCl$_3$) δ: 12.14 (1H, s), 7.76 (1H, t, J=5.50 Hz), 7.57–7.53 (1H, m), 7.28–7.21 (4H, m), 7.03–6.98 (2H, m), 4.59 (1H, dd, J=14.65, 6.71 Hz), 4.47 (1H, dd, J=14.96, 5.80 Hz), 3.42 (3H, s), 3.08 (3H, s), 2.86(3H, s). HRMS (ESI) calcd for C$_{21}$H$_{21}$F$_2$N$_4$O$_5$S (M+H): 479.1201; found: 479.1196.

EXAMPLE 35

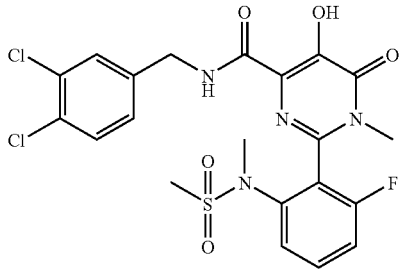

N-(3,4-dichlorobenzyl)-2-(2-fluoro-6-(N-methylmethan-3-ylsulfonamido)phenyl)-5-hydroxy-1-methyl-6-oxo-1,6-dihydropyrimidine-4-carboxamide. Prepared according to the procedure described for example 2 from 2-[2-fluoro-6-(methanesulfonyl-methyl-amino) -phenyl]-5-hydroxy-1-methyl-6-oxo-1,6-dihydro-pyrimidine-4-carboxylic acid ethyl ester (60 mg, 0.15 mmol) and 3,4-dichlorobenzylamine (132 mg, 0.75 mmol). The title product was obtained as a pink solid (68.2 mg, 86% yield). $^1$HNMR (500 MHz, CDCl$_3$) δ: 12.00 (1H, s), 7.85 (1H, t, J=5.50 Hz), 7.59–7.54

(1H, m), 7.39 (1H, d, J=8.54 Hz), 7.38 (1H, s), 7.26–7.22 (2H, m), 7.15 (1H, dd, J=8.24, 2.13 Hz), 4.59 (1H, dd, J=15.26, 6.72 Hz), 4.45 (1H, dd, J=15.26, 5.80 Hz), 3.43 (3H, s), 3.12 (3H, s), 2.91 (3H, s). HRMS (ESI) calcd for $C_{21}H_{20}Cl_2FN_4O_5S$ (M+H): 529.0516; found: 529.0505.

EXAMPLE 36

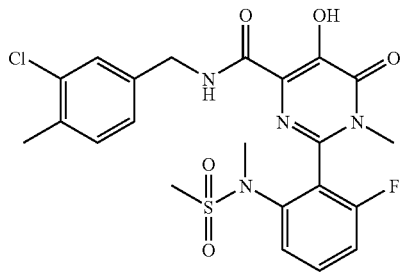

N-(3-chloro-4-methylbenzyl)-2-(2-fluoro-6-(N-methyl-methan-3-ylsulfonamido)phenyl)-5-hydroxy-1-methyl-6-oxo-1,6-dihydropyrimidine-4-carboxamide. Prepared according to the procedure described for example 2 from 2-[2-fluoro-6-(methanesulfonyl-methyl-amino)-phenyl]-5-hydroxy-1-methyl-6-oxo-1,6-dihydro-pyrimidine-4-carboxylic acid ethyl ester (60 mg, 0.15 mmol) and 3-chloro-4-methylbenzylamine (107 mg, 0.75 mmol). The title product was obtained as a pink solid (59.8 mg, 78% yield). $^1$HNMR (500 MHz, CDCl$_3$) δ: 12.11 (1H, s), 7.76 (1H, t, J=5.50 Hz), 7.58–7.53 (1H, m), 7.26–7.21 (3H, m), 7.17 (1H, d, J=7.63 Hz), 7.08 (1H, dd, J=7.93, 1.52 Hz), 4.58 (1H, dd, J=14.95, 6.72 Hz), 4.43 (1H, dd, J=14.95, 5.50 Hz), 3.43 (3H, s), 3.12 (3H, s), 2.87 (3H, s), 2.33 (3H, s). HRMS (ESI) calcd for $C_{22}H_{23}ClFN_4O_5S$ (M+H): 509.1062; found: 509.1055.

Intermediate 15

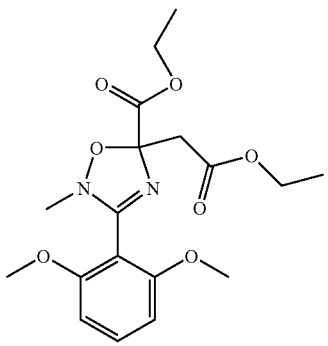

3-(2,6-Dimethoxy-phenyl)-5-ethoxycarbonylmethyl-2-methyl-2,5-dihydro-[1,2,4]oxadiazole-5-carboxylic acid ethyl ester. To a stirred suspension of 2,6-dimethoxy-benzonitrile (0.82 g, 5 mmol) and N-methylhydroxylamine hydrochloride (1.66 g, 20 mmol) in 1:1 water/ethanol (20 mL) was added sodium carbonate (1.05 g, 10 mmol) in small portions and the resulting mixture stirred at 80° C. for 24 h. The reaction mixture was concentrated and the residue was re-dissolved into 1:1 water:ethanol (25 mL). To this solution was added diethyl acetylenedicarboxylate (0.96 mL, 6 mmol) and the resulting mixture stirred for 30 min at room temperature. The reaction mixture was then taken up in ethyl acetate (100 mL), washed successively with water and brine (50 mL each), dried (Na$_2$SO$_4$), filtered and concentrated to give a yellow oil. The crude product was purified on silica gel column (3:7 to 1:1 ethyl acetate/hexanes) to afford the title compound as a viscous yellow (1.5795 g, 83% yield). $^1$HNMR (500 MHz, CDCl$_3$) δ: 7.32 (1H, t, J=8.24 Hz), 6.55 (2H, d, J=8.24 Hz), 4.38–4.24 (2H, m), 4.20–4.14 (2H, m), 3.80 (6H, s), 3.48 (1H, d, J=16.48 Hz), 3.03 (1H, d, J=16.48 Hz), 3.02 (3H, s), 1.33 (3H, t, J=7.02 Hz), 1.26 (3H, 7.02 Hz). HRMS (ESI) calcd for $C_{18}H_{25}N_2O_7S$ (M+H): 381.1662; found: 381.1656.

Intermediate 16

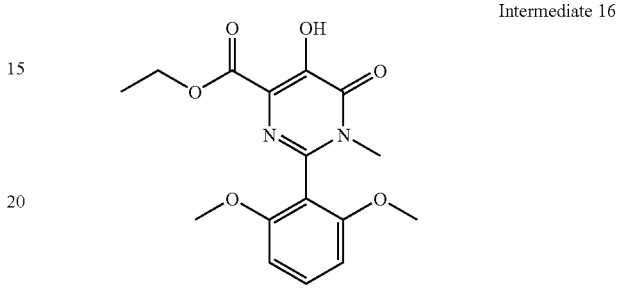

2-(2,6-Dimethoxy-phenyl)-5-hydroxy-1-methyl-6-oxo-1,6-dihydro-pyrimidine-4-carboxylic acid ethyl ester. A solution of 3-(2,6-dimethoxy-phenyl)-5-ethoxycarbonylmethyl-2-methyl-2,5-dihydro-[1,2,4]oxadiazole-5-carboxylic acid ethyl ester (1.577 g, 4.1457 mmol) in xylenes (15 mL) was placed in a pre-heated oil bath and refluxed for 2 h. Heating was stopped and the reaction mixture was allowed to cool slowly to room temperature. The precipitated product was separated by decanting the solvent, rinsed with ether and dried to give the title compound as a brown solid (1.386 g, 62% yield). $^1$HNMR (500 MHz, CDCl$_3$) δ: 10.83 (1H, s), 7.35 (1H, t, J=8.54 Hz), 6.59 (2H, d, J=8.54 Hz), 4.50 (2H, q, J=7.02 Hz), 3.75 (6H, s), 3.28 (3H, s), 1.39 (3H, t, J=7.02 Hz). HRMS (ESI) calcd for $C_{16}H_{19}N_2O_6$ (M+H): 335.1243; found: 335.1240.

EXAMPLE 37

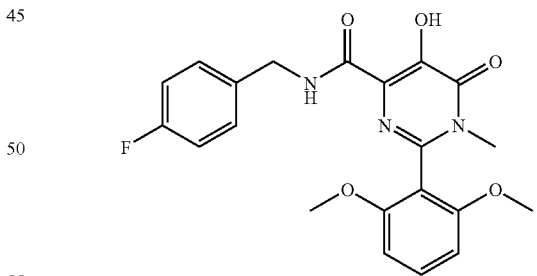

N-(4fluorobenzyl)-2-(2,6-dimethoxyphenyl)-5-hydroxy-1-methyl-6-oxo-1,6-dihydropyrimidine-4-carboxamide. Prepared according to the procedure described for example 2 from 2-(2,6-dimethoxy-phenyl)-5-hydroxy-1-methyl-6-oxo-1,6-dihydro-pyrimidine-4-carboxylic acid ethyl ester (50 mg, 0.15 mmol) and 4-fluorobenzylamine (125 mg, 1.0 mmol). The title product was obtained as a pink solid (48.7 mg, 79% yield). $^1$HNMR (500 MHz, CDCl$_3$) δ: 12.10 (1H, s), 7.92 (1H, t, J=5.50 Hz), 7.39 (1H, d, J=8.54 Hz), 7.30 (1H, d, J=5.19 Hz), 7.28 (1H, d, J=5.19 Hz), 7.00 (2H, t, J=8.54 Hz), 6.62 (2H, d, J=8.24 Hz), 4.52 (2H, d, J=6.40 Hz), +3.75

(6H, s), 3.28 (3H, s). HRMS (ESI) calcd for $C_{21}H_{21}FN_3O_5$ (M+H): 414.1465; found: 414.1454.

EXAMPLE 38

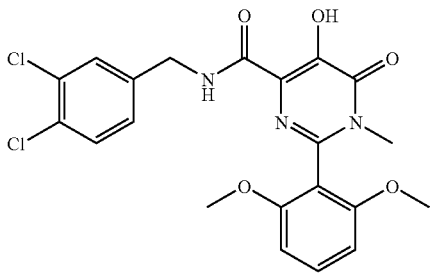

N-(3,4-dichlorobenzyl)-2-(2,6-dimethoxyphenyl)-5-hydroxy-1-methyl-6-oxo-1,6-dihydropyrimidine-4-carboxamide. Prepared according to the procedure described for example 2 from 2-(2,6-dimethoxy-phenyl)-5-hydroxy-1-methyl-6-oxo-1,6-dihydro-pyrimidine -4-carboxylic acid ethyl ester (74.07 mg, 0.20 mmol) and 3,4-dichlorobenzylamine (132 mg, 0.75 mmol). The title product was obtained as a pink solid (57.8 mg, 83% yield). $^1$HNMR (500 MHz, CDCl$_3$) δ: 11.95 (1H, s), 7.97 (1H, t, J=5.50 Hz), 7.41–7.38 (3H, m), 7.16 (1H, dd, J=8.24, 2.14 Hz), 6.63 (2H, d, J=8.24 Hz), 6.50 (2H, d, J=6.40 Hz), 3.76 (6H, s), 3.29 (3H, s). HRMS (ESI) calcd for $C_{21}H_{20}Cl_2N_3O_5$ (M+H): 464.0780; found: 464.0775.

EXAMPLE 39

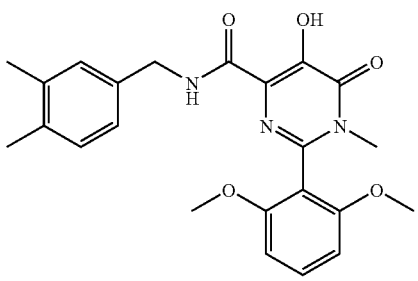

N-(3,4-dimethylbenzyl)-2-(2,6-dimethoxyphenyl)-5-hydroxy-1-methyl-6-oxo-1,6-dihydropyrimidine-4-carboxamide. Prepared according to the procedure described for example 2 from 2-(2,6-dimethoxy-phenyl)-5-hydroxy-1-methyl-6-oxo-1,6-dihydro-pyrimidine-4-carboxylic acid ethyl ester (50 mg, 0.15 mmol) and 3,4-dimethylbenzylamine (102 mg, 0.75 mmol). The title product was obtained as a brown solid (52 mg, 82% yield). $^1$HNMR (500 MHz, CDCl$_3$) δ: 12.28 (1H, s), 7.88 (1H, t, J=5.50 Hz), 7.38 (1H, t, J=8.24 Hz), 7.10–7.03 (3H, m), 6.61 (2H, d, J=8.54 Hz), 4.48 (2H, d, J=6.11 Hz), 3.75 (6H, s), 3.28 (3H, s), 2.23 (3H, s), 2.22 (3H, s). HRMS (ESI) calcd for $C_{23}H_{26}N_3O_5$ (M+H): 424.1873; found: 424.1863.

EXAMPLE 40

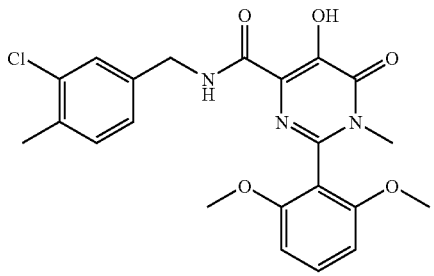

N-(3-chloro-4-methylbenzyl)-2-(2,6-dimethoxyphenyl)-5-hydroxy-1-methyl-6-oxo-1,6-dihydropyrimidine-4-carboxamide. Prepared according to the procedure described for example 2 from 2-(2,6-dimethoxy-phenyl)-5-hydroxy-1-methyl-6-oxo-1,6-dihydro-pyrimidine-4-carboxylic acid ethyl ester (50 mg, 0.15 mmol) and 3-chloro-4-methylbenzylamine (107 mg, 0.75 mmol). The title product was obtained as a pink solid (51.1 mg, 77% yield). $^1$HNMR (500 MHz, CDCl$_3$) δ: 12.09 (1H, s), 7.92 (1H, t, J=5.50 Hz), 7.39 (1H, t, J=8.24 Hz), 7.28 (1H, d, J=1.22 Hz), 7.17 (1H, d, J=7.63 Hz), 7.10 (1H, dd, J=7.63, 1.53 Hz), 6.62 (2H, d, J=8.24 Hz), 4.49 (2H, d, J=6.40 Hz), 3.76 (6H, s), 3.28 (3H, s), 2.33 (3H, s). HRMS (ESI) calcd for $C_{22}H_{23}ClN_3O_5$ (M+H): 444.1326; found: 444.1327.

Intermediate 17

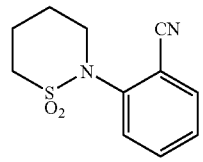

2-(1,1-Dioxo-1λ$^6$-[1,2]thiazinan-2-yl)-benzonitrile. To a suspension of sodium hydride (0.54 g, 95%, 20 mmol) in DMF (25 mL) was added [1,2]thiazinane 1,1-dioxide (2.70 g, 20 mmol). After stirring the mixture at room temperature for 15 min, 2-fluorobenzonitrile (2.7 mL, 25 mmol) was added and the resulting mixture was stirred at 80° C. for 18 h, cooled, diluted with water and the resulting solid filtered. The mother liquor was concentrated and the residue was recrystalized from 1:1 ethyl acetate/hexanes to yield the title product as an orange solid (3.47 g, 74% yield). $^1$HNMR (500 MHz, CDCl$_3$) δ: 7.69 (1H, dd, J=7.63, 1.23 Hz), 7.62–7.55 (2H, m) 7.40 (1H, t, J=7.63 Hz), 3.72 (2H, t, J=5.19 Hz), 3.31 (2H, t, J=6.10 Hz), 2.39–2.34 (2H, m), 2.04–1.99 (2H, m). LCMS calcd for $C_{11}H_{13}N_2O_2S$ (M+H): 237.29; found: 237.26.

Intermediate 18

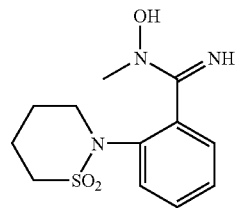

2-(1,1-Dioxo-1λ⁶-[1,2]thiazinan-2-yl)-N-hydroxy-N-methyl-benzamidine. To a stirred solution of 2-(1,1-dioxo-1λ⁶-[1,2]thiazinan-2-yl)-benzonitrile and N-methylhydroxylamine hydrochloride (1.67 g, 20 mmol) in 1:1 water/ethanol (70 mL) was added sodium carbonate (1.06 g, 10 mmol) and the resulting mixture stirred at 90° C. for 18 h. After cooling and concentration, the resulting residue was suspended in MeOH/CHCl₃ (100 mL, 1:9). The insoluble solids were removed by filtration and concentration of the filtrate gave the crude product as an amber oil (3.5 g) that was carried on without further purification. LCMS calcd for $C_{12}H_{17}N_3O_3S$ (M+H): 284.35; found: 284.27.

(3.62 g, 8.0 mmol) in xylenes (50 mL) was refluxed 3 h then cooled to room temperature. The mixture was stored at 5° C. for 5 h. The resulting precipitate was filtered to afford the title product as a pale orange solid (1.67 g, 51% yield). ¹HNMR (300 MHz, CDCl₃) δ: 10.64 (1H, s), 7.65 (1H, dd, J=8.05, 1.10 Hz), 7.53 (1H, td, J=7.32, 1.46 Hz), 7.45, (1H, td, J=7.68, 1.46 Hz), 7.35 (1H, dd, J=7.32, 1.47 Hz), 4.59–4.49 (1H, m), 4.46–4.35 (1H, m), 3.75 (1H, td, J=13.17, 2.93 Hz), 3.65–3.58 (1H, m), 3.41 (3H, s), 3.10 (1H, dt, J=12.93, 4.21 Hz), 2.76 (1H, td, J=12.45, 4.39 Hz), 2.36–2.10 (2H, m), 1.77–1.45 (2H m), 1.38 (3H, t, J=7.32 Hz). HRMS (ESI) calcd for $C_{18}H_{22}N_3O_6S$ (M+H): 408.1277; found 408.1231.

Intermediate 19

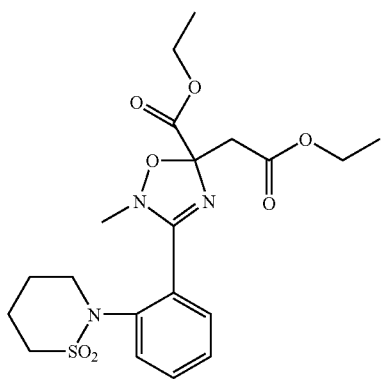

3-[2-(1,1-Dioxo-1λ⁶-[1,2]thiazinan-2-yl)-phenyl]-5-ethoxycarbonylmethyl-2-methyl-2,5-dihydro-[1,2,4]oxadiazole-5-carboxylic acid ethyl ester. To a stirred solution of 2-(1,1-dioxo-1λ⁶-[1,2]thiazinan-2-yl)-N-hydroxy-N-methyl-benzamidine (3.5 g) in ethanol (100 mL, 200 proof) was added diethyl acetylene-dicarboxylate (3.2 mL, 20 mmol) and the resulting mixture stirred at room temperature for 30 min. The mixture was concentrated and purified on a silica gel column (10%–30% ethyl acetate/hexanes) to afford the title compound as a yellow oil (3.62 g, 40% yield). ¹HNMR (300 MHz, CDCl₃) δ: 7.57 (2H, td, J=7.14, 1.28 Hz,), 7.50 (1H, td, J=7.68, 1.83 Hz), 7.39 (1H, td, J=7.50, 1.46 Hz), 4.34–4.22 (2H, m), 4.18 (2H, q, J=7.08 Hz), 3.42 (1H, d, J=16.47 Hz), 3.22–3.18 (2H, m), 3.07 (3H, s), 3.05 (1H, d, J=16.46 Hz), 2.38–2.24 (2H, m), 2.00–1.42 (2H, m), 1.33 (3H, t, J=7.14 Hz), 1.26 (3H, t, J=7.14 Hz). HRMS calcd for $C_{20}H_{28}SN_3O_7$ (M+H): 454.1648; found: 454.1650.

Intermediate 20

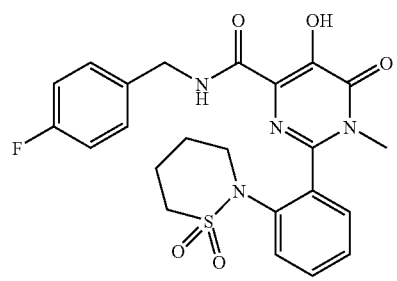

2-[2-(1,1-Dioxo-1λ⁶-[1,2]thiazinan-2-yl)-phenyl]-5-hydroxy-1-methyl-6-oxo-1,6-dihydro-pyrimidine-4-carboxylic acid ethyl ester. A solution of 3-[2-(1,1-dioxo-1λ⁶-[1,2]thiazinan-2-yl)-phenyl]-5-ethoxycarbonylmethyl-2-methyl-2,5-dihydro-[1,2,4]oxadiazole-5-carboxylic acid ethyl ester

EXAMPLE 41

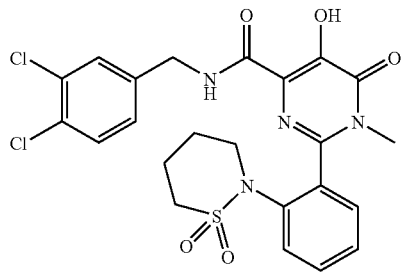

N-(4-fluorobenzyl)-5-hydroxy-1-methyl-2-(2-(1,1-Dioxo-1λ⁶-[1,2]thiazinan-2-yl)-6-oxo-1,6-dihydropyrimidine-4-carboxamide. Prepared according to the procedure described for example 2 from 2-[2-(1,1-dioxo-1λ⁶-[1,2]thiazinan-2-yl)-phenyl]-5-hydroxy-1-methyl-6-oxo-1,6-dihydro-pyrimidine-4-carboxylic acid ethyl ester (0.0814 g, 0.2mmol), and 4-fluorobenzylamine (0.11 mL, 1.0 mmol). The title product was obtained as a lavender solid (0.0626 g, 64% yield). ¹HNMR (300 MHz, CDCl₃) δ: 12.12 (1H, s), 7.83 (1H, bs), 7.64 (1H, d, J=7.32 Hz), 7.54 (1H, td J=7.32, 1.46 Hz), 7.46 (1H, td, J=7.69, 1.10 Hz), 7.33 (1H, d, J=7.68 Hz), 7.28–7.23 (2H, m), 7.00 (2H, t, J=8.42 Hz), 4.59 (1H, dd, J=14.83, 6.78 Hz), 4.46 (1H, dd, J=14.82, 6.04 Hz), 3.68–3.52 (1H, m), 3.44–3.33 (1H, m), 3.38 (3H, m), 3.14–2.94 (1H, m), 2.82–2.73 (1H, m), 2.30–2.06 (2H, m), 1.57–1.52 (1H, m), 1.34–1.19 (1H, m). HRMS (ESI) calcd for $C_{23}H_{22}N_4O_5FS$ (M−H): 485.1295; found: 485.1286.

EXAMPLE 42

N-(3,4-dichlorobenzyl)-5-hydroxy-1-methyl-2-(2-(1,1-Dioxo-1λ⁶-[1,2]thiazinan-2-yl)-6-oxo-1,6-dihydropyrimidine-4-carboxamide. Prepared according to the procedure described for example 2 from 2-[2-(1,1-dioxo-1λ⁶-[1,2]

thiazinan-2-yl)-phenyl]-5-hydroxy-1-methyl-6-oxo-1,6-dihydro-pyrimidine-4-carboxylic acid ethyl ester (0.0814 g, 0.2 mmol) and 3,4-dichlorobenzylamine (0.13 mL, 1.0 mmol). The title product was obtained as white needles after recrystalization from MeOH/H$_2$O (0.0443 g, 41% yield). $^1$HNMR (300 MHz, CDCl$_3$) δ: 11.98 (1H, s), 7.90 (1H, bs), 7.65 (1H, d, J=7.68 Hz), 7.55 (1H, td, J=7.32, 1.46 Hz), 7.47 (1H, td, J=7.69, 1.46 Hz), 7.40–7.33 (3H, m), 7.13 (1H, dd, J=8.05, 1.83 Hz ), 4.60 (1H, dd, J=15.18, 6.77 Hz), 4.43 (1H, dd, J=15.00, 5.86 Hz), 3.62, (1H, bs), 3.49–3.34 (1H, m), 3.38 (3H, s), 3.05 (1H, bs), 2.89–2.75 (1H, m), 2.31–2.09 (2H, m), 1.70–1.54 (2H, m). HRMS (ESI) calcd for C$_{23}$H$_{23}$SCl$_2$N$_4$O$_5$ (M+H): 537.0766; found: 537.0758.

EXAMPLE 43

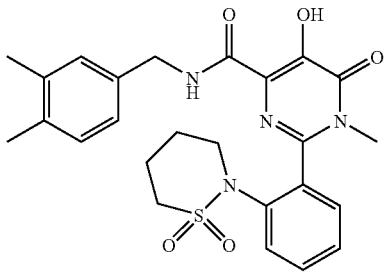

N-(3,4-dimethylbenzyl)-5-hydroxy-1-methyl-2-(2-(1,1-Dioxo-1λ$^6$-[1,2]thiazinan-2-yl)-6-oxo-1,6-dihydropyrimidine-4-carboxamide. Prepared according to the procedure described for example 2 from 2-[2-(1,1-dioxo-1λ$^6$-[1,2]thiazinan-2-yl)-phenyl]-5-hydroxy-1-methyl-6-oxo-1,6-dihydro-pyrimidine-4-carboxylic acid ethyl ester (0.0814 g, 0.2 mmol) and 3,4-dimethylbenzylamine (0.14 mL, 1.0 mmol). The title product was obtained as lavender needles after recrystalization from MeOH/H$_2$O (0.0576 g, 58% yield). $^1$HNMR (300 MHz, CDCl$_3$) δ: 12.23 (1H, s), 7.77 (1H, bs), 7.63 (1H, d, J=7.32 Hz), 7.53 (1H, td, J=7.31, 1.46 Hz), 7.45 (1H, td, J=7.68, 0.98 Hz), 7.33 (1H, d, J=7.32 Hz), 7.08–6.98 (3H, m), 4.55 (1H, dd, J=14.81, 6.40 Hz), 4.43 (1H, dd, J=14.64, 5.49 Hz), 3.62 (1H, bs), 3.37 (3H, s), 3.34 (1H, bs), 3.04 (1H, bs), 2.80–2.71 (1H, m), 2.22 (6H, s), 2.22–2.06 (2H, m), 1.64–1.52 (2H, m). HRMS (ESI) calcd for C$_{25}$H$_{29}$SN$_4$O$_5$ (M+H): 497.1859; found: 497.1847.

EXAMPLE 44

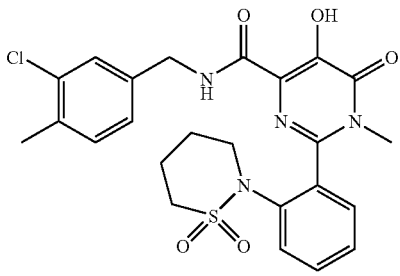

N-(3-chloro-4-methylbenzyl)-5-hydroxy-1-methyl-2-(2-(1,1-Dioxo-1λ$^6$-[1,2]thiazinan-2-yl)-6-oxo-1,6-dihydropyrimidine-4-carboxamide. Prepared according to the procedure described for example 2 from 2-[2-(1,1-dioxo-1λ$^6$-[1,2]thiazinan-2-yl)-phenyl]-5-hydroxy-1-methyl-6-oxo-1,6-dihydro-pyrimidine-4-carboxylic acid ethyl ester (0.0814 g, 0.2 mmol) and 3-chloro-4-methylbenzylamine (0.14 mL, 1.0 mmol). The title product was obtained as white needles after recrystalization from MeOH/H$_2$O (0.0416 g, 40% yield). $^1$HNMR (300 MHz, CDCl$_3$) δ: 11.98 (1H, s), 7.84 (1H, bs), 7.64 (1H, d, J=8.05 Hz), 7.54 (1H, td, J=7.68, 1.83 Hz), 7.46 (1H, td, J=7.68, 1.46 Hz), 7.34 (1H, dd, J=7.32, 1.47 Hz), 7.23 (1H, d, J=0.74 Hz), 7.17 (1H, d, J=7.69 Hz), 7.07 (1H, dd, J=7.69, 1.47 Hz), 4.61 (1H, dd, J=15.19, 6.77 Hz), 4.40 (1H, dd, J=15.00, 5.49 Hz), 3.62 (1H, bs), 3.42 (1H, bs) 3.38 (3H, s), 3.05 (1H, bs), 2.83–2.74 (1H, m), 2.33 (3H, s), 2.27–2.11 (2H, m), 1.63–1.60 (2H, m). HRMS (ESI) calcd for C$_{24}$H$_{26}$SClN$_4$O$_5$ (M+H): 517.1312; found: 517.1310.

Intermediate 21

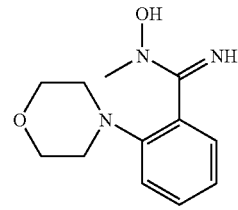

N-Hydroxy-N-methyl-2-morpholin-4-yl-benzamidine. To a stirred solution of 2-(4-morpholino)benzonitrile (3.76 g, 20 mmol) and N-methylhydroxylamine hydrochloride (3.34 g, 40.0 mmol) in 1:1 water/ethanol (100 mL) was added sodium carbonate (2.12 g, 20 mmol) and the resulting mixture stirred at 90° C. overnight. After cooling and concentrating, the resulting residue was suspended in MeOH/CHCl$_3$ (1:9). The insoluble solids were removed by filtration and concentration of the mother liquor gave the title product as an amber oil (3.8 g) that was carried on without further purification. LCMS calcd for C$_{12}$H$_{18}$N$_3$O$_2$ (M+H): 236.13; found: 236.31.

Intermediate 22

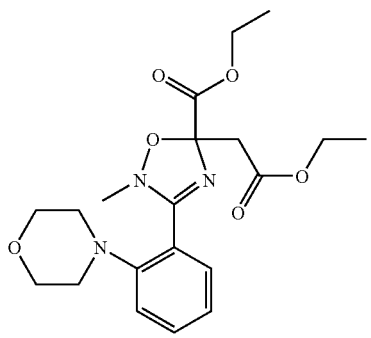

5-Ethoxycarbonylmethyl-2-methyl-3-(2-morpholin-4-yl-phenyl)-2,5-dihydro-[1,2,4]oxadiazole-5-carboxylic acid ethyl ester. To a stirred solution of N-hydroxy-N-methyl-2-morpholin-4-yl-benzamidine (3.8 g) in ethanol (100 mL, 200 proof) was added diethyl acetylene-dicarboxylate (3.2 mL, 20 mmol) and the resulting mixture stirred at room temperature for 30 min. The mixture was then concentrated and purified on a silica gel column (10%–30% ethyl acetate/hexanes) to afford the title compound (3.64 g, 45% yield). $^1$HNMR (300 MHz, CDCl$_3$) δ: 7.64 (1H, dd, J=7.69, 1.83 Hz), 7.40 (1H, td, J=8.05, 1.83 Hz), 7.02 (1H, t, J=7.32 Hz), 6.97 (1H, d, J=8.05 Hz) 4.31–4.20 (2H, m), 4.15 (2H, q, J=7.08 Hz), 3.88–3.74 (4H, m), 3.38 (1H, d, J=16.46 Hz), 3.12–2.92 (4H, m), 3.05 (3H, s), 3.03 (1H, d, J=16.47 Hz), 1.29 (3H, t, J=6.95 Hz), 1.25 (3H, t, J=6.96 Hz). HRMS (ESI) calcd for $C_{20}H_{28}N_3O_6$ (M+H): 406.1978; found: 406.1975.

Intermediate 23

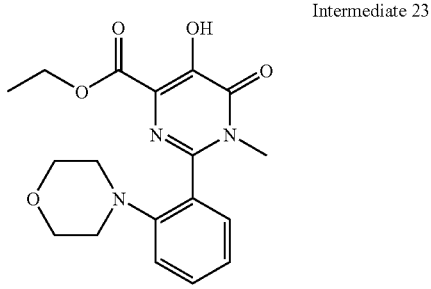

5-Hydroxy-1-methyl-2-(2-morpholin-4-yl-phenyl)-6-oxo-1,6-dihydro-pyrimidine-4-carboxylic acid ethyl ester. A solution of 5-ethoxycarbonylmethyl-2-methyl-3-(2-morpholin-4-yl-phenyl)-2,5-dihydro-[1,2,4]oxadiazole-5-carboxylic acid ethyl ester (3.64 g, 9.0 mmol) in xylenes (30 mL) was heated to reflux for 18 h then cooled to room temperature. Hexanes (30 mL) was added and the mixture stored at 5° C. for 5 h. The solution was decanted leaving a red residue that was purified by silica gel column (25%–50% ethyl acetate/hexanes) to afford the title product as an orange powder (0.4723 g, 14% yield). $^1$HNMR (300 MHz, CDCl$_3$) δ: 10.76 (1H, s), 7.46 (1H, td, J=8.05, 1.46 Hz), 7.36 (1H, dd, J=7.68, 1.83 Hz), 7.19 (1H, td, J=7.32, 0.74 Hz), 7.11 (1H, d, J=8.06 Hz), 4.58–4.38 (2H, m), 3.63–3.59 (4H, m), 3.36 (3H, s), 3.11–3.04 (2H, m), 2.82–2.75 (2H, m), 1.41 (3H, t, J=7.32 Hz). HRMS (ESI) calcd for $C_{18}H_{22}N_3O_5$ (M+H): 360.1560; found: 360.1563.

EXAMPLE 45

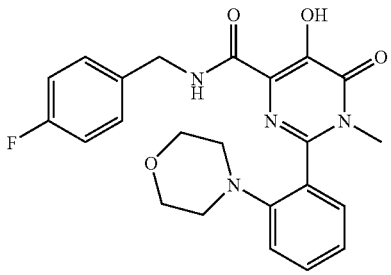

N-(4-fluorobenzyl)-5-hydroxy-1-methyl-2-(2-morpholinophenyl)-6-oxo-1,6-dihydropyrimidine-4-carboxamide. Prepared according to the procedure described for example 2 from 5-hydroxy-1-methyl-2-(2-morpholin-4-yl-phenyl)-6-oxo-1,6-dihydro-pyrimidine-4-carboxylic acid ethyl ester (0.05 g, 0.15 mmol) and 4-fluorobenzylamine (0.086 mL, 0.75 mmol). The title product was obtained as a TFA salt, lavender solid (0.0575 g, 87% yield). $^1$HNMR (500 MHz, CDCl$_3$) δ: 12.11 (1H, s), 7.89 (1H, t, J=5.49 Hz), 7.48 (1H, t, J=7.63 Hz), 7.29–7.27 (3H, m), 7.17 (1H, t, J=7.63 Hz), 7.13 (1H, d, J=8.24 Hz), 7.02 (2H, t, J=8.55 Hz), 4.62–4.58, (1H, m), 4.50–4.46 (1H, m), 3.60 (4H, d, J=2.75 Hz), 3.36 (3H, s), 3.01–2.98 (2H, m), 2.78–2.76 (2H, m). HRMS (ESI) calcd for $C_{23}H_{24}FN_4O_4$ (M+H): 439.1782; found 439.1767.

EXAMPLE 46

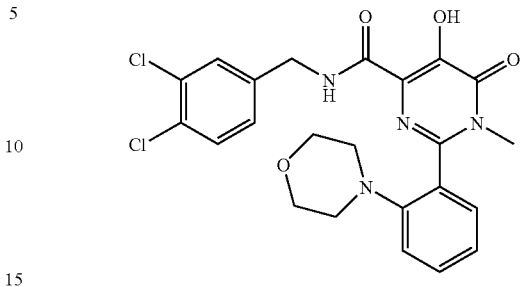

N-(3,4-dichlorobenzyl)-5-hydroxy-1-methyl-2-(2-morpholinophenyl)-6-oxo-1,6-dihydropyrimidine-4-carboxamide. Prepared according to the procedure described for example 2 from 5-hydroxy-1-methyl-2-(2-morpholin-4-yl-phenyl)-6-oxo-1,6-dihydro-pyrimidine-4-carboxylic acid ethyl ester (0.05 g, 0.15 mmol) and 3,4-dichlorobenzylamine (0.10 mL, 0.75 mmol). The title product was obtained as a TFA salt, lavender foam (0.0461 g, 63% yield). $^1$HNMR (500 MHz, CDCl$_3$) δ: 11.95 (1H, bs), 7.94 (1H, t, J=5.50 Hz), 7.49 (1H, t, J=7.63 Hz), 7.40 (1H, d, J=8.24 Hz), 7.38 (1H, d, J=0.91 Hz), 7.30 (1H, d, J=7.33 Hz), 7.19 (1H, t, J=7.33 Hz), 7.14 (2H, t, J=8.09 Hz), 4.56–4.49 (2H, m), 3.61 (4H, s), 3.36 (3H, s), 2.99 (2H, bs), 2.79 (2H, bs). HRMS (ESI) calcd for $C_{23}H_{23}Cl_2N_4O_4$ (M+H): 489.1096; found: 489.1080.

EXAMPLE 47

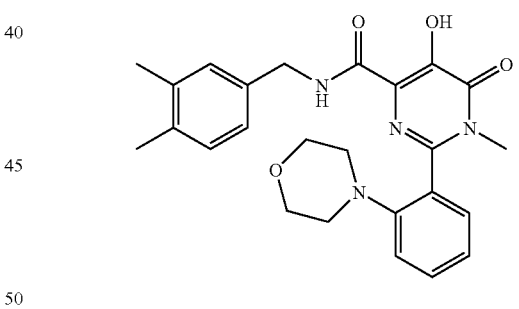

N-(3,4-dimethylbenzyl)-5-hydroxy-1-methyl-2-(2-morpholinophenyl)-6-oxo-1,6-dihydropyrimidine-4-carboxamide. Prepared according to the procedure described for example 2 from 5-hydroxy-1-methyl-2-(2-morpholin-4-yl-phenyl)-6-oxo-1,6-dihydro-pyrimidine-4-carboxylic acid ethyl ester (0.05 g, 0.15 mmol) and 3,4-dimethylbenzylamine (0.11 mL, 0.75 mmol). The title product was obtained as a TFA salt, lavender foam (0.0440 g, 65% yield). $^1$HNMR (500 MHz, CDCl$_3$) δ: 7.84 (1H, t, J=5.49 Hz), 7.49 (1H, t, J=7.49 Hz), 7.28 (1H, d, J=7.63 Hz), 7.18 (1H, t, J=7.32 Hz), 7.14 (1H, d, J=8.24 Hz), 7.09 (1H, d, J=7.63 Hz), 7.07 (1H, s), 7.03 (1H, d, J=7.63 Hz), 4.50 (2H, d, J=5.80 Hz), 3.63 (4H, t, J=4.57 Hz), 3.37 (3H, s), 2.89 (4H, bs), 2.23 (6H, s). HRMS (ESI) calcd for $C_{25}H_{29}N_4O_4$ (M+H): 449.2189; found: 449.2182.

EXAMPLE 48

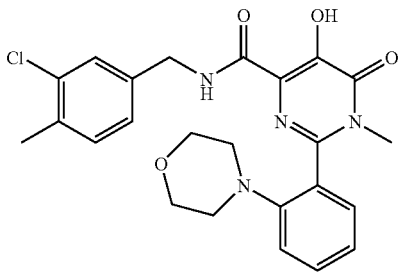

N-(3-chloro4-methylbenzyl)-5-hydroxy-1-methyl-2-(2-morpholinophenyl)-6-oxo-1,6-dihydropyrimidine-4-carboxamide. Prepared according to the procedure described for example 2 from 5-hydroxy-1-methyl-2-(2-morpholin-4-yl-phenyl)-6-oxo-1,6-dihydro-pyrimidine-4-carboxylic acid ethyl ester (0.05 g, 0.15 mmol) and 3-chloro-4-methylbenzylamine (0.11 mL, 0.75 mmol). The title product was obtained as a TFA salt, lavender foam (0.0266 g, 38% yield). $^1$HNMR (500 MHz, CDCl$_3$) δ: 12.07 (1H, bs), 7.88 (1H, t, J=6.10 Hz), 7.48 (1H, td, J=6.71, 1.37 Hz), 7.30–7.27 (2H, m), 7.19–7.16 (2H, m), 7.13 (1H, d, J=8.24 Hz), 7.09 (1H, d, J=7.63 Hz), 4.56–4.53 (1H, m), 4.49–4.45 (m, 1H), 3.61 (4H, d, J=4.27 Hz), 3.36 (3H, s), 3.00 (2H, bs), 2.78 (2H, bs), 2.38 (3H, s). HRMS (ESI) calcd for C$_{24}$H$_{26}$ClN$_4$O$_4$ (M+H): 469.1643; found: 469.1628.

Intermediate 24

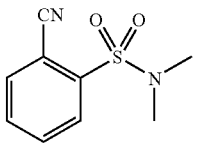

2-Cyano-N,N-dimethyl-benzenesulfonamide. A solution of 2-cyanobenzensulfonylchloride (2.0 g, 10 mmol), dimethyl amine (1.18 g, 10 mmol, 40 wt % in water) and triethylamine (1.5 mL, 10 mmol) were stirred together at room temperature for 30 min. The resulting slurry was diluted with ethyl acetate and filtered. The filter cake was washed with ethyl acetate and the combined filtrate was washed with water, dried (Na$_2$SO$_4$) and concentrated to give the title product as orange plates (1.78 g, 85% yield). $^1$HNMR (300 MHz, CDCl$_3$) δ: 8.02 (1H, dd, J=8.05, 1.46 Hz), 7.87 (1H, dd, J=7.32, 1.47 Hz), 7.79–7.76 (2H, m), 2.86 (6H, s). LCMS calcd for C$_9$H$_{11}$N$_2$O$_2$S (M+H): 211.05; found: 211.09.

Intermediate 25

3-(2-Dimethylsulfamoyl-phenyl)-5-ethoxycarbonylmethyl-2-methyl-2,5-dihydro-[1,2,4]oxadiazole-5-carboxylic acid ethyl ester. To a solution of 2-cyano-N,N-dimethyl-benzenesulfonamide (4.68 g, 22.3 mmol) in ethanol/water (1:1, 150 mL) was added N-methylhydroxylamine hydrochloride (3.72 g, 44.6 mmol) followed by sodium carbonate (2.36 g, 22.3 mmol). The resulting mixture was stirred at 90° C. for 8 h then concentrated. The residue was triturated with MeOH/CHCl$_3$ (10%) and filtered. The solution was concentrated leaving an orange residue that was dissolved in ethanol (50 mL). Added to this solution was diethyl acetylene-dicarboxylate (3.6 mL, 22.3 mmol) and the resulting mixture stirred at room temp for 30 min. The mixture was concentrated and purified by flash chromatography (25% to 50% EtOAc/Hexanes) to give the title product as a yellow oil (5.57 g, 58% over two steps). $^1$HNMR (300 MHz, CDCl$_3$) δ: 7.93–7.87 (1H, m), 7.66–7.60 (2H, m), 7.57–7.51 (1H, m), 4.39–4.22 (2H,m), 4.16 (q, 2H, J=7.20 Hz), 3.40 (1H, d, J=16.47 Hz), 3.15 (1H, d, J=16.47 Hz), 3.00 (3H, s), 2.82 (6H, s), 1.24 (6H, td, J=6.95, 1.46 Hz). LCMS calcd for C$_{18}$H$_{26}$N$_3$O$_7$S (M+H): 428.14; found: 428.10.

Intermediate 26

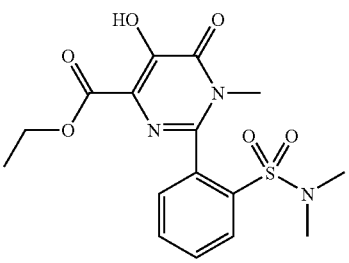

2-(2-Dimethylsulfamoyl-phenyl)-5-hydroxy-1-methyl-6-oxo-1,6-dihydro-pyrimidine-4-carboxylic acid ethyl ester. A solution of 3-(2-dimethylsulfamoyl-phenyl)-5-ethoxycarbonylmethyl-2-methyl-2,5-dihydro-[1,2,4]oxadiazole-5-carboxylic acid ethyl ester (5.57 g, 13 mmol) in xylenes (50 mL) was stirred at 140° C. for 8 h then cooled to room temperature. Hexanes (30 mL) was added and the mixture was stored at 5° C. for 18 h. The solution was filtered to give the title product as a yellow powder (2.47 g, 50% yield). $^1$HNMR (300 MHz, CDCl$_3$) δ: 10.63 (1H, s), 7.97–7.93 (1H, m), 7.73–7.64 (2H, m), 7.41–7.38 (1H, m), 4.58–4.47 (1H, m), 4.39–4.28 (1H, m), 3.24 (3H, s), 2.78 (6H, s), 1.32 (3H, t, J=6.95 Hz). LCMS calcd for C$_{16}$H$_{20}$N$_3$O$_6$S (M+H): 382.10; found: 382.08.

EXAMPLE 49

N-(4-fluorobenzyl)-2-(2-dimethylsulfamoylphenyl)-5-hydroxy-1-methyl-6-oxo-1,6-dihydropyrimidine-4-carboxamide. Prepared according to the procedure described for example 2 from 2-(2-dimethylsulfamoyl-phenyl)-5-hydroxy-1-methyl-6-oxo-1,6-dihydro-pyrimidine-4-carboxylic acid ethyl ester (0.076 g, 0.2mmol), and 4-fluorobenzylamine (0.11 mL, 1.0 mmol). The title product was obtained as white needles (0.0549 g, 60% yield). $^1$HNMR (500 MHz, CDCl$_3$) δ: 12.08 (1H, s), 7.91 (1H, d, J=7.33 Hz), 7.71–7.66 (3H, m), 7.37 (1H, dd, J=7.32, 1.83 Hz), 7.22 (2H, q, J=5.50 Hz), 7.00 (2H, t, J=8.55 Hz), 4.62 (1H, dd, J=15.26, 7.02 Hz), 4.40 (1H, dd, J=14.64, 5.49 Hz), 3.23 (3H, s), 2.64 (6H, s). HRMS (ESI) calcd for $C_{21}H_{22}FSN_4O_5$ (M+H): 461.1295; found: 461.1300.

EXAMPLE 50

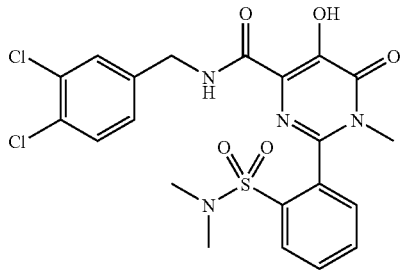

N-(3,4-dichlorobenzyl)-2-(2-dimethylsulfamoylphenyl)-5-hydroxy-1-methyl-6-oxo-1,6-dihydropyrimidine-4-carboxamide. Prepared according to the procedure described for example 2 from 2-(2-dimethylsulfamoyl-phenyl)-5-hydroxy-1-methyl-6-oxo-1,6-dihydro-pyrimidine-4-carboxylic acid ethyl ester (0.076 g, 0.2 mmol) and 3,4-dichlorobenzylamine (0.13 mL, 1.0 mmol). The title product was obtained as white needles (0.0569 g, 56% yield). $^1$HNMR (500 MHz, CDCl$_3$) δ: 11.93 (1H, s), 7.91 (1H, dd, J=7.32 Hz), 7.74 (1H, t, J=5.80 Hz), 7.72–7.67 (2H, m), 7.38 (2H), d, J=7.93 Hz), 7.32 (1H, d, J=1.83Hz), 7.11 (1H, dd, J=8.24, 1.83 Hz), 4.60 (1H, dd, J=15.26, 7.02 Hz), 4.41 (1H, dd, J=15.26, 5.80 Hz), 3.24 (3H, s), 2.69 (6H, s). HRMS (ESI) calcd for $C_{21}H_{21}SCl_2N_4O_5$ (M+H): 511.0610; found: 511.0612.

EXAMPLE 51

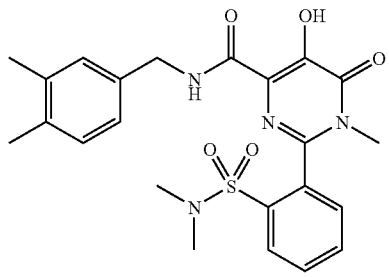

N-(3,4-dimethylbenzyl)-2-(2-dimethylsulfamoylphenyl)-5-hydroxy-1-methyl-6-oxo-1,6-dihydropyrimidine-4-carboxamide. Prepared according to the procedure described for example 2 from 2-(2-dimethylsulfamoyl-phenyl)-5-hydroxy-1-methyl-6-oxo-1,6-dihydro-pyrimidine-4-carboxylic acid ethyl ester (0.076 g, 0.2 mmol) and 3,4-dimethylbenzylamine (0.14 mL, 1.0 mmol). The title product was obtained as white needles (0.0560 g, 60% yield). $^1$HNMR (500 MHz, CDCl$_3$) δ: 12.19 (1H, s), 7.91 (1H, dd, J=7.48, 1.68 Hz), 7.71–7.65 (2H, m), 7.61 (1H, m), 7.36 (1H, dd, J=7.48, 1.68 Hz), 7.07 (1H, d, J=7.33 Hz) 7.00 (1H, s), 6.96 (1H, d, J=7.63 Hz), 4.57 (1H, dd, J=14.65, 7.02 Hz), 4.37 (1H, dd, J=14.65 Hz), 3.23 (3H, s), 2.63 (6H, s), 2.22 (6H, s). HRMS (ESI) calcd for $C_{23}H_{27}SN_4O_5$ (M+H): 471.1702; found 471.1708.

EXAMPLE 52

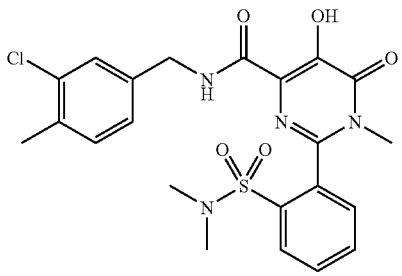

N-(3-chloro-4-methylbenzyl)-2-(2-dimethylsulfamoylphenyl)-5-hydroxy-1-methyl-6-oxo-1,6-dihydropyrimidine-4-carboxamide. Prepared according to the procedure described for example 2 from 2-(2-dimethylsulfamoyl-phenyl)-5-hydroxy-1-methyl-6-oxo-1,6-dihydro-pyrimidine-4-carboxylic acid ethyl ester (0.076 g, 0.2 mmol) and 3-chloro-4-methylbenzylamine (0.14 mL, 1.0 mmol). The title product was obtained as white needles (0.0601 g, 61% yield). $^1$HNMR (500 MHz, CDCl$_3$) δ: 12.05 (1H, s), 7.92 (1H, dd, J=7.47, 1.83 Hz), 7.72–7.66 (3H, m), 7.38 (1H, dd, J=7.17, 2.29 Hz), 7.19 (1H, s), 7.16 (1H, d, J=7.63 Hz), 7.04 (1H, d, J=7.63 Hz), 4.61 (1H, dd, J=14.95, 7.02 Hz), 4.36 (1H, dd, J=14.96, 5.19 Hz), 3.24 (3H, s), 2.66 (6H, s), 2.32 (3H, s). HRMS (ESI) calcd for $C_{22}H_{24}ClN_4O_5S$ (M+H): 491.1156; found: 491.1159.

EXAMPLES 53–105

Examples 53–105 were prepared according to the procedures described for examples 1–52.

| Example | Structure | Name and Analytical data |
|---|---|---|
| 53 | 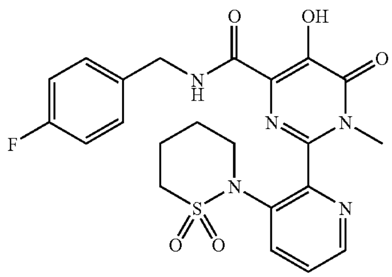 | N-(4-fluorobenzyl)-5-hydroxy-2-(3-[2-(1,1-Dioxo-1$\lambda^6$-[1,2]thiazinan-2-yl)-pyridin-2-yl]-)-1-methyl-6-oxo-1,6-dihydropyrimidine-4-carboxamide: $^1$H NMR (500 MHz, CDCl$_3$) δ: 12.31 (1H, br s), 8.64 (1H, dd, J=4.6, 1.5 Hz), 7.97 (1H, dd, J=8.2, 1.2 Hz), 7.50 (1H, dd, J= 8.2, 4.9 Hz), 7.26 (2H, dd, J=8.8, 5.2 Hz), 7.00 (2H, t, J=8.6 Hz), 4.53 (2H, d, J=4.6 Hz), 3.54–3.45 (2H, m), 3.41 (3H, s), 2.96–2.88 (2H, m), 2.21–2.15 (2H, m), 1.53–1.44 (2H, m). HRMS calcd for C$_{22}$H$_{23}$FN$_5$O$_5$S (M + H): 488.1404; found: 488.1395. Anal. Calcd for C$_{22}$H$_{22}$FN$_5$O$_5$S •0.25 CF$_3$CO$_2$H: C, 52.37; H, 4.35; N, 13.57; found: C, 52.47; H, 4.56; N, 13.46, |
| 54 | 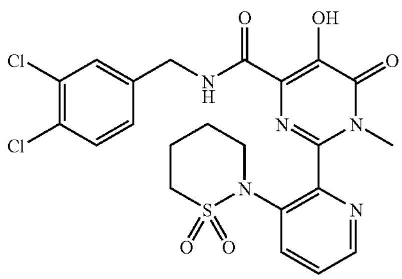 | N-(3,4-dichlorobenzyl)-5-hydroxy-2-(3-[2-(1,1-Dioxo-1$\lambda^6$-[1,2]thiazinan-2-yl)-pyridin-2-yl]-)-1-methyl-6-oxo-1,6-dihydropyrimidine-4-carboxamide: $^1$H NMR (500 MHz, CDCl$_3$) δ: 12.05 (1H, s), 8.64 (1H, dd, J=4.9, 1.5 Hz), 7.97 (1H, dd, J=8.2, 1.5 Hz), 7.49 (1H, dd, J=8.2, 4.9 Hz), 7.39 (1H, d, J=8.2 Hz), 7.37 (1H, J= 1.8 Hz), 7.14 (1H, dd, J=8.2, 1.8 Hz), 4.52 (2H, d, J=4.9 Hz), 3.55–3.48 (2H, m), 3.42 (3H, s), 3.00–2.94 (2H, m), 2.25–2.20 (2H, m), 1.61–1.54 (2H, m). HRMS calcd for C$_{22}$H$_{22}$Cl$_2$N$_5$O$_5$S (M + H): 538.0719; found: 538.0717. |
| 55 | 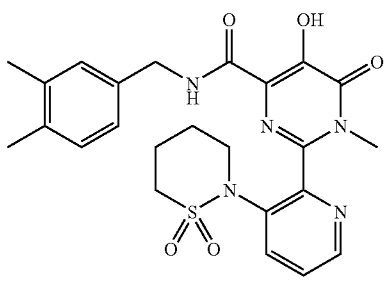 | N-(3,4-dimethylbenzyl)-5-hydroxy-2-(3-[2-(1,1-Dioxo-1$\lambda^6$-[1,2]thiazinan-2-yl)-pyridin-2-yl]-)-1-methyl-6-oxo-1,6-dihydropyrimidine-4-carboxamide: $^1$H NMR (500 MHz, CDCl$_3$) δ: 12.27 (1H, s), 8.63 (1H, dd, J=4.6, 1.2 Hz), 7.95 (1H, dd, J=8.2, 1.2 Hz), 7.75 (1H, br s), 7.48 (1H, dd, J=8.2, 4.6 Hz), 7.06 (1H, d, J=7.6 Hz), 7.03 (1H, d, J=1.5 Hz), 6.99 (1H, dd, J= 7.6, 1.5 Hz), 4.49 (2H, d, J=4.3 Hz), 3.54–3.47 (2H, m), 3.41 (3H, s), 2.93–2.88 (2H, m), 2.22 (6H, s), 2.19–2.14 (2H, m), 1.49–1.44 (2H, m). HRMS calcd for C$_{24}$H$_{28}$N$_5$O$_5$S (M + H): 498.1811; found: 498.1820. |
| 56 | 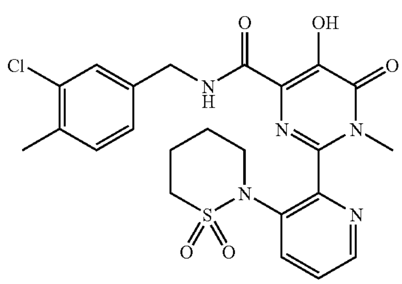 | N-(3-chloro4-methylbenzyl)-5-hydroxy-2-(3-[2-(1,1-Dioxo-1$\lambda^6$-[1,2]thiazinan-2-yl)-pyridin-2-yl]-)-1-methyl-6-oxo-1,6-dihydropyrimidine-4-carboxamide: $^1$H NMR (500 MHz, CDCl$_3$) δ: 8.59 (1H, dd, J=4.6, 1.2 Hz), 7.93 (1H, dd, J=8.2, 1.2 Hz), 7.47 (1H, dd, J=8.2, 4.6 Hz), 7.20 (1H, d, J=1.2 Hz), 7.13 (1H, d, J=7.6 Hz), 7.03 (1H, dd, J=7.6, 1.2 Hz), 4.48–4.43 (2H, br s), 3.53–3.46 (2H, m), 3.36 (3H, s), 3.34–3.33 (2H, m), 2.94–2.88 (2H, m), 2.28 (3H, s), 2.18–2.13 (2H, m), 1.53–1.44 (2H, m). HRMS calcd for C$_{23}$H$_{25}$ClN$_5$O$_5$S (M + H): 518.1265; found: 518.1272. |
| 57 | 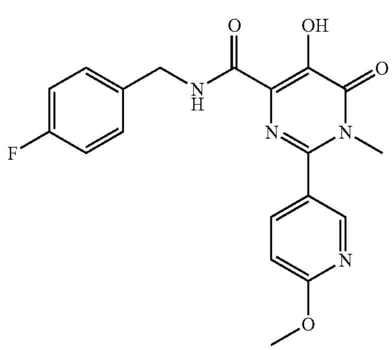 | N-(4-fluorobenzyl)-5-hydroxy-2-(6-methoxypyridin-3-yl)-1-methyl-6-oxo-1,6-dihydropyrimidine-4-carboxamide: $^1$H NMR (500 MHz, MeOD) δ: 8.44 (1H, s), 7.94 (1H, d, J=8.5 Hz), 7.38 (2H, dd, J=5.6, 2.1 Hz), 7.05 (2H, t, J=8.5 Hz), 6.93 (1H, d, J=8.5 Hz), 4.54 (2H, s), 4.00 (3H, s), 3.52 (3H, s). HRMS (M + H) calcd for C$_{19}$H$_{18}$FN$_4$O$_4$: 385.13122; found: 385.1312. |

-continued

| Example | Structure | Name and Analytical data |
|---|---|---|
| 58 | 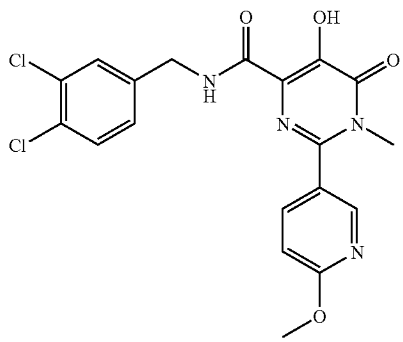 | N-(3,4-dichlorobenzyl)-5-hydroxy-2-(6-methoxypyridin-3-yl)-1-methyl-6-oxo-1,6-dihydropyrimidine-4-carboxamide: $^1$H NMR (500 MHz, MeOD) δ: 8.45 (1H, s), 7.95 (1H, d, J=7.3 Hz), 7.53 (1H, s), 7.48 (1H, d, J=7.9 Hz), 7.31 (1H, d, J=8.2 Hz), 6.93 (1H, d, J=8.5 Hz), 4.54 (2H, s), 4.00 (3H, s), 3.52 (3H, s). HRMS (M + H) calcd for $C_{19}H_{17}Cl_2N_4O_4$: 435.0627; found: 435.0617. |
| 59 | 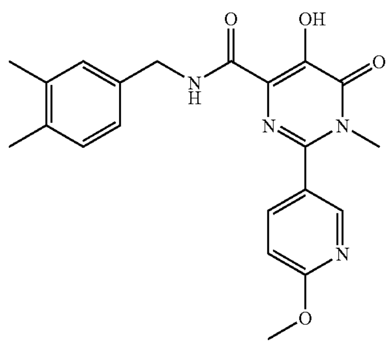 | N-(3,4-dimethylbenzyl)-5-hydroxy-2-(6-methoxypyridin-3-yl)-1-methyl-6-oxo-1,6-dihydropyrimidine-4-carboxamide: $^1$H NMR (500 MHz, MeOD) δ: 8.43 (1H, s), 7.93 (1H, d, J=8.2 Hz), 7.12 (1H, s), 7.09–7.05 (2H, m), 6.92 (1H, d, J=8.2 Hz), 4.49 (2H, s), 4.00 (3H, s), 3.52 (3H, s), 2.25 (3H, s), 2.24 (3H, s). HRMS (M + H) calcd for $C_{21}H_{23}N_4O_4$: 395.17194; found: 395.1718. |
| 60 | 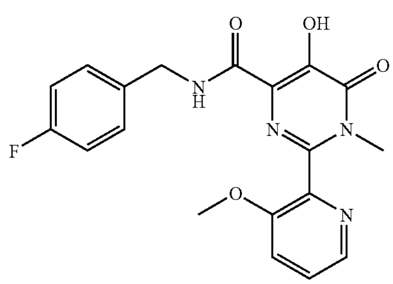 | N-(4-fluorobenzyl)-5-hydroxy-2-(3-methoxypyridin-2-yl)-1-methyl-6-oxo-1,6-dihydropyrimidine-4-carboxamide: $^1$H NMR (500 MHz, CDCl$_3$) δ: 12.25 (1H, br s), 8.32 (1H, d, J=4.6 Hz), 7.85 (1H, s), 7.47 (1H, dd, J=8.5, 4.6 Hz), 7.39 (1H, d, J=8.2 Hz), 7.27 (2H, dd, J=8.5, 5.2 Hz), 6.99 (2H, t, J=8.5 Hz), 4.52 (2H, d, J=6.1 Hz), 3.86 (3H, s), 3.32 (3H, s). HRMS calcd for $C_{19}H_{18}N_4O_4$ (M + H): 385.1312; found: 385.1316. |
| 61 | 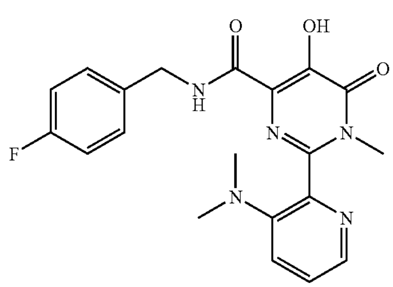 | N-(4-fluorobenzyl)-2-(3-(dimethylamino)pyridin-2-yl)-5-hydroxy-1-methyl-6-oxo-1,6-dihydropyrimidine-4-carboxamide: $^1$H NMR (500 MHz, CDCl$_3$) δ: 8.36 (1H, s), 8.18 (1H, bs), 7.69 (1H, d, J=8.5 Hz), 7.66–7.64 (1H, m), 7.31 (2H, dd, J=8.4, 5.3 Hz), 6.99 (2H, t, J=8.7 Hz), 4.54 (2H, d, J=4.9 Hz), 3.53 (3H, s), 2.81 (6H, s). HRMS (M + H) calcd for $C_{20}H_{21}FN_5O_3$: 398.16285; found: 398.1626. |
| 62 | 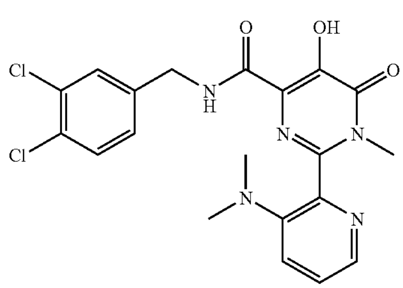 | N-(3,4-dichlorobenzyl)-2-(3-(dimethylamino)pyridin-2-yl)-5-hydroxy-1-methyl-6-oxo-1,6-dihydropyrimidine-4-carboxamide: $^1$H NMR (500 MHz, CDCl$_3$) δ: 8.37 (2H, bs), 7.85 (1H, d, J=8.5 Hz), 7.79 (1H, d, J=7.3 Hz), 7.43 (1H, s), 7.38 (1H, d, J=8.2 Hz), 7.19 (1H, d, J=8.2 Hz), 4.52 (2H, s), 3.38 (3H, s), 2.88 (6H, s). HRMS (M + H) calcd for $C_{20}H_{20}Cl_2N_5O_3$: 448.09433; found: 448.0938. |

| Example | Structure | Name and Analytical data |
|---|---|---|
| 63 | 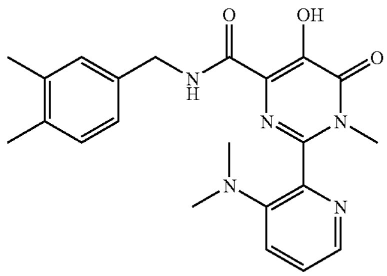 | N-(3,4-dimethylbenzyl)-2-(3-(dimethylamino)pyridin-2-yl)-5-hydroxy-1-methyl-6-oxo-1,6-dihydropyrimidine-4-carboxamide: $^1$H NMR (500 MHz, CDCl$_3$) δ: 8.30 (1H, s), 8.07 (1H, bs), 7.52–7.46 (2H, m), 7.09–7.04 (3H, m), 4.50 (2H, d, J=5.5 Hz), 3.34 (3H, s), 2.74 (6H, s), 2.22 (3H, s), 2.21 (3H, s). HRMS (M + H) calcd for C$_{22}$H$_{26}$N$_5$O$_3$: 408.20357; found: 408.2035. |
| 64 | 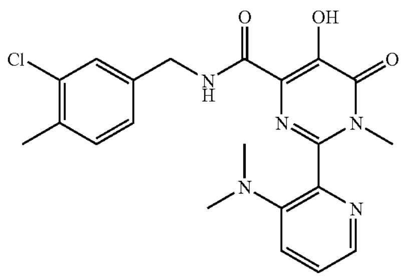 | N-(3-chloro-4-methylbenzyl)-2-(3-(dimethylamino)pyridin-2-yl)-5-hydroxy-1-methyl-6-oxo-1,6-dihydropyrimidine-4-carboxamide: $^1$H NMR (500 MHz, CDCl$_3$) δ: 8.37 (1H, s), 8.20 (1H, bs), 7.67–7.62 (2H, m), 7.31 (1H, s), 7.17–7.13 (2H, m), 4.51 (2H, s), 3.36 (3H, s), 2.81 (6H, s), 2.32 (3H, s). HRMS (M + H) calcd for C$_{21}$H$_{23}$ClN$_5$O$_3$: 428.14895; found: 428.1485. |
| 65 | 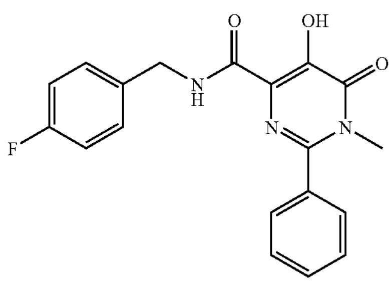 | N-(4-fluorobenzyl)-5-hydroxy-1-methyl-6-oxo-2-phenyl-1,6-dihydropyrimidine-4-carboxamide: $^1$H NMR (500 MHz, CDCl$_3$) δ: 12.14 (1H, br s), 7.91 (1H, br s), 7.52–7.47 (3H, m), 7.43–7.41 (2H, m), 7.29–7.26 (2H, m), 7.03–7.00 (2H, m), 4.55 (2H, d, J=6.4 Hz), 3.45 (3H, s). HRMS calcd for C$_{19}$H$_{17}$FN$_3$O$_3$ (M + H): 354.1254; found: 354.1253. |
| 66 | 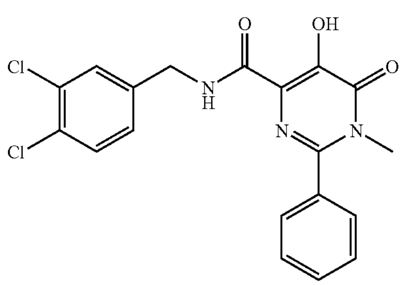 | N-(3,4-dichlorobenzyl)-5-hydroxy-1-methyl-6-oxo-2-phenyl-1,6-dihydropyrimidine-4-carboxamide: $^1$H NMR (500 MHz, CDCl$_3$) δ: 11.99 (1H, br s), 7.95 (1H, br s), 7.53–7.48 (3H, m), 7.44–7.39 (4H, m), 7.16–7.14 (1H, m), 4.53 (2H, d, J=6.4 Hz), 3.45 (3H, s). HRMS calcd for C$_{19}$H$_{16}$Cl$_2$N$_3$O$_3$ (M + H): 404.0569; found: 404.0570. |
| 67 | 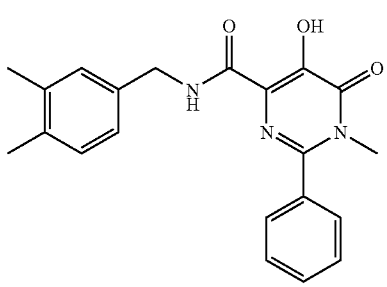 | N-(3,4-dimethylbenzyl)-5-hydroxy-1-methyl-6-oxo-2-phenyl-1,6-dihydropyrimidine-4-carboxamide: $^1$H NMR (500 MHz, CDCl$_3$) δ: 12.25 (1H, s), 7.86 (1H, br s), 7.51–7.46 (3H, m), 7.42–7.40 (2H, m), 7.10–7.02 (3H, m), 4.51 (2H, d, J=6.1 Hz), 3.45 (3H, s), 2.23 (3H, s), 2.22 (3H, s). HRMS calcd for C$_{21}$H$_{22}$N$_3$O$_3$ (M + H): 364.1661; found: 364.1662. |

| Example | Structure | Name and Analytical data |
|---|---|---|
| 68 | 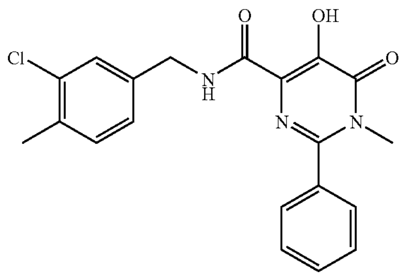 | N-(3-chloro-4-methylbenzyl)-5-hydroxy-1-methyl-6-oxo-2-phenyl-1,6-dihydropyrimidine-4-carboxamide: $^1$H NMR (500 MHz, CDCl$_3$) δ: 12.13 (1H, s), 7.90 (1H, br s), 7.52–7.47 (3H, m), 7.44–7.41 (2H, m), 7.28–7.27 (1H, m), 7.19–7.17 (1H, m), 7.10–7.08 (1H, m), 4.52 (2H, d, J=6.4 Hz), 3.45 (3H, s), 2.33 (3H, s). HRMS calcd for C$_{20}$H$_{19}$ClN$_3$O$_3$ (M + H): 384.1115; found: 384.1124. |
| 69 | 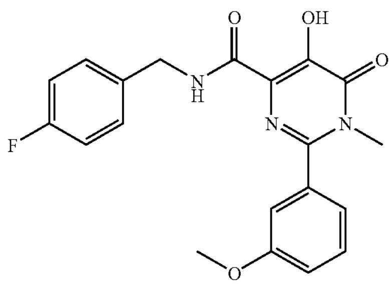 | N-(4-fluorobenzyl)-5-hydroxy-2-(3-methoxyphenyl)-1-methyl-6-oxo-1,6-dihydropyrimidine-4-carboxamide: HRMS calcd for C$_{20}$H$_{19}$FN$_3$O$_4$ (M + H): 384.1360; found: 384.1359. |
| 70 | 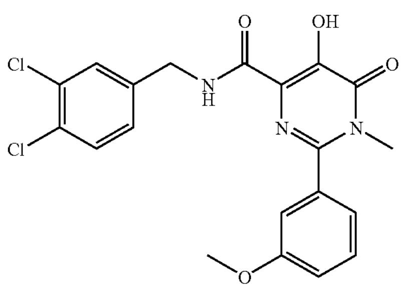 | N-(3,4-dichlorobenzyl)-5-hydroxy-2-(3-methoxyphenyl)-1-methyl-6-oxo-1,6-dihydropyrimidine-4-carboxamide: HRMS calcd for C$_{20}$H$_{18}$Cl$_2$N$_3$O$_4$ (M + H): 434.0675; found: 434.0667. |
| 71 | 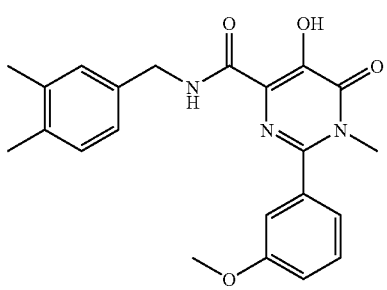 | N-(3,4-dimethylbenzyl)-5-hydroxy-2-(3-methoxyphenyl)-1-methyl-6-oxo-1,6-dihydropyrimidine-4-carboxamide: HRMS calcd for C$_{22}$H$_{24}$N$_3$O$_4$ (M + H): 394.1767; found: 394.1774. |
| 72 | 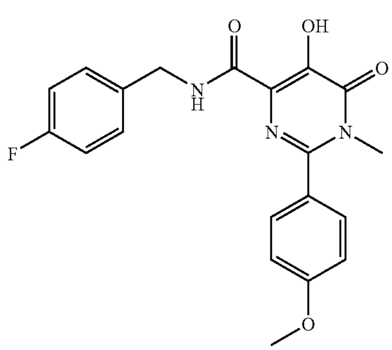 | N-(4-fluorobenzyl)-5-hydroxy-2-(4-methoxyphenyl)-1-methyl-6-oxo-1,6-dihydropyrimidine-4-carboxamide: HRMS calcd for C$_{20}$H$_{19}$FN$_3$O$_4$ (M + H): 384.1360; found: 384.1362. |

-continued

| Example | Structure | Name and Analytical data |
|---|---|---|
| 73 | 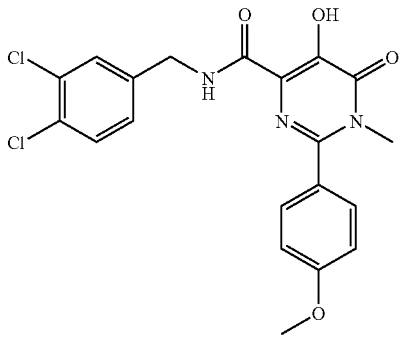 | N-(3,4-dichlorobenzyl)-5-hydroxy-2-(4-methoxyphenyl)-1-methyl-6-oxo-1,6-dihydropyrimidine-4-carboxamide: HRMS calcd for $C_{20}H_{18}Cl_2N_3O_4$ (M + H): 434.0675; found: 434.0671. |
| 74 | 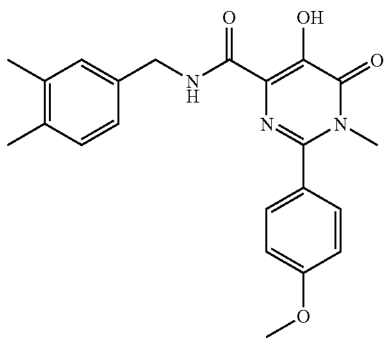 | N-(3,4-dimethylbenzyl)-5-hydroxy-2-(4-methoxyphenyl)-1-methyl-6-oxo-1,6-dihydropyrimidine-4-carboxamide: HRMS calcd for $C_{22}H_{24}N_3O_4$ (M + H): 394.1767; found: 394.1767. |
| 75 | 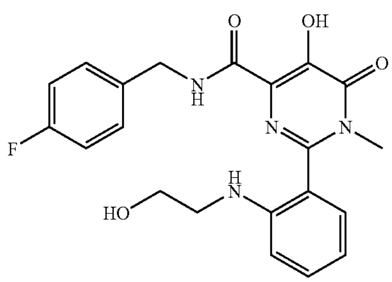 | N-(4-fluorobenzyl)-5-hydroxy-2-[2-(2-hydroxyethylamino)phenyl]-1-methyl-6-oxo-1,6-dihydropyrimidine-4-carboxylate: $^1$H NMR (500 MHz, CDCl$_3$) δ: 8.16 (1H, s), 7.43 (1H, t, J=7.5 Hz), 7.30 (2H, dd, J=7.9, 2.4 Hz), 7.12 (1H, d, J=7.3 Hz), 7.01–6.94 (4H, m), 4.51 (2H, d, J=5.5 Hz), 3.90 (2H, s), 3.42–3.36 (6H, m). HRMS (M + H) calcd for $C_{21}H_{22}FN_4O_4$: 413.16252; found: 413.1636. |
| 76 | 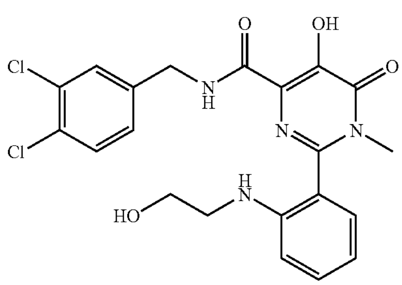 | N-(3,4-dichlorobenzyl)-5-hydroxy-2-(2-(2-hydroxyethylamino)phenyl)-1-methyl-6-oxo-1,6-dihydropyrimidine-4-carboxamide: $^1$H NMR (500 MHz, CDCl$_3$) δ: 8.34 (1H, bs), 7.47 (1H, t, J=7.3 Hz), 7.42 (1H, s), 7.36 (1H, d, J=8.4 Hz), 7.19–7.15 (2H, m), 7.09 (1H, d, J=7.9 Hz), 7.04 (1H, t, J=7.5 Hz), 4.46 (2H, d, J=5.5 Hz), 3.92 (2H, s), 3.43 (6H, s). (M + H) calcd for $C_{21}H_{21}Cl_2N_4O_4$: 463.0940; found: 463.0943. |
| 77 | 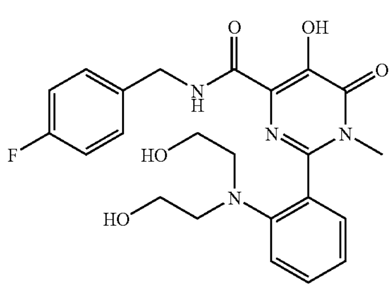 | N-(4-fluorobenzyl)-2-(2-(bis(2-hydroxyethyl)amino)phenyl)-5-hydroxy-1-methyl-6-oxo-1,6-dihydropyrimidine-4-carboxamide: $^1$H NMR (500 MHz, CDCl$_3$) δ: 8.17 (1H, t, J=6.0 Hz), 7.42 (1H, d, J=1.5 Hz), 7.40–7.37 (2H, m), 7.16 (1H, dd, J=8.1, 1.6 Hz), 7.10 (1H, d, J=8.7 Hz), 6.98 (1H, t, J=8.7 Hz), 6.89–6.86 (2H, m), 4.46 (2H, d, J=6.4 Hz), 3.88 (2H, s), 3.63 (2H, bs), 3.54 (2H, bs), 3.43 (3H, s), 3.37–3.35 (4H, m). HRMS (M + H) calcd for $C_{23}H_{26}FN_4O_5$: 457.18873; found: 457.1890. |

-continued

| Example | Structure | Name and Analytical data |
|---|---|---|
| 78 | 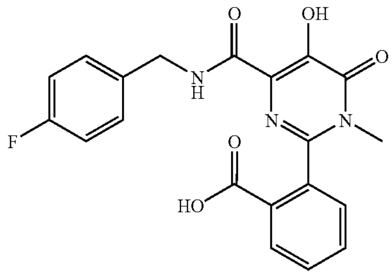 | 2-(4-((4-fluorobenzyl)carbamoyl)-5-hydroxy-1-methyl-6-oxo-1,6-dihydropyrimidin-2-yl)benzoic acid: $^1$H NMR (500 MHz, CDCl$_3$) δ: 12.14 (1H, bs), 8.20 (1H, d, J=7.3 Hz), 7.79 (1H, s), 7.71 (1H, t, J=7.3 Hz), 7.63 (1H, t, J=7.5 Hz), 7.35 (1H, d, J=7.3 Hz), 7.04–6.97 (3H, m), 4.50 (2H, s), 3.24 (3H, s). HRMS (M + H) calcd for C$_{20}$H$_{17}$FN$_3$O$_5$: 398.11523; found: 398.1147. |
| 79 | | 2-(4-((3,4-dichlorobenzyl)carbamoyl)-5-hydroxy-1-methyl-6-oxo-1,6-dihydropyrimidin-2-yl)benzoic acid: $^1$H NMR (500 MHz, CDCl$_3$) δ: 12.00 (1H, bs), 8.20 (1H, d, J=7.6 Hz), 7.83 (1H, s), 7.73 (1H, t, J=7.5 Hz), 7.64 (1H, t, J=7.3 Hz), 7.36 (3H, d, J=7.6 Hz), 7.13 (1H, d, J=7.9 Hz), 4.48 (2H, s), 3.25 (3H, s). HRMS (M + H) calcd for C$_{20}$H$_{16}$Cl$_2$N$_3$O$_5$: 448.04671; found: 448.0466. |
| 79 | | N-(4-fluorobenzyl)-2-(2-(dimethylamino)phenyl)-5-hydroxy-1-methyl-6-oxo-1,6-dihydropyrimidine-4-carboxamide: $^1$H NMR (500 MHz, CDCl$_3$) δ: 10.68 (1H, bs), 7.78 (1H, t, J=5.0 Hz), 7.64 (1H, t, J=7.5 Hz), 7.49 (1H, d, J=8.24 Hz), 7.44–7.41 (2H, m), 7.29–7.26 (2H, m), 7.00 (2H, t, J=8.5 Hz), 4.53 (2H, d, J=5.8 Hz), 3.33 (3H, s), 3.03 (6H, s). HRMS (M + H) calcd for C$_{21}$H$_{22}$FN$_4$O$_3$: 397.1676; found: 397.1677. |
| 80 | 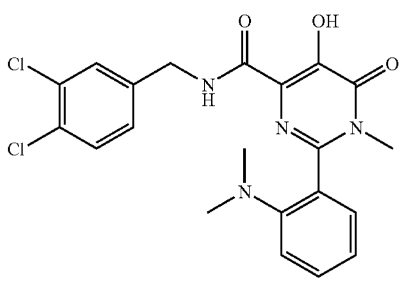 | N-(3,4-dichlorobenzyl)-2-(2-(dimethylamino)phenyl)-5-hydroxy-1-methyl-6-oxo-1,6-dihydropyrimidine-4-carboxamide: $^1$H NMR (500 MHz, CDCl$_3$) δ: 11.94 (1H, bs), 8.01 1H, s), 7.43 (1H, t, J=7.3 Hz), 7.40–7.38 (2H, m), 7.26 (1H, d, J=7.6 Hz), 7.16 (1H, dd, J=8.1, 1.7 Hz), 7.10–7.06 (2H, m), 4.52 (2H, s), 3.31 (3H, s), 2.64 (6H, s). HRMS (M + H) calcd for C$_{21}$H$_{21}$Cl$_2$N$_4$O$_3$: 447.09908; found: 447.0990. |
| 81 | 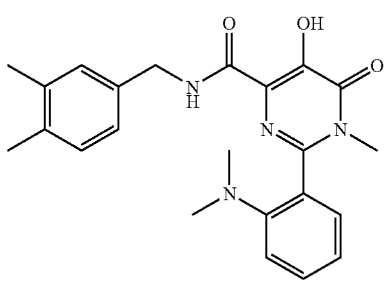 | N-(3,4-dimethylbenzyl)-2-(2-(dimethylamino)phenyl)-5-hydroxy-1-methyl-6-oxo-1,6-dihydropyrimidine-4-carboxamide: $^1$H NMR (500 MHz, CDCl$_3$) δ: 12.20 (1H, s), 7.42 (1H, t, J=7.2 Hz), 7.23 (1H, d, J=7.3 Hz), 7.10–7.03 (5H, m), 4.50 (2H, d, J=11.0 Hz), 3.31 (3H, s), 2.63 (6H, s), 2.23 (6H, s). HRMS (M + H) calcd for C$_{23}$H$_{27}$N$_4$O$_3$: 407.20833; found: 407.2088. |

-continued

| Example | Structure | Name and Analytical data |
|---|---|---|
| 82 | 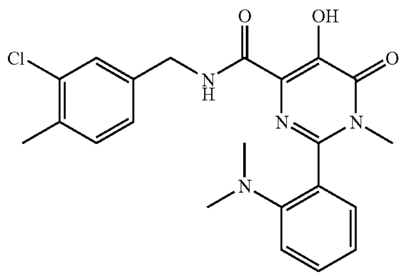 | N-(3-chloro-4-methylbenzyl)-2-(2-(dimethylamino)phenyl)-5-hydroxy-1-methyl-6-oxo-1,6-dihydropyrimidine-4-carboxamide: $^1$H NMR (500 MHz, CDCl$_3$) δ: 12.06 (1H, s), 7.95 (1H, s), 7.42 (1H, t, J=7.5 Hz), 7.28–7.25 (2H, m), 7.17 (1H, d, J=7.9 Hz), 7.10–7.04 (3H, m), 4.51 (2H, d, J=19.8 Hz), 3.31 (3H, s), 2.63 (6H, s), 2.33 (3H, s). HRMS (M + H) calcd for C$_{22}$H$_{24}$ClN$_4$O$_3$: 427.1537; found: 427.1540. |
| 83 | 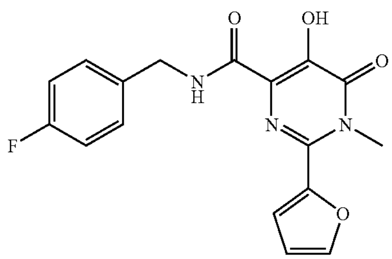 | N-(4-fluorobenzyl)-2-(furan-2-yl)-5-hydroxy-1-methyl-6-oxo-1,6-dihydropyrimidine-4-carboxamide: $^1$H NMR (500 MHz, MeOD) δ: 7.69 (1H, s), 7.44 (2H, td, J=5.3, 2.4 Hz), 7.40 (2H, td, J=5.5, 2.7 Hz), 7.14 (2H, t, J=8.5 Hz), 7.08–7.04 (3H, m), 6.61 (1H, dd, J=1.18, 1.5 Hz), 4.59 (2H, s), 4.02 (2H, s), 3.61 (3H, s). HRMS (M + H) calcd for C$_{17}$H$_{15}$FN$_3$O$_4$: 344.10467; found: 344.1059. |
| 84 | 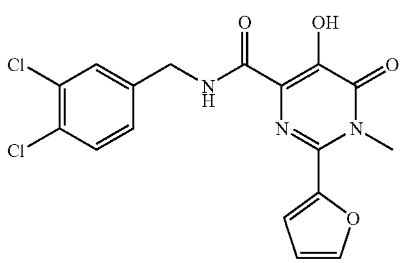 | N-(3,4-dichlorobenzyl)-2-(furan-2-yl)-5-hydroxy-1-methyl-6-oxo-1,6-dihydropyrimidine-4-carboxamide: $^1$H NMR (500 MHz, MeOD) δ: 7.79 (1H, s), 7.55 (1H, s), 7.50 (1H, d, J=8.2 Hz), 7.32 (1H, d, J=7.9 Hz), 7.28 (1H, s), 6.68 (1H, s), 4.57 (2H, s), 3.75 (3H, s). HRMS (M + H) calcd for C$_{17}$H$_{14}$Cl$_2$N$_3$O$_4$: 394.03615; found: 394.0358. |
| 86 | 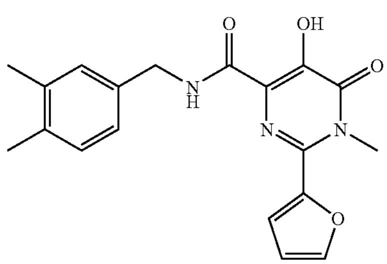 | N-(3,4-dimethylbenzyl)-2-(furan-2-yl)-5-hydroxy-1-methyl-6-oxo-1,6-dihydropyrimidine-4-carboxamide: $^1$H NMR (500 MHz, MeOD) δ: 7.77 (1H, s), 7.25 (1H, d, J=3.1 Hz), 7.14 (1H, s), 7.11–7.06 (2H, m), 6.66 (1H, dd, J=1.8, 1.5 Hz), 4.52 (2H, s), 3.74 (3H, s), 2.26 (3H, s), 2.25 (3H, s). HRMS (M + H) calcd for C$_{19}$H$_{20}$N$_3$O$_4$: 354.14539; found: 354.1462. |
| 87 | 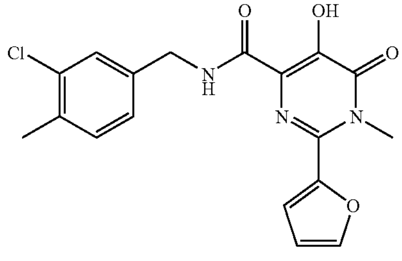 | N-(3-chloro-4-methylbenzyl)-2-(furan-2-yl)-5-hydroxy-1-methyl-6-oxo-1,6-dihydropyrimidine-4-carboxamide: $^1$H NMR (500 MHz, MeOD) δ: 7.78 (1H, s), 7.37 (1H, s), 7.28–7.25 (2H, m), 7.21 (1H, d, J=7.63 Hz), 6.67 (1H, s), 4.53 (2H, s), 3.75 (3H, s), 2.35 (3H, s). HRMS (M + H) calcd for C$_{18}$H$_{17}$ClN$_3$O$_4$: 374.09077; found: 374.0913. |

| Example | Structure | Name and Analytical data |
|---|---|---|
| 88 | 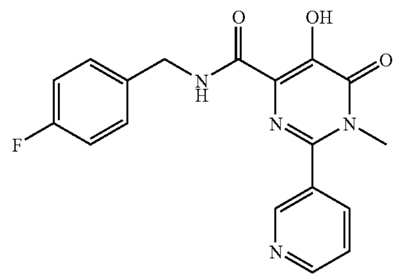 | N-(4-fluorobenzyl)-5-hydroxy-1-methyl-6-oxo-2-(pyridin-3-yl)-1,6-dihydropyrimidine-4-carboxamide: $^1$H NMR (300 MHz, CDCl$_3$) δ: 11.35 (1H, bs), 9.23 (1H, s), 8.99 (1H, d, J=5.1 Hz), 8.47 (1H, d, J=7.7 Hz), 8.00 (1H, dd, J= 8.0, 2.6 Hz), 7.87 (1H, t, J=5.8 Hz), 7.28 (2H, dd, J=8.8, 3.3 Hz), 7.00 (2H, t, J=8.6 Hz), 4.56 (2H, d, J=6.2 Hz), 3.55 (3H, s). HRMS (M + H) calcd for C$_{18}$H$_{16}$FN$_4$O$_3$: 355.12065; found: 355.1207. |
| 89 | 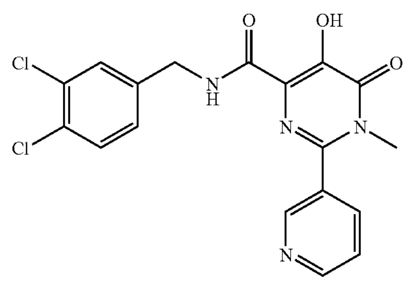 | N-(3,4-dichlorobenzyl)-5-hydroxy-1-methyl-6-oxo-2-(pyridin-3-yl)-1,6-dihydropyrimidine-4-carboxamide: $^1$H NMR (500 MHz, CDCl$_3$) δ: 13.02 (1H, bs), 8.95 (1H, s), 8.82 (1H, s), 8.10 (1H, s), 7.91 (1H, s), 7.71 (1H, s), 7.43–7.38 (2H, m), 7.17–7.13 (1H, m), 4.55 (2H, s), 3.51 (3H, s). HRMS (M + H) calcd for C$_{18}$H$_{15}$Cl$_2$N$_4$O$_3$: 405.05213; found: 405.0514. |
| 90 | 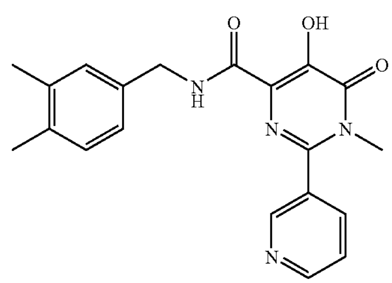 | N-(3,4-dimethylbenzyl)-5-hydroxy-1-methyl-6-oxo-2-(pyridin-3-yl)-1,6-dihydropyrimidine-4-carboxamide: $^1$H NMR (500 MHz, CDCl$_3$) δ: 12.39 (1H, bs), 8.96 (1H, s), 8.86 (1H, s), 8.17 (1H, d, J=7.3 Hz), 7.77 (2H, s), 7.13–7.00 (3H, m), 4.52 (2H, d, J=4.0 Hz), 3.51 (3H, s), 2.23 (3H, s), 2.22 (3H, s). HRMS (M + H) calcd for C$_{20}$H$_{21}$N$_4$O$_3$: 365.16138; found: 365.1612. |
| 91 | 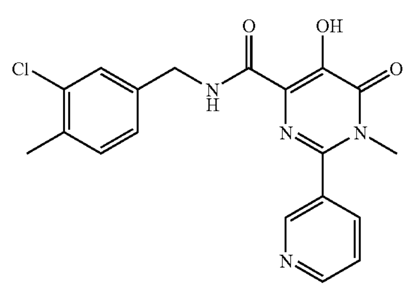 | N-(3-chloro-4-methylbenzyl)-5-hydroxy-1-methyl-6-oxo-2-(pyridin-3-yl)-1,6-dihydropyrimidine-4-carboxamide: $^1$H NMR (500 MHz, CDCl$_3$) δ: 12.37 (1H, bs), 9.01 (1H, s), 8.87 (1H, s), 8.23 (1H, d, J=6.7 Hz), 7.85 (1H, s), 7.80 (1H, s), 7.26 (1H, s), 7.17 (1H, d, J= 7.6 Hz), 7.10 (1H, d, J=8.8 Hz), 4.52 (2H, s), 3.51 (3H, s), 2.32 (3H, s). HRMS (M + H) calcd for C$_{19}$H$_{18}$ClN$_4$O$_3$: 385.10675; found: 385.1064. |
| 92 | 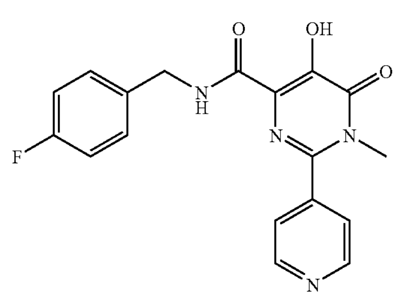 | N-(4-fluorobenzyl)-5-hydroxy-1-methyl-6-oxo-2-(pyridin-4-yl)-1,6-dihydropyrimidine-4-carboxamide: $^1$H NMR (500 MHz, DMSO) δ: 12.61 (1H, bs), 9.42 (1H, t, J=6.4 Hz), 8.81 (2H, d, J=6.1 Hz), 7.77 (2H, d, J=6.1 Hz), 7.37–7.34 (2H, m), 7.16–7.13 (2H, m), 4.44 (2H, d, J=6.41 Hz), 3.32 (3H, s). HRMS (M + H) calcd for C$_{18}$H$_{16}$FN$_4$O$_3$: 355.12065; found: 355.1206. |

| Example | Structure | Name and Analytical data |
|---|---|---|
| 93 | 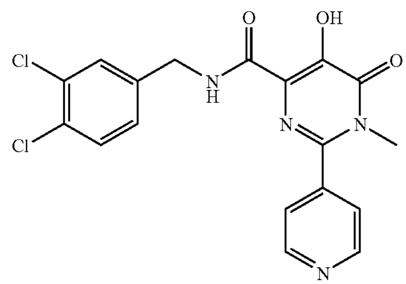 | N-(3,4-dichlorobenzyl)-5-hydroxy-1-methyl-6-oxo-2-(pyridin-4-yl)-1,6-dihydropyrimidine-4-carboxamide: $^1$H NMR (500 MHz, CDCl$_3$) δ: 12.18 (1H, s), 8.79 (2H, d, J=4.3 Hz), 7.90 (1H, bs), 7.42–7.39 (4H, m), 7.16 (1H, d, J=7.9 Hz), 4.54 (2H, d, J=6.1 Hz), 3.46 (3H, s). HRMS (M + H) calcd for C$_{18}$H$_{15}$Cl$_2$N$_4$O$_3$: 405.05213; found: 405.0540. |
| 94 | 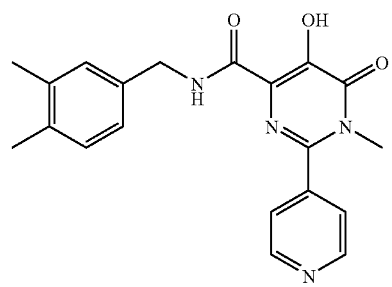 | N-(3,4-dimethylbenzyl)-5-hydroxy-1-methyl-6-oxo-2-(pyridin-4-yl)-1,6-dihydropyrimidine-4-carboxamide: $^1$H NMR (500 MHz, CDCl$_3$) δ: 13.30 (1H, bs), 8.90 (2H, d, J=4.9 Hz), 7.73 (2H, d, J=5.2 Hz), 7.68 (1H, s), 7.11–7.02 (3H, m), 4.52 (2H, d, J=5.8 Hz), 3.48 (3H, s), 2.23 (6H, s). HRMS (M + H) calcd for C$_{20}$H$_{21}$N$_4$O$_3$: 365.16138; found: 365.1610. |
| 95 | 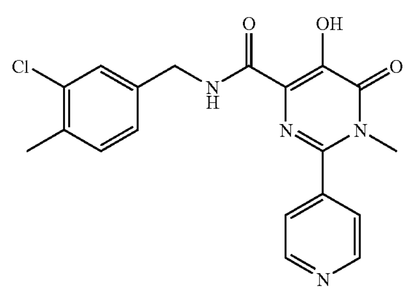 | N-(3-chloro-4-methylbenzyl)-5-hydroxy-1-methyl-6-oxo-2-(pyridin-4-yl)-1,6-dihydropyrimidine-4-carboxamide: $^1$H NMR (500 MHz, CDCl$_3$) δ: 12.30 (1H, s), 8.79 (2H, d, J=4.6 Hz), 7.83 (1H, bs), 7.41 (2H, d, J=4.9 Hz), 7.28 (1H, s), 7.18 (1H, d, J=7.6 Hz), 7.10 (1H, d, J=7.6 Hz), 4.53 (2H, d, J=6.1 Hz), 3.46 (3H, s), 2.33 (3H, s). HRMS (M + H) calcd for C$_{19}$H$_{18}$ClN$_4$O$_3$: 385.10675; found: 385.1071. |
| 96 | 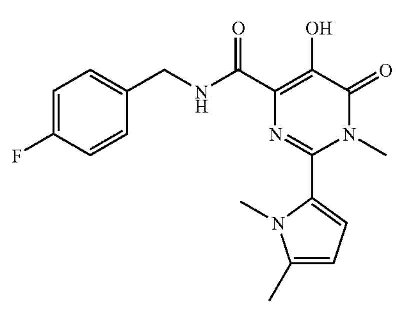 | N-(4-fluorobenzyl)-2-(1,5-dimethyl-1H-pyrrol-2-yl)-5-hydroxy-1-methyl-6-oxo-1,6-dihydropyrimidine-4-carboxamide: $^1$H NMR (300 MHz, CDCl$_3$) δ: 12.04 (1H, s), 7.87 (1H, t, J=5.8 Hz), 7.30–7.25 (2H, m), 7.02 (2H, t, J=8.6 Hz), 6.29 (1H, d, J=3.7 Hz), 5.98 (1H, dd, J=3.7, 0.7 Hz), 4.55 (2H, d, J=6.2 Hz), 3.56 (3H, s), 3.46 (3H, s), 2.26 (3H, s). HRMS (M + H) calcd for C$_{19}$H$_{20}$FN$_4$O$_3$: 371.15195; found: 371.1511. |
| 97 | 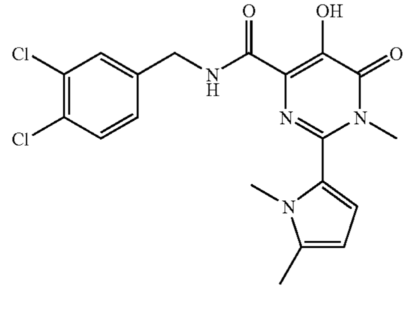 | N-(3,4-dichlorobenzyl)-2-(1,5-dimethyl-1H-pyrrol-2-yl)-5-hydroxy-1-methyl-6-oxo-1,6-dihydropyrimidine-4-carboxamide: $^1$H NMR (300 MHz, CDCl$_3$) δ: 11.90 (1H, s), 7.93 (1H, t, J=6.0 Hz), 7.42–7.39 (2H, m), 7.15 (2H, dd, J=8.4, 2.2 Hz), 6.30 (1H, d, J=4.0 Hz), 5.99 (1H, dd, J=3.7, 0.7 Hz), 4.53 (2H, d, J=6.6 Hz), 3.56 (3H, s), 3.48 (3H, s), 2.27 (3H, s). HRMS (M + H) calcd for C$_{19}$H$_{19}$Cl$_2$N$_4$O$_3$: 421.08343; found: 421.0840. |

-continued

| Example | Structure | Name and Analytical data |
|---|---|---|
| 98 | 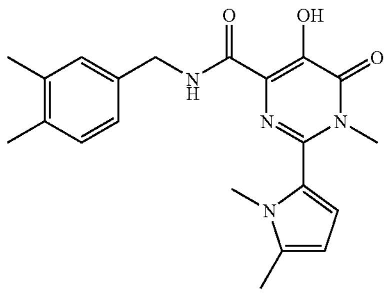 | N-(3,4-dimethylbenzyl)-2-(1,5-dimethyl-1H-pyrrol-2-yl)-5-hydroxy-1-methyl-6-oxo-1,6-dihydropyrimidine-4-carboxamide: $^1$H NMR (500 MHz, CDCl$_3$) δ: 12.15 (1H, s), 7.83 (1H, d, J=5.0 Hz), 7.09 (1H, d, J=7.6 Hz), 7.07 (1H, s), 7.03 (1H, d, J=1.9 Hz), 6.29 (1H, d, J=3.7 Hz), 5.97 (1H, d, J=3.7 Hz), 4.50 (2H, d, J=6.1 Hz), 3.56 (3H, s), 3.46 (3H, s), 2.26 (3H, s), 2.24 (6H, s). HRMS (M + H) calcd for C$_{21}$H$_{25}$N$_4$O$_3$: 381.19268; found: 381.1929. |
| 99 | 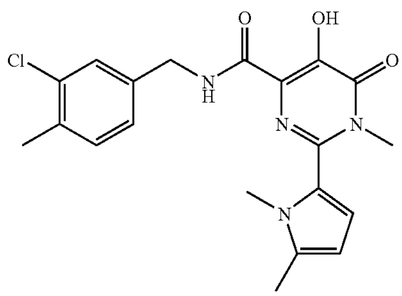 | N-(3-chloro-4-methylbenzyl)-2-(1,5-dimethyl-1H-pyrrol-2-yl)-5-hydroxy-1-methyl-6-oxo-1,6-dihydropyrimidine-4-carboxamide: $^1$H NMR (500 MHz, CDCl$_3$) δ: 12.00 (1H, bs), 7.87 (1H, t, J=5.8 Hz), 7.27 (1H, d, J=1.5 Hfz), 7.19 (1H, d, J=7.6 Hz), 7.09 (1H, dd, J=7.9, 1.5 Hz), 6.29 (1H, d, J=3.7 Hz), 5.98 (1H, dd, J=3.7, 0.9 Hz), 4.52 (2H, d, J=6.4 Hz), 3.57 (3H, s), 3.48 (3H, s), 2.34 (3H, s), 2.27 (3H, s). HRMS (M + H) calcd for C$_{20}$H$_{22}$ClN$_4$O$_3$: 401.13805; found: 401.1381. |
| 100 | 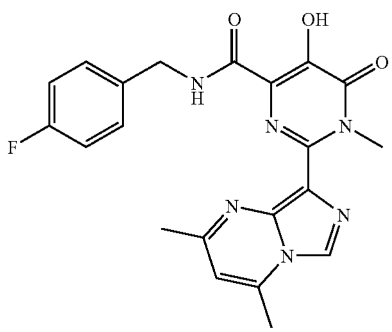 | N-(4-fluorobenzyl)-2-(2,4-dimethylimidazo[1,5-a]pyrimidin-8-yl)-5-hydroxy-1-methyl-6-oxo-1,6-dihydropyrimidine-4-carboxamide: $^1$H NMR (300 MHz, CDCl$_3$) δ: 8.35 (1H, bs), 8.24 (1H, s), 7.31 (2H, dd, J=8.4, 5.3 Hz), 6.99 (2H, t, J=8.7 Hz), 6.58 (1H, s), 4.57 (2H, d, J=6.4 Hz), 3.80 (3H, s), 2.67 (3H, s), 2.46 (3H, s). HRMS (M + H) calcd for C$_{21}$H$_{20}$FN$_6$O$_3$: 423.1581; found: 423.1575. |
| 101 | 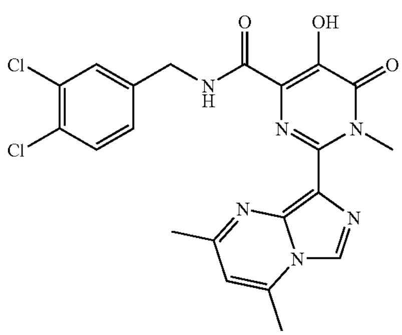 | N-(3,4-dichlorobenzyl)-2-(2,4-dimethylimidazo[1,5-a]pyrimidin-8-yl)-5-hydroxy-1-methyl-6-oxo-1,6-dihydropyrimidine-4-carboxamide: $^1$H NMR (300 MHz, CDCl$_3$) δ: 8.58 (1H, bs), 8.53 (1H, s), 7.42 (1H, s), 7.37 (1h, d, J=8.2 Hz), 7.19 (1H, dd, J=8.2, 1.5 Hz), 6.68 (1H, s), 4.55 (2H, d, J=6.4 Hz), 3.82 (3H, s), 2.71 (3H, s), 2.56 (3H, s). HRMS (M + H) calcd for C$_{21}$H$_{19}$Cl$_2$N$_6$O$_3$: 473.08958; found: 473.0902. |
| 102 | 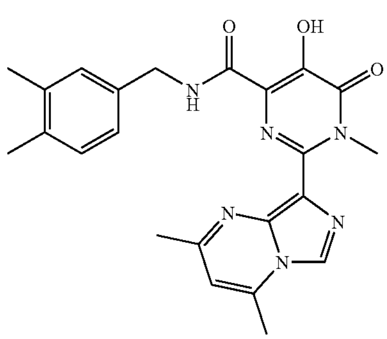 | N-(3,4-dimethylbenzyl)-2-(2,4-dimethylimidazo[1,5-a]pyrimidin-8-yl)-5-hydroxy-1-methyl-6-oxo-1,6-dihydropyrimidine-4-carboxamide: $^1$H NMR (300 MHz, CDCl$_3$) δ: 12.09 (1H, bs), 8.22 (1H, bs), 8.11 (1H, s), 7.10 (1H, s), 7.06 (2H, s), 6.52 (1H, s), 4.52 (2H, d, J=6.1 Hz), 3.79 (3H, s), 2.65 (3H, s), 2.40 (3H, s), 2.22 (3H, s), 2.21 (3H, s). HRMS (M + H) calcd for C$_{23}$H$_{25}$N$_6$O$_3$: 433.19882; found: 433.1996. |

-continued

| Example | Structure | Name and Analytical data |
|---|---|---|
| 103 | 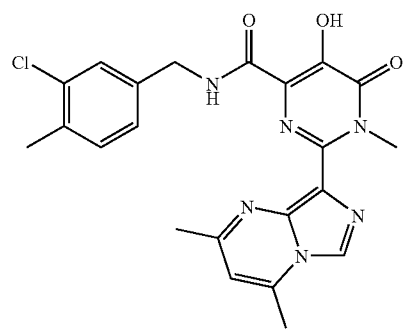 | N-(3-chloro-4-methylbenzyl)-2-(2,4-dimethylimidazo[1,5-a]pyrimidin-8-yl)-5-hydroxy-1-methyl-6-oxo-1,6-dihydropyrimidine-4-carboxamide: $^1$H NMR (300 MHz, CDCl$_3$) δ: 8.52 (1H, s), 8.49 (1H, bs), 7.30 (1H, s), 7.14 (2H, dd, J=15.0, 7.9 Hz), 6.66 (1H, s), 4.53 (2H, d, J=5.8 Hz), 3.82 (3H, s), 2.71 (3H, s), 2.55 (3H, s), 2.31 (3H, s). HRMS (M + H) calcd for C$_{22}$H$_{22}$ClN$_6$O$_3$: 453.1442; found: 453.1447. |
| 104 | 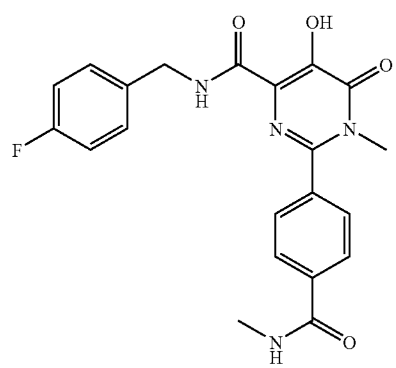 | 2-(4-methylaminicarbonyl-phenyl)-5-hydroxy-1-methyl-6-oxo-1,6-dihydro-pyrimidine-4-carboxylic acid 4-fluorobenzylamide: $^1$H NMR (500 MHz, acetone-d6) δ 12.41 (1H, s), 9.44 (1H, br.s), 9.05 (1H, br.s), 7.79 (2H, d, J=8.5 Hz), 7.55 (2H, d, J=8.5 Hz), 7.09 (2H, m), 7.44 (2H, m), 4.62 (2H, d, J=6.5 Hz), 3.44 (3H, s), 2.14 (3H, s). HRMS calcd for C$_{21}$H$_{18}$FN$_4$O$_4$ (M − H): 409.1312; found: 409.1317. Anal. Calcd for C$_{21}$H$_{19}$FN$_4$O$_4$•H$_2$O: C, 58.81; C, 4.94; N, 13.08; found: C, 58.88; H, 5.40; N, 13.23. |
| 105 | 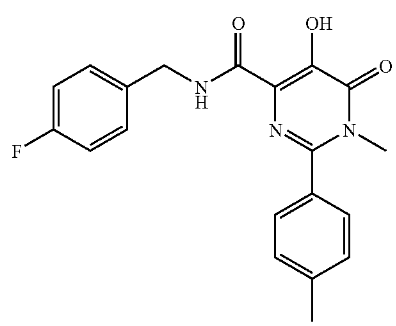 | N-(4-fluorobenzyl)-5-hydroxy-1-methyl-6-oxo-2-p-tolyl-1,6-dihydropyrimidine-4-carboxamide: $^1$H NMR (300 MHz, CDCl$_3$) δ ppm 2.42 (3H, s), 3.45 (3H, s), 4.54 (2H, d, J=6.3 Hz), 7.00 (2H, m), 7.3 (6H, m), 7.92 (1H, br). HRMS (M + H) calcd for C$_{20}$H$_{19}$FN$_3$O$_3$: 368.1410, found 368.1400. |

EXAMPLE 106

HIV-Integrase Inhibition Activity

To evaluate in-vitro activity against HIV-integrase, 5 pmole of biotin labeled substrate DNA was bound to 100 μg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, *J. Virol.* 69, 5908–5911 (1995). The sequences of substrate and target DNA were described in *Nucleic Acid Research* 22,1121–1122 (1994). Using this assay, examples 1–98 were found to have an IC$_{50}$=0.002 to 2 μM.

Although the invention has been described with respect to specific aspects, those skilled in the art will recognize that other aspects not specifically described herein are intended to be within the scope of the claims which follow.

The invention claimed is:

1. A compound of Formula I, or a pharmaceutically acceptable salt or solvate thereof,

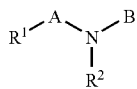

I wherein

A is methylene or 1,1-disubstituted ethylene;

B is selected from the group consisting of

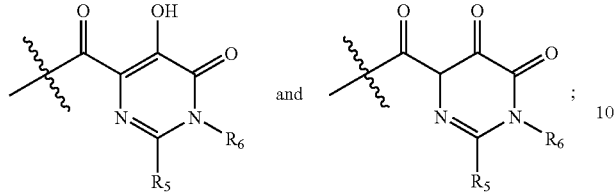

R¹ is phenyl, pyridinyl or dioxolanylphenyl and is unsubstituted or substituted with 1 to 3 R³;

R² is hydrogen, methyl, or OR⁴;

R³ is independently selected from halo, $C_{1-6}$alkyl, $C_{1-2}$perfluoroalkyl, $C_{1-6}$alkoxy, $C_{1-6}$alkylthioxy, and cyano;

R⁴ is hydrogen or $C_{1-6}$alkyl;

R⁵ is Ar¹ or Ar²;

R⁶ is $C_{1-6}$alkyl;

Ar¹ is phenyl substituted with 1 dioxothiazinanyl;

Ar² is a heteroaryl moiety selected from the group consisting of pyridinyl, pyrrolyl, furanyl, and imidazopyrimidinyl and is substituted with 1 dioxothiazinanyl.

2. A compound of claim 1 wherein R¹ is phenyl unsubstituted or substituted with 1 to 3 R³.

3. A compound of claim 2 where R¹ is phenyl substituted with 1–2 R³ selected from the group consisting of chloro, fluoro, methyl, and trifluoromethyl.

4. A compound of claim 1 where R² is hydrogen.

5. A compound of claim 1 where R⁵ is Ar¹.

6. A compound of claim 5 selected from the group consisting of

N-(3,4-dichlorobenzyl)-5-hydroxy-1-methyl-2-(2-(1,1-Dioxo-1λ⁶-[1,2]thiazinan-2-yl)-6-oxo-1,6-dihydropyrimidine-4-carboxamide;

N-(3,4-dimethylbenzyl)-5-hydroxy-1-methyl-2-(2-(1,1-Dioxo-1λ¹-[1,2]thiazinan-2-yl)-6-oxo-1,6-dihydropyrimidine-4-carboxamide; and N-(3-chloro-4-methylbenzyl)-5-hydroxy-1-methyl-2-(2-(1,1-Dioxo-1λ⁶-[1,2]thiazinan-2-yl)-6-oxo-1,6-dihydropyrimidine-4-carboxamide;

or a pharmaceutically acceptable salt or solvate thereof.

7. A compound of claim 1 where R⁵ is Ar².

8. A compound of claim 7 selected from the group consisting of

N-(4-fluorobenzyl)-5-hydroxy-2-(3-[2-(1,1-Dioxo-1λ⁶-[1,2]thiazinan-2-yl)-pyridin-2-yl]-)-1-methyl-6-oxo-1,6-dihydropyrimidine-4-carboxamide;

N-(3,4-dichlorobenzyl)-5-hydroxy-2-(3-[2-(1,1-Dioxo-1λ⁶-[1,2]thiazinan-2-yl)-pyridin-2-yl]-)-1-methyl-6-oxo-1,6-dihydropyrimidine-4-carboxamide;

N-(3,4-dimethylbenzyl)-5-hydroxy-2-(3-[2-(1,1-Dioxo-1λ⁶-[1,2]thiazinan-2-yl)-pyridin-2-yl]-)-1-methyl-6-oxo-1,6-dihydropyrimidine-4-carboxamide; and N-(3-chloro-4-methylbenzyl)-5-hydroxy-2-(3-[2-(1,1-Dioxo-1λ⁶-[1,2]thiazinan-2yl)-pyridin-2-yl]-)-1-methyl-6-oxo-1,6-dihydropyrimidine-4-carboxamide;

or a pharmaceutically acceptable salt or solvate thereof.

9. A compound of claim 1 where R⁶ is methyl.

10. A composition useful for treating HIV infections comprising a therapeutic amount of a compound of claim 1, or a salt or solvate thereof, and a pharmaceutically acceptable carrier.

11. A method of inhibiting HIV integrase which comprises administering to a patient a therapeutically effective amount of a compound of claim 1, or a pharmaceutically acceptable salt or solvate thereof.

12. A method of treating HIV infection in a patient comprising the administration of a therapeutically effective amount of a compound of claim 1, or a pharmaceutically acceptable salt or solvate thereof.

13. The method of claim 12 further comprising administering a therapeutically effective amount of a compound of claim 1 with at least one other agent for treating HIV selected from the group consisting of HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *